US008865725B2

(12) United States Patent
Conn et al.

(10) Patent No.: US 8,865,725 B2
(45) Date of Patent: Oct. 21, 2014

(54) SUBSTITUTED IMIDAZOPYRIMIDIN-5(6H)-ONES AS ALLOSTERIC MODULATORS OF MGLUR5 RECEPTORS

(75) Inventors: P. Jeffrey Conn, Nashville, TN (US); Craig W. Lindsley, Brentwood, TN (US); Shaun R. Stauffer, Brentwood, TN (US); Jose Manuel Bartolome-Nebreda, Toledo (ES); Gregor James MacDonald, Beerse (BE); Susana Conde-Ceide, Toledo (ES); Carrie K. Jones, Nashville, TN (US); Maria Luz Martin-Martin, Toledo (ES); Han Min Tong, Toledo (ES)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/420,333

(22) Filed: Mar. 14, 2012

(65) Prior Publication Data

US 2013/0245043 A1 Sep. 19, 2013

Related U.S. Application Data

(60) Provisional application No. 61/452,921, filed on Mar. 15, 2011.

(51) Int. Cl.
*A01N 43/90* (2006.01)
*A61K 31/519* (2006.01)
*C07D 487/00* (2006.01)

(52) U.S. Cl.
USPC ........................................ 514/259.1; 544/281

(58) Field of Classification Search
None
See application file for complete search history.

(56) References Cited

U.S. PATENT DOCUMENTS

| 4,643,999 | A | 2/1987 | Tully |
| 4,973,588 | A | 11/1990 | Kihara |
| 2008/0039476 | A1 | 2/2008 | Danysz |
| 2009/0270362 | A1 | 10/2009 | Conn |

FOREIGN PATENT DOCUMENTS

| WO | WO 2006/129199 | 12/2006 | | |
| WO | WO 2008/074679 | 6/2008 | | |
| WO | WO 2009/095254 | 8/2009 | | |
| WO | WO 2012125732 | * 9/2012 | ............. | A01N 43/42 |

OTHER PUBLICATIONS

Chawla et. al. Current Research & Information on Pharmaceutical Science, 2004, 5(1), 9-12.*

Newman et. al.; Drug Discovery Today; 2003, 8(19) 898-905.*
Almarasson O, et al. (2004) Crystal engineering of the composition of pharmaceutical phases. Do pharmaceutical co-crystals represent a new path to improved medicines? Chem. Comm., 17: 1889-1896.
Awad H, et al. (2000) Activation of metabotropic glutamate receptor 5 has direct excitatory effects and potentiates NMDA receptor currents in neurons of the subthalamic nucleus. J Neurosci., 20(21): 7871-7879.
Chavez-Noriega L, et al. (2002) Metabotropic Glutamate Receptors: Potential Drug Targets for the Treatment of Schizophrenia. Current Drug Targets—CNS & Neurological Disorders, 1: 261-281.
Chiamulera C, et al. (2001) Reinforcing and locomotor stimulant effects of cocaine are absent in mGluR5 null mutant mice. Nature, 4(9): 873-874.
Santolini, I., et al. (2011) Pharmacological activation of metabotropic glutamate receptor subtype 5 reduces Spike and Wave Discharges in the WAG/Rij rat model of absence epilepsy. Abstract from 7th International conference on metabotropic glutamate receptors, Taormina, Italy.
Kinney G, et al. (2005) A Novel Selective Positive Allosteric Modulator of Metabotropic Glutamate Receptor Subtype 5 Has in Vivo Activity and Antipsychotic-Like Effects in Rat Behavioral Models. The Journal of Pharmacology and Experimental Therapeutics, 313(1): 199-206.
Malherbe P, et al. (2003) Mutational Analysis and Molecular Modeling of the Binding Pocket of the Metabotropic Glutamate 5'Receptor Negative Modulator 2-Methyl-6-(phenylethynyl)-pyridine. Molecular Pharmacology, 64(4): 823-832.
Mannaioni G, et al. (2001) Metabotropic Glutamate Receptors 1 and 5 Differentially Regulate CA1 Pyramidal Cell Function. The Journal of Neuroscience, 21(6): 5925-5934.
Myllymäki MJ, et al. (200) Chiral 3-(4,5-dihydrooxazol-2-yl)phenyl alkylcarbamates as novel FAAH inhibitors: Insight into FAAH enantioselectivity by molecular docking and interaction fields. Eur J Med Chem, 44(10): 4179-4191.
Ngomba R, et al. (2011) Metabotropic glutamate receptors in the thalamocortical network: Strategic targets for the treatment of absence epilepsy. Epilepsia, 52(7): 1211-1222.
Ngomba RT, et al. (2011) Protective role for type-1 metabotropic glutamate receptors against spike and wave discharges in the WAG/Rij rat model of absence epilepsy. Neuropharmacology, 60(7-8): 1281-1291.
Noll S, et al. (2009) Synthesis of modified pyrimidine bases and positive impact of chemically reactive substituents on their in vitro antiproliferative activity. Eur. J. Med. Chem., 44(3): 1172-1179.
Ossowska K, et al. (2001) Blockade of the metabotropic glutamate receptor subtype 5 (mGluR5) produces antiparkinsonian-like effects in rats. Neuropharmacology 41: 413-420.

(Continued)

*Primary Examiner* — Jeffrey H Murray
(74) *Attorney, Agent, or Firm* — Ballard Spahr LLP

(57) ABSTRACT

In one aspect, the invention relates to imidazopyrimidin-5 (6H)-one analogs, derivatives thereof, and related compounds, which are useful as positive allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

12 Claims, 3 Drawing Sheets

(56) References Cited

OTHER PUBLICATIONS

Oyarzabal J, et al. (2009) Novel Approach for Chemotype Hopping Based on Annotated Databases of Chemically Feasible Fragments and a Prospective Case Study: New Melanin Concentrating Hormone Antagonists. J. Med. Chem., 52: 2076-2089.

Salt T, et al. (2001) Contributions of mGlu1 and mGlu5 Receptors to Interactions with N-Methyl-$_D$-Aspartate Receptor-Mediated Responses and Nociceptive Sensory Responses of Rat Thalamic Neurons. Neuroscience, 100(2): 375-380.

Spooren W, et al. (2000) Anxiolytic-Like Effects of the Prototypical Metabotropic Glutamate Receptor 5 Antagonist 2-Methyl-6-(phenylethynyl)pyridine in Rodents. J Pharmacol Exp Ther, 295(3): 1267-1275.

Tatarczyńska E, et al. (2001) Potential anxiolytic- and antidepressant-like effects of MPEP, a potent, selective and systemically active mGLu5 receptor antagonist. British Journal of Pharmacology, 132: 1423-1430.

Yang Y, et al. (2005) Copper-Catalyzed Cross-Coupling Reactions of Nucleobases with Arylboronic Acids: An Efficient Access to N-Arylnucleobases. Eur. J. Org. Chem., 24: 5154-5157.

International Preliminary Report on Patentability issued by the International Bureau on Jun. 18, 2013 for PCT/US2011/065598 filed on Dec. 16, 2011 and published as WO 2012/083224 on Jun. 21, 2012 (Applicant—Vanderbilt University // Inventors—Conn et al.) (1 page).

International Search Report issued by the International Bureau on Apr. 25, 2012 for PCT/US2011/065598 filed on Dec. 16, 2011 and published as WO 2012/083224 on Jun. 21, 2012 (Applicant—Vanderbilt University // Inventors—Conn et al.) (2 pages).

Written Opinion issued by the International Bureau on Apr. 25, 2012 for PCT/US2011/065598 filed on Dec. 16, 2011 and published as WO 2012/083224 on Jun. 12, 2012 (Applicant—Vanderbilt University // Inventors—Conn et al.) (5 pages).

International Search Report issued by the International Bureau on Jun. 22, 2012 for PCT/US2012/029085 filed on Mar. 14, 2012 and published as WO 2012/125732 on Sep. 20, 2012 (Applicant—Vanderbilt University // Inventors Conn et al.) (2 pages).

\* cited by examiner

SUBSTITUTED IMIDAZOPYRIMIDIN-5(6H)-ONES AS ALLOSTERIC MODULATORS OF MGLUR5 RECEPTORS

CROSS-REFERENCE TO RELATED APPLICATIONS

This application claims the benefit of U.S. Provisional Application No. 61/452,921, filed on Mar. 15, 2011, which is incorporated herein by reference in its entirety.

ACKNOWLEDGMENT

This invention was made with government support under grant numbers MH062646, MH073676 and MH082867 awarded by the National Institute of Mental Health (NIMH), and under grant number NS031373 awarded by the National Institute of Neurological Disorders and Stroke. The United States government has certain rights in the invention.

BACKGROUND

Glutamate (L-glutamic acid) is the major excitatory transmitter in the mammalian central nervous system, exerting its effects through both ionotropic and metabotropic glutamate receptors. The metabotropic glutamater receptors (mGluRs) belong to family C (also known as family 3) of the G-protein-coupled receptors (GPCRs). They are characterized by a seven transmembrane (7TM) α-helical domain connected via a cysteine rich-region to a large bi-lobed extracellular amino-terminal domain (FIG. 3). While the orthosteric binding site is contained in the amino-terminal domain, currently known allosteric binding sites reside in the 7TM domain. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. The family has been classified into three groups based on their structure, preferred signal transduction mechanisms, and pharmacology.

Group I receptors (mGluR1 and mGluR5) are coupled to Gαq, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to Gαi, which leads to decreases in cyclic adenosine monophosphate (cAMP) levels. While the Group I receptors are predominately located postsynaptically and typically enhance postsynaptic signaling, the group II and III receptors are located presynaptically and typically have inhibitory effects on neurotransmitter release.

Without wishing to be bound by a particular theory, metabotropic glutamate receptors, including mGluR5, have been implicated in a wide range of biological functions, indicating a potential role for the mGluR5 receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like. Further, without wishing to be bound by theory, increasing evidence indicates mGluRs play an important role in lasting changes in synaptic transmission, and studies of synaptic plasticity in the Fmr1 knockout mouse have identified a connection between the fragile X phenotype and mGluR signaling.

The identification of small molecule mGluR agonists that bind at the orthosteric site has greatly increased the understanding of the roles played by these receptors and their corresponding relation to disease. Because the majority of these agonists were designed as analogs of glutamate, they typically lack the desired characteristics for drugs targeting mGluR such as oral bioavailability and/or distribution to the central nervous system (CNS). Moreover, because of the highly conserved nature of the glutamate binding site, most orthosteric agonists lack selectivity among the various mGluRs.

Selective positive allosteric modulators ("PAMs") are compounds that do not directly activate receptors by themselves, but binding of these compounds potentiates the response of the receptor to glutamate or other orthosteric agonists by either increasing the affinity of an orthosteric agonist at the orthosteric binding site or enhancing coupling to the G-protein or both. PAMs are thus an attractive mechanism for enhancing appropriate physiological receptor activation.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive allosteric modulators for the mGluR5 receptor.

SUMMARY

In accordance with the purpose(s) of the invention, as embodied and broadly described herein, the invention, in one aspect, relates to compounds useful as positive allosteric modulators (i.e., potentiators) of the metabotropic glutamate receptor subtype 5 (mGluR5), methods of making same, pharmaceutical compositions comprising same, and methods of treating neurological and psychiatric disorders associated with glutamate dysfunction using same.

Disclosed are compounds having a structure represented by a formula:

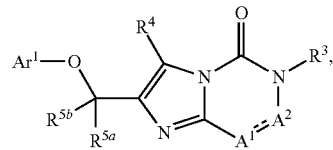

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are pharmaceutical compositions comprising a therapeutically effective amount of a disclosed compound and a pharmaceutically acceptable carrier.

Also disclosed are synthetic methods comprising the steps of: (a) providing a compound having a structure represented by a formula:

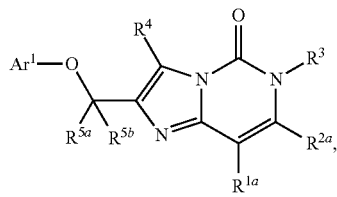

wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein R$^3$ is selected from phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein R$^4$ is selected from hydrogen, halogen, cyano, and C1-C4 alkyl; wherein each of R$^{5a}$ and R$^{5b}$ is independently selected from hydrogen and C1-C4 alkyl; wherein R$^{1a}$ and R$^{2a}$ are optionally covalently bonded and, together with the intermediate atoms, comprise an optionally substituted 3- to 7-membered fused cycloalkyl, and (b) hydrogenating the compound, thereby yielding a compound having a structure represented by a formula:

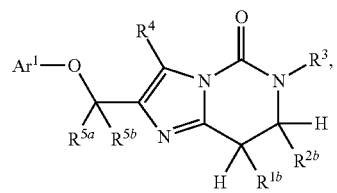

Also disclosed are synthetic methods comprising the steps of: (a) providing a compound having a structure represented by a formula:

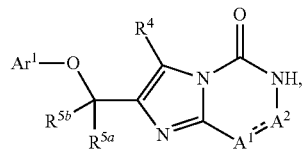

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl, and (b) reacting the compound with $R^3X$, wherein X is a leaving group, and wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and wherein $R^3$, when ----- is not present, is $Ar^2$; thereby substituting at the amide.

Also disclosed are synthetic methods comprising the steps of: (a) providing a compound having a structure represented by a formula:

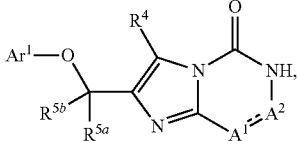

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) coupling the compound with $R^3X$, in the presence of a coupling reagent, wherein X is bromo or iodo, and wherein $R^3$, when is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl C1-C4 polyhaloalkyl, —$NH_2$, —NH(C1-C4 alkyl), and —N(C1-C4 alkyl)(C1-C4 alkyl); and wherein $R^3$, when is not present, is $Ar^2$; thereby substituting at the amide.

Also disclosed are synthetic methods comprising the steps of: (a) providing a compound having a structure represented by a formula:

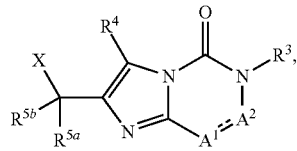

wherein X is a leaving group; wherein ----- is an optional covalent bond, wherein valence is satisfied; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); and, wherein R³, when ----- is not present, is Ar²; wherein R⁴ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) reacting the compound with Ar¹OH, wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl, thereby yielding a compound having a structure represented by a formula:

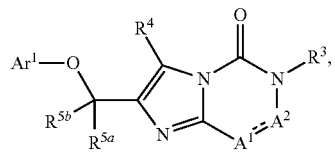

Also disclosed are synthetic methods comprising the steps of: (a) providing a compound having a structure represented by a formula:

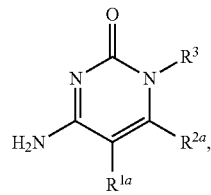

wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein R³ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar²; wherein Ar² is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl), or Ar² is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); and reacting the compound with a compound represented by the formula:

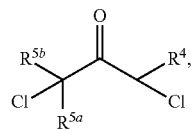

wherein R⁴ is selected from hydrogen, halogen, cyano, and C1-C4 alkyl; and wherein each of $R^{5a}$ and $R^{5b}$ is independently selected from hydrogen and C1-C4 alkyl.

Also disclosed are synthetic methods comprising the steps of: (a) providing a compound having a structure represented by a formula:

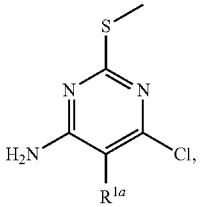

wherein $R^{1a}$ is selected from hydrogen, halogen, C1-C4 alkyl, C1-C4 monohaloalkyl, and C1-C4 polyhaloalkyl, and (b) reacting the compound with a compound represented by a formula:

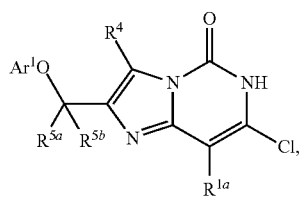

wherein R⁴ is selected from hydrogen, halogen, cyano, and C1-C4 alkyl; and wherein each of $R^{5a}$ and $R^{5b}$ is independently selected from selected from hydrogen, C1-C4 alkyl, C1-C4 monohaloalkyl, and C1-C4 polyhaloalkyl.

Also disclosed are synthetic methods comprising the steps of: (a) providing a compound having a structure represented by a formula:

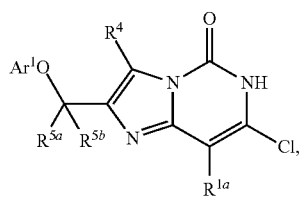

wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein $R^{1a}$ is selected from hydrogen, halogen, C1-C4 alkyl, C1-C4 monohaloalkyl, and C1-C4 polyhaloalkyl; wherein R⁴ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) hydrogenating the compound, thereby yielding a compound having a structure represented by a formula:

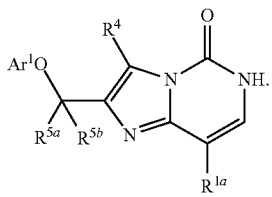

Also disclosed are synthetic methods comprising the steps of: (a) providing a compound having a structure represented by a formula:

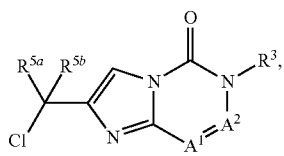

wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and wherein each of $R^{5a}$ and $R^{5b}$ is independently selected from hydrogen, C1-C4 alkyl, C1-C4 monohaloalkyl, and C1-C4 polyhaloalkyl; and (b) halogenating the compound by reaction with N-halosuccinimide.

Also disclosed are synthetic methods comprising the steps of: (a) providing a compound having a structure represented by a formula:

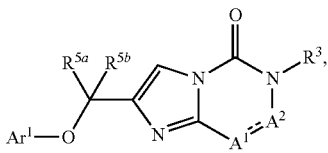

wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and wherein each of $R^{5a}$ and $R^{5b}$ is independently selected from hydrogen, C1-C4 alkyl, C1-C4 monohaloalkyl, and C1-C4 polyhaloalkyl; and (b) halogenating the compound by reaction with N-halosuccinimide.

Also disclosed are synthetic methods comprising the steps of: (a) providing a compound having a structure represented by a formula:

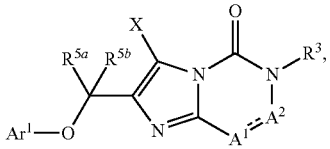

wherein X is halogen; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and wherein each of $R^{5a}$ and $R^{5b}$ is independently selected from hydrogen, C1-C4 alkyl, C1-C4 monohaloalkyl, and C1-C4 polyhaloalkyl; and (b) reacting the compound with $R^6OH$ in the presence of a base, wherein $R^6$ is C1-C4 alkyl, thereby yielding a compound having a structure represented by a formula:

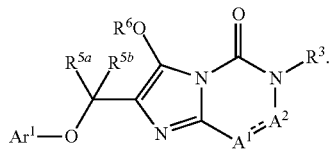

Also disclosed are synthetic methods comprising the steps of: (a) providing a compound having a structure represented by a formula:

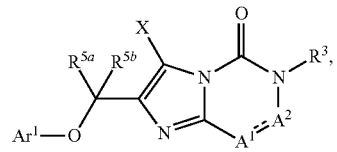

wherein X is halogen; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and wherein each of $R^{5a}$ and $R^{5b}$ is independently selected from hydrogen, C1-C4 alkyl, C1-C4 monohaloalkyl, and C1-C4 polyhaloalkyl; and (b) reacting the compound with NR⁷R⁸ in the presence of a metal catalyst, wherein each of R⁷ and R⁷ are independently selected from H and C1-C4 alkyl, thereby yielding a compound having a structure represented by a formula:

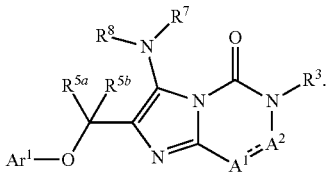

Also disclosed are synthetic methods comprising the steps of: (a) providing a compound having a structure represented by a formula:

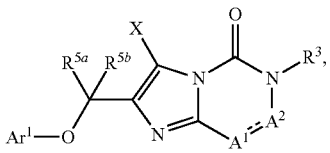

wherein X is halogen; wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A¹ and A² are joined by a covalent double bond, A¹ is CR¹ᵃ, and A² is CR²ᵃ; wherein R¹ᵃ is selected from hydrogen, halogen, C1-C4 alkyl, C1-C4 monohaloalkyl, and C1-C4 polyhaloalkyl; wherein R²ᵃ is selected from hydrogen, C1-C4 alkyl, C1-C4 monohaloalkyl, and C1-C4 polyhaloalkyl; wherein when ----- is not present and A¹ and A² are joined by a covalent single bond, A¹ is CR¹ᵇR¹ᶜ, and A² is CR²ᵇR²ᶜ; wherein each of R¹ᵇ and R¹ᶜ are independently selected from hydrogen, fluoro, C1-C4 alkyl, C1-C4 monohaloalkyl, and C1-C4 polyhaloalkyl, or R¹ᵇ and R¹ᶜ are covalently bonded and, together with the intermediate atoms, comprise an optionally substituted 3- to 7-membered spirocycloalkyl; wherein each of R²ᵇ and R²ᶜ are independently selected from hydrogen, C1-C4 alkyl, C1-C4 monohaloalkyl, and C1-C4 polyhaloalkyl, or R²ᵇ and R²ᶜ are covalently bonded and, together with the intermediate atoms, comprise an optionally substituted 3- to 7-membered spirocycloalkyl; wherein R¹ᵃ and R²ᵃ, when present, are optionally covalently bonded and, together with the intermediate atoms, comprise an optionally substituted 3- to 7-membered fused cycloalkenyl; wherein R¹ᵇ and R²ᵇ, when present, are optionally covalently bonded and, together with the intermediate atoms, comprise an optionally substituted 3- to 7-membered fused cycloalkyl; wherein R³ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar²; wherein Ar² is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl), or Ar² is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); and wherein each of R⁵ᵃ and R⁵ᵇ is independently selected from hydrogen, C1-C4 alkyl, C1-C4 monohaloalkyl, and C1-C4 polyhaloalkyl; and (b) reacting the compound with R⁹B(OH)₂ in the presence of a metal catalyst, wherein R⁹ is selected from C1-C4 alkyl, C1-C4 monohaloalkyl, and C1-C4 polyhaloalkyl thereby yielding a compound having a structure represented by a formula:

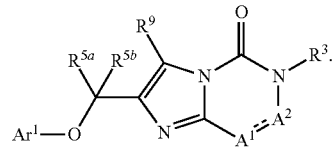

Disclosed are methods for the treatment of a neurological and/or psychiatric disorder associated with glutamate dysfunction in a mammal comprising the step of administering to the mammal a therapeutically effective amount of at least one compound having a structure represented by a formula:

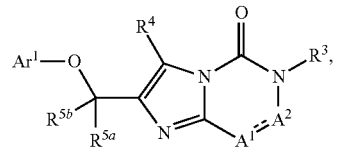

wherein ----- is an optional covalent bond, wherein valence is satisfied; wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A¹ and A² are joined by a covalent double bond, A¹ is CR¹ᵃ, and A² is CR²ᵃ; wherein R¹ᵃ is selected from hydrogen, halogen, C1-C4 alkyl, C1-C4 monohaloalkyl, and C1-C4 polyhaloalkyl; wherein R²ᵃ is selected from hydrogen, C1-C4 alkyl, C1-C4 monohaloalkyl, and C1-C4 polyhaloalkyl; wherein when ----- is not present and A¹ and A² are joined by a covalent single bond, A¹ is CR¹ᵇR¹ᶜ and A² is CR²ᵇR²ᶜ; wherein each of R¹ᵇ and R¹ᶜ are independently selected from hydrogen, fluoro, C1-C4 alkyl, C1-C4 monohaloalkyl, and C1-C4 polyhaloalkyl, or R¹ᵇ and R¹ᶜ are covalently bonded and, together with the intermediate atoms, comprise an optionally substituted 3- to 7-membered spirocycloalkyl; wherein each of R²ᵇ and R²ᶜ are independently selected from hydrogen, C1-C4 alkyl, C1-C4 monohaloalkyl, and C1-C4 polyhaloalkyl, or R²ᵇ and R²ᶜ are covalently bonded and, together with the intermediate atoms, comprise an optionally substituted 3- to 7-membered spirocycloalkyl; wherein R¹ᵃ and R²ᵃ, when present, are optionally covalently bonded and, together with the intermediate atoms, comprise an optionally substituted 3- to 7-membered fused cycloalkenyl; wherein R¹ᵇ and R²ᵇ, when present, are optionally covalently bonded and, together with the intermediate atoms, comprise an optionally substituted 3- to 7-membered fused cycloalkyl; wherein R³, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl;

(C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods for the treatment of a disease of uncontrolled cellular proliferation in a mammal comprising the step of administering to the mammal a therapeutically effective amount of at least one compound having a structure represented by a formula:

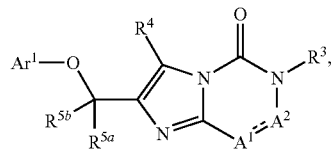

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods for potentiation of metabotropic glutamate receptor activity in a mammal comprising the step of administering to the mammal a therapeutically effective amount of at least one compound having a structure represented by a formula:

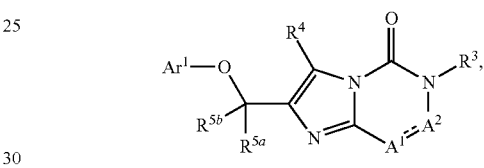

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods for partial agonism of metabotropic glutamate receptor activity in a mammal comprising the step of administering to the mammal a therapeutically effective amount of at least one compound having a structure represented by a formula:

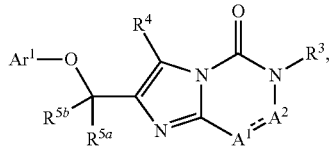

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods for enhancing cognition in a mammal comprising the step of administering to the mammal an effective amount of at least one compound having a structure represented by a formula:

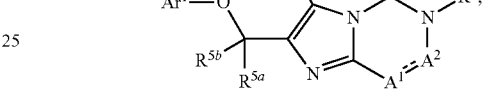

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods for modulating mGluR5 activity in a mammal comprising the step of administering to the mammal an effective amount of at least one compound having a structure represented by a formula:

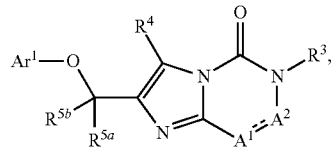

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are methods modulating mGluR5 activity in at least one cell, comprising the step of contacting the at least one cell with an effective amount of at least one compound having a structure represented by a formula:

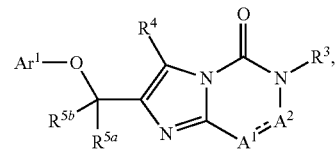

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

Also disclosed are kits comprising at least one compound having a structure represented by a formula:

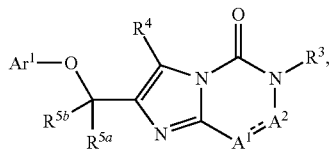

wherein ----- is an optional covalent bond, wherein valence is satisfied; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein R$^3$, when ----- is not present, is Ar$^2$; wherein R$^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of R$^{5a}$ and R$^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof, and one or more of: (a) at least one agent known to increase mGluR5 activity; (b) at least one agent known to decrease mGluR5 activity; (c) at least one agent known to treat a neurological and/or psychiatric disorder; (d) at least one agent known to treat a disease of uncontrolled cellular proliferation; or (e) instructions for treating a disorder associated with glutamate dysfunction.

Also disclosed are methods for manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with glutamate dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
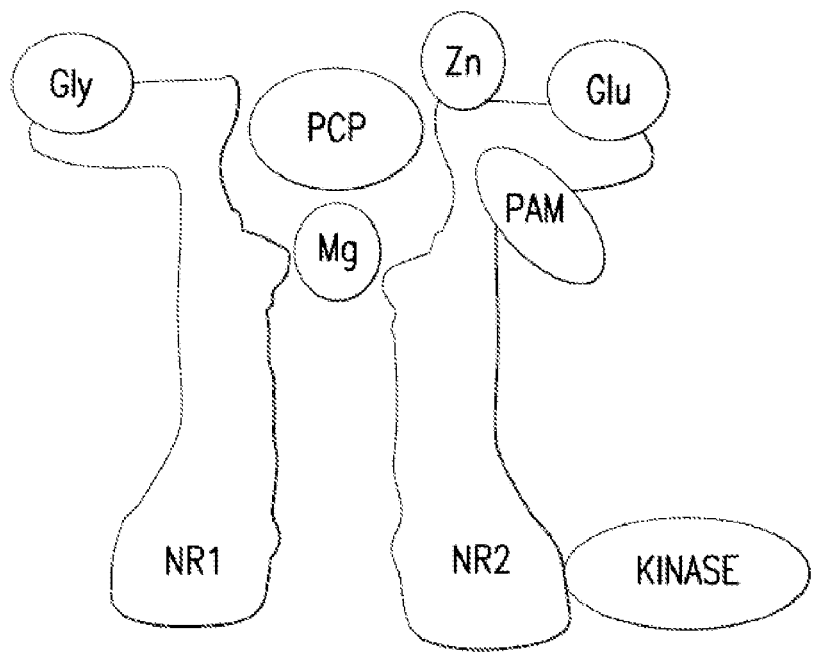
FIG. 1 shows a schematic of the NMDA receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mGluR5 receptor is the site that glutamate binds.

As used herein, the term "mGluR5 receptor positive allosteric modulator" refers to any exogenously administered compound or agent that directly or indirectly augments the activity of the mGluR5 receptor in the presence or in the absence of glutamate in an animal, in particular a mammal, for example a human. In one aspect, a mGluR5 receptor positive allosteric modulator increases the activity of the mGluR5 receptor in a cell in the presence of extracellular glutamate. The cell can be human embryonic kidney cells transfected with human mGluR5. The cell can be human embryonic kidney cells transfected with rat mGluR5. The cell can be human embryonic kidney cells transfected with a mammalian mGluR5 The term "mGluR5 receptor positive allosteric modulator" includes a compound that is a "mGluR5 receptor allosteric potentiator" or a "mGluR5 receptor allosteric agonist," as well as a compound that has mixed activity comprising pharmacology of both an "mGluR5 receptor allosteric potentiator" and an "mGluR5 receptor allosteric agonist". The term "mGluR5 receptor positive allosteric modulator also includes a compound that is a "mGluR5 receptor allosteric enhancer."

As used herein, the term "mGluR5 receptor allosteric potentiator" refers to any exogenously administered compound or agent that directly or indirectly augments the response produced by the endogenous ligand (such as glutamate) when the endogenous ligand binds to the orthosteric site of the mGluR5 receptor in an animal, in particular a mammal, for example a human. The mGluR5 receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as an mGluR5 receptor allosteric potentiator provides advantages over the use of a pure mGluR5 receptor allosteric agonist. Such advantages can include, for example, increased safety margin, higher tolerability, diminished potential for abuse, and reduced toxicity.

As used herein, the term "mGluR5 receptor allosteric enhancer" refers to any exogenously administered compound or agent that directly or indirectly augments the response produced by the endogenous ligand in an animal, in particular a mammal, for example a human. In one aspect, the allosteric enhancer increases the affinity of the natural ligand or agonist for the orthosteric site. In another aspect, an allosteric enhancer increases the agonist efficacy. The mGluR5 receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mGluR5 receptor allosteric agonist" refers to any exogenously administered compound or agent that directly activates the activity of the mGluR5 receptor in the absence of the endogenous ligand (such as glutamate) in an animal, in particular a mammal, for example a human. The mGluR5 receptor allosteric agonist binds to a site that is distinct from the orthosteric glutamate site of the mGluR5. Because it does not require the presence of the endogenous ligand, activity of a compound as an mGluR5 receptor allosteric agonist provides advantages over the use of a pure mGluR5 receptor allosteric potentiator, such as more rapid onset of action.

As used herein, the term "mGluR5 receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for positive allosteric modulation of metabotropic glutamate receptor activity prior to the administering step. In some aspects of the disclosed method, the subject has been diagnosed with a need for partial agonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for positive allosteric modulation of metabotropic glutamate receptor activity" refers to having been subjected to a physical examination by a person of skill, for example, a physician, and found to have a condition that can be diagnosed or treated by positive allosteric modulation of metabotropic glutamate receptor activity. For example, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14 th edition), the Physicians' Desk Reference (64 th edition), and The Pharmacological Basis of Therapeutics (12 th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an in vitro assay. For example, an $EC_{50}$ for mGluR5 receptor can be determined in an in vitro or cell-based assay system. Such in vitro assay systems frequently utilize a cell line that either expresses endogenously a target of interest, or has been transfected with a suitable expression vector that directs expression of a recombinant form of the target such as mGluR5. For example, the $EC_{50}$ for mGluR5 can be determined using human embryonic kidney (HEK) cells transfected with human mGluR5. Alternatively, the $EC_{50}$ for mGluR5 can be determined using human embryonic kidney (HEK) cells transfected with rat mGluR5. In another example, the $EC_{50}$ for mGluR5 can be determined using human embryonic kidney (HEK) cells transfected with a mammalian mGluR5.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay. For example, an $IC_{50}$ for mGluR5 receptor can be determined in an in vitro or cell-based assay system. Frequently, receptor assays, including suitable assays for mGluR5, make use of a suitable cell-line, e.g. a cell line that either expresses endogenously a target of interest, or has been transfected with a suitable expression vector that directs expression of a recombinant form of the target such as mGluR5. For example, the $IC_{50}$ for mGluR5 can be determined using human embryonic kidney (HEK) cells transfected with human mGluR5. Alternatively, the $IC_{50}$ for mGluR5 can be determined using human embryonic kidney (HEK) cells transfected with rat mGluR5. In another example, the $IC_{50}$ for mGluR5 can be determined using human embryonic kidney (HEK) cells transfected with a mammalian mGluR5.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. It is understand that the alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C105 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The cycloalkenyl group can be substituted or unsubstituted. The cycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The cycloalkynyl group can be substituted or unsubstituted. The cycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formulas —NH(-alkyl) and —N(-alkyl)$_2$, and where alkyl is as described herein. The alkyl group can be a C1 alkyl, C1-C2 alkyl, C1-C3 alkyl, C1-C4 alkyl, C105 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl) amino group, (tert-butyl)amino group, pentylamino group, isopentylamino group, (tert-pentyl)amino group, hexylamino group, N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, dihexylamino group, N-ethyl-N-methylamino group, N-methyl-N-propylamino group, N-ethyl-N-propylamino group, and the like.

The term "monoalkylamino" as used herein is represented by the formula —NH(-alkyl), where alkyl is as described herein. The alkyl group can be a C1 alkyl, C1-C2 alkyl, C1-C3 alkyl, C1-C4 alkyl, C105 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$, where alkyl is as described herein. The alkyl group can be a C1 alkyl, C1-C2 alkyl, C1-C3 alkyl, C1-C4 alkyl, C105 alkyl, C1-C6 alkyl, C1-C7 alkyl, C1-C8 alkyl, C1-C9 alkyl, C1-C10 alkyl, and the like, up to and including a C1-C24 alkyl. It is understood that each alkyl group can be independently varied, e.g. as in the representative compounds such as N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "carboxylic acid" as used herein is represented by the formula —C(O)OH.

The term "ester" as used herein is represented by the formula —OC(O)$A^1$ or C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted, and the heteroaryl group can be monocyclic, bicyclic or multicyclic aromatic ring. The heteroaryl group can be substituted with one or more groups including, but not limited to, alkyl, cycloalkyl, alkoxy, amino, ether, halide, hydroxy, nitro, silyl, sulfo-oxo, or thiol as described herein. It is understood that a heteroaryl group may be bound either through a heteroatom in the ring, where chemically possible, or one of carbons comprising the heteroaryl ring.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Non-limiting examples of heteroaryl rings include furyl, pyrrolyl, pyrazolyl, imidazolyl, triazolyl, pyridinyl, pyridazinyl, pyrimidinyl, pyrazinyl, azepinyl, triazinyl, thienyl, oxazolyl, thiazolyl, oxadiazolyl, oxatriazolyl, oxepinyl, thiepinyl, diazepinyl, benzofuranyl, thionapthene, indolyl, benzazolyl, pyranopyrrolyl, isoindazolyl, indoxazinyl, benzoxazolyl, quinolinyl, isoquinolinyl, benzodiazonyl, naphthyridinyl, benzothienyl, pyridopyridinyl, acridinyl, carbazolyl and purinyl rings.

The term "monocyclic heteroaryl," as used herein, refers to a monocyclic ring system which is aromatic and in which at least one of the ring atoms is a heteroatom. Monocyclic heteroaryl groups include, but are not limited, to the following exemplary groups: pyridine, pyrimidine, pyridazine, pyrazine, furan, thiophene, pyrrole, isoxazole, isothiazole, pyrazole, oxazole, thiazole, imidazole, oxadiazole, including, 1,2,3-oxadiazole, 1,2,5-oxadiazole and 1,3,4-thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, triazine, including 1,2,4-triazine and 1,3,5-triazine, tetrazine, including 1,2,4,5-tetrazine, and the like. Monocyclic heteroaryl groups are numbered according to standard chemical nomenclature.

The term "bicyclic heteroaryl," as used herein, refers to a ring system comprising a bicyclic ring system in which at least one of the two rings is aromatic and at least one of the two rings contains a heteroatom. Bicyclic heteroaryl encompasses ring systems wherein an aromatic ring is fused with another aromatic ring, or wherein an aromatic ring is fused with a non-aromatic ring. Bicyclic heteroaryl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Examples of bicyclic heteroaryl groups include without limitation indolyl, isoindolyl, indolinyl, indolizinyl, quinolinyl, isoquinolinyl, benzofuryl, bexothiophenyl, indazolyl, benzimidazolyl, benzothiazinyl, benzothiazolyl, purinyl, quinolizyl, quinolyl, isoquinolyl, cinnolinyl, phthalazinyl, quinazolizinyl, quinoxalyl, naphthyridinyl, and pteridyl. Bicyclic heteroaryls are numbered according to standard chemical nomenclature.

The term "heterocycloalkyl" as used herein refers to an aliphatic, partially unsaturated or fully saturated, 3- to 14-membered ring system, including single rings of 3 to 8 atoms and bi- and tricyclic ring systems where at least one of the carbon atoms of the ring is replaced with a heteroatom such as, but not limited to, nitrogen, oxygen, sulfur, or phosphorus. A heterocycloalkyl can include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited, to the following exemplary groups: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The term heterocycloalkyl group can also be a C2 heterocycloalkyl, C2-C3 heterocycloalkyl, C2-C4 heterocycloalkyl, C2-C5 heterocycloalkyl, C2-C6 heterocycloalkyl, C2-C7 heterocycloalkyl, C2-C8 heterocycloalkyl, C2-C9 heterocycloalkyl, C2-C10 heterocycloalkyl, C2-C11 heterocycloalkyl, and the like up to and including a C2-C14 heterocycloalkyl. For example, a C2 heterocycloalkyl comprises a group which has two carbon atoms and at least one heteroatom, including, but not limited to, aziridinyl, diazetidinyl, oxiranyl, thiiranyl, and the like. Alternatively, for example, a C5 heterocycloalkyl comprises a group which has five carbon atoms and at least one heteroatom, including, but not limited to, piperidinyl, tetrahydropyranyl, tetrahydrothiopyranyl, diazepanyl, and the like. It is understood that a heterocycloalkyl group may be bound either through a heteroatom in the ring, where chemically possible, or one of carbons comprising the heterocycloalkyl ring. The heterocycloalkyl group can be substituted or unsubstituted. The heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, $S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^°$; —$(CH_2)_{0-4}OR^°$; —$O(CH_2)_{0-4}R^°$, —O—$(CH_2)_{0-4}C(O)OR^°$; —$(CH_2)_{0-4}$—$CH(OR^°)_2$; —$(CH_2)_{0-4}SR^°$; —$(CH_2)_{0-4}$Ph, which may be substituted with $R^°$; —$(CH_2)_{0-4}O(CH_2)_{0-1}$Ph which may be substituted with $R^°$; —CH=CHPh, which may be substituted with $R^°$; —$(CH_2)_{0-4}$—O—$(CH_2)_{0-1}$-pyridyl which may be substituted with $R^°$; —$NO_2$; —CN; —$N_3$; —$(CH_2)_{0-4}N(R^°)_2$; —$(CH_2)_{0-4}N(R^°)C(O)R^°$; —$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —$C(S)R^°$; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}OC(O)R^°$; —OC(O)$(CH_2)_{0-4}SR$—, —SC(S)S$R^°$; —$(CH_2)_{0-4}SC(O)R^°$; —$(CH_2)_{0-4}C(O)NR^°_2$; —C(S)$NR^°_2$; —C(S)$SR^°$; —$(CH_2)_{0-4}OC(O)NR^°_2$; —C(O)N(OR^°)R^°; —C(O)C(O)R^°; —C(O)$CH_2$C(O)R^°; —C(NOR^°)R^°; —$(CH_2)_{0-4}SSR^°$; —$(CH_2)_{0-4}S(O)_2R^°$; —$(CH_2)_{0-4}S(O)_2OR^°$, —$(CH_2)_{0-4}OS(O)_2R^°$; —S(O)$_2NR^°$; —$(CH_2)_{0-4}S(O)R^°$; —$N(R^°)S(O)_2NR^°_2$; —$N(R^°)S(O)_2R^°$; —N(OR^°)R^°; —C(NH)$NR^°_2$; —P(O)$_2R^°$; —P(O)$R^°_2$; —OP(O)$R^°_2$; —OP(O)(OR^°)$_2$; Si$R^°_3$; —$(C_{1-4}$ straight or branched alkylene)O—N(R^°)$_2$; or —$(C_{1-4}$ straight or branched alkylene)C(O)O—N(R^°)$_2$, wherein each $R^°$ may be substituted as defined below and is independently hydrogen, $C_{1-6}$ aliphatic, —$CH_2$Ph, —O$(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^°$ (or the ring formed by taking two independent occurrences of $R^°$ together with their intervening atoms), are independently halogen, —$(CH_2)_{0-2}R^{\bullet}$, -(halo$R^{\bullet}$), —$(CH_2)_{0-2}$OH, —$(CH_2)_{0-2}OR^{\bullet}$, —$(CH_2)_{0-2}$CH(O$R^{\bullet})_2$; —O(halo$R^{\bullet}$), —CN, —$N_3$, —$(CH_2)_{0-2}C(O)R^{\bullet}$, —$(CH_2)_{0-2}$C(O)OH, —$(CH_2)_{0-2}C(O)OR^{\bullet}$, —$(CH_2)_{0-2}SR^{\bullet}$, —$(CH_2)_{0-2}$SH, —$(CH_2)_{0-2}NH_2$, —$(CH_2)_{0-2}NHR^{\bullet}$, —$(CH_2)_{0-2}NR^{\bullet}_2$, —$NO_2$, —SiR^{\bullet}_3, —OSiR^{\bullet}_3, —C(O)SR^{\bullet}$, —$(C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^°$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^{\bullet}$, -(halo$R^{\bullet}$), —OH, —O$R^{\bullet}$, —O(halo$R^{\bullet}$), —CN, —C(O)OH, —C(O)O$R^{\bullet}$, —$NH_2$, —NH$R^{\bullet}$, —NR$^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —N$R^†_2$, —C(O)$R^†$, —C(O)O$R^†$, —C(O)C(O)$R^†$, —C(O)$CH_2$C(O)$R^†$, —S(O)$_2R^†$, —S(O)$_2NR^†_2$, —C(S)$NR^†_2$, —C(NH)$NR^†_2$, or —N($R^†$)S(O)$_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitatation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1-26 carbon atoms, 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2-26 carbon atoms, 2 to 18 carbon atoms, 2 to 15 carbon atoms, 2 to 12 carbon atoms, 2 to 8 carbon atoms, 2 to 6 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

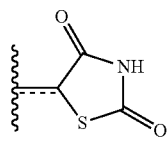

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1 to 15, carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2 to 15 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory or a compound prefixed with (+) or d meaning that the compound is dextrorotatory. For a given chemical structure, these compounds, called stereoisomers, are identical except that they are non-superimposable minor images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

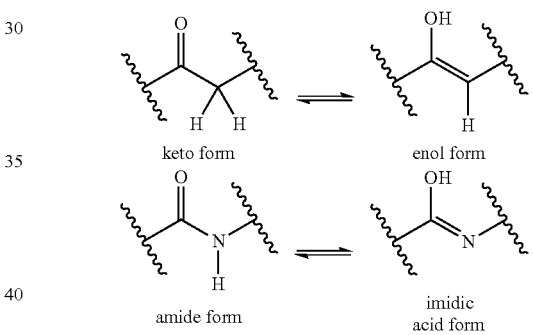

keto form     enol form amide form     imidic acid form

Likewise, amides with an N-hydrogen can exist in an equilibrium of the amide form and the imidic acid form. As another example, pyridinones can exist in two tautomeric forms, as shown below.

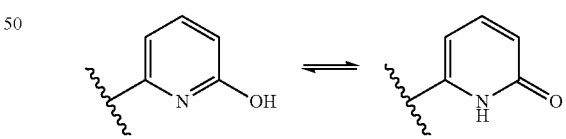

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

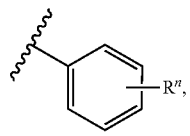

which is understood to be equivalent to a formula:

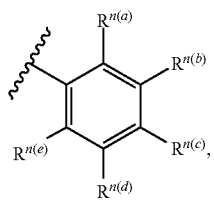

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The following abbreviations are used herein. AcOEt: ethyl acetate. AcOH: acetic acid. ACN: acetonitrile. BuOH: 1-butanol. DIPEA or DIEA: N,N-diisopropylethylamine. DMAP: 4-dimethylaminopyridine. DCM: dichloromethane. DCE: 1,2-dichloroethane. DIPE: diisopropylether. DMF: N,N-dimethyl formamide. DMSO: dimethylsulfoxide. EDC: 1-ethyl-3-[3-dimethylaminopropyl]carbodiimide hydrochloride. EtOH: ethanol. h: Hours. HPLC: high-performance liquid chromatography. HOBt: 1-hydroxybenzotriazole. iPrOH: 2-propanol. LC-MS or LCMS: liquid chromatography/mass spectrometry. [M+H]+: protonated mass of the free base of the compound. M.p.: melting point. MeOH: methanol. Min: Minutes. NMR: nuclear magnetic resonance. RP: reversed phase. Rt: retention time (in minutes). RT: Room temperature. TEA: triethylamine. THF: tetrahydrofuran. TMEDA: N,N,N'N'-tetramethylethylenediamine Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as positive allosteric modulators of the metabotropic glutamate receptor subtype 5 (mGluR5). More specifically, in one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity.

In one aspect, the disclosed compounds exhibit positive allosteric modulation of mGluR5 response to glutamate as an increase in response to non-maximal concentrations of glutamate in human embryonic kidney cells transfected with rat mGluR5 in the presence of the compound, compared to the response to glutamate in the absence of the compound. In further aspect, the human embryonic kidney cells are transfected with human mGluR5. In yet a further aspect, human embryonic kidney cells are transfected with mGluR5 of a mammal.

In one aspect, the compounds of the invention are useful in the treatment neurological and psychiatric disorders associated with glutamate dysfunction and other diseases in which metabotropic glutamate receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In various aspects, s the invention relates to a compound having a structure represented by a formula:

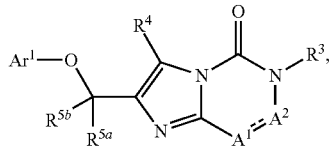

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In one aspect, the invention relates to a compound having a structure represented by a formula:

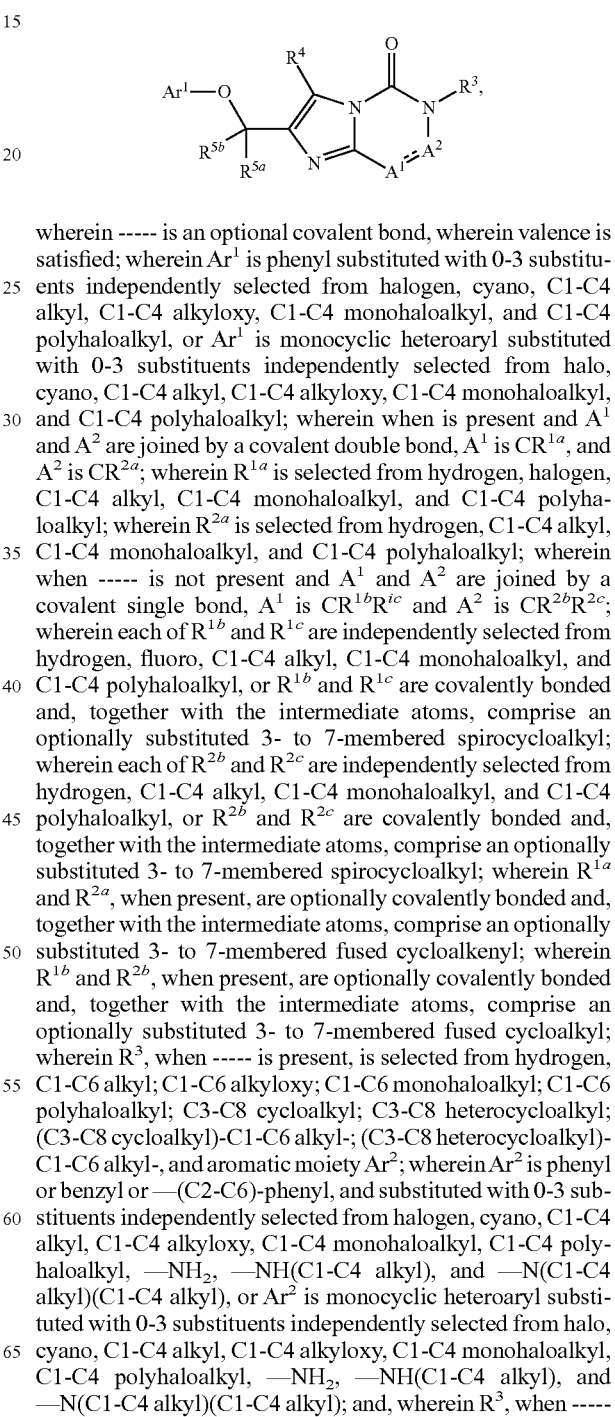

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$ and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound has a structure represented by a formula:

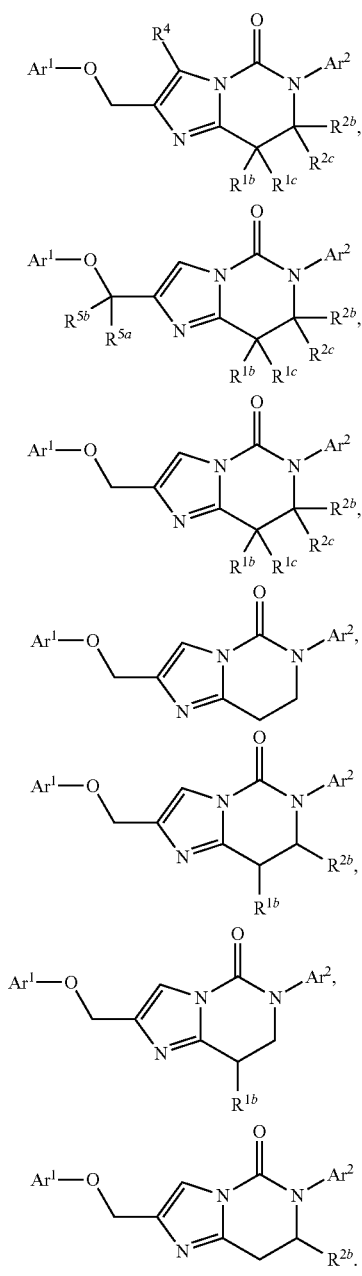

In a further aspect, the compound has a structure represented by a formula:

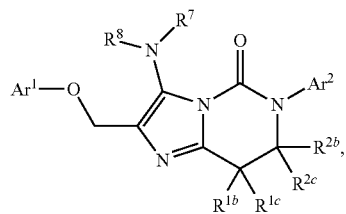

wherein $R^7$ and $R^8$ are independently selected from hydrogen and C1-C4 alkyl.

In a further aspect, the compound has a structure represented by a formula:

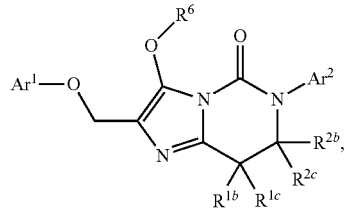

wherein $R^6$ is C1-C4 alkyl.

In a further aspect, the compound has a structure represented by a formula:

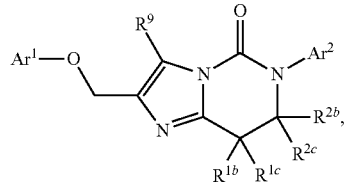

wherein $R^9$ is selected from C1-C4 alkyl, C1-C4 monohaloalkyl, and C1-C4 polyhaloalkyl.

In a further aspect, the compound has a structure represented by a formula:

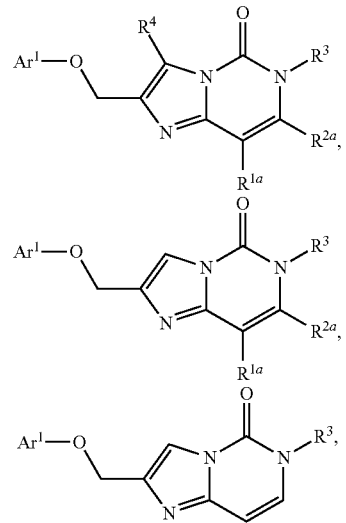

-continued

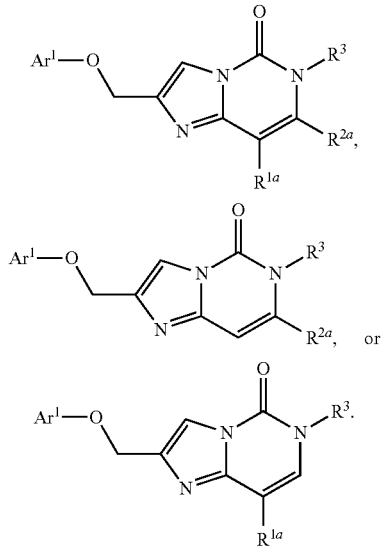

In a further aspect, the compound has a structure represented by a formula:

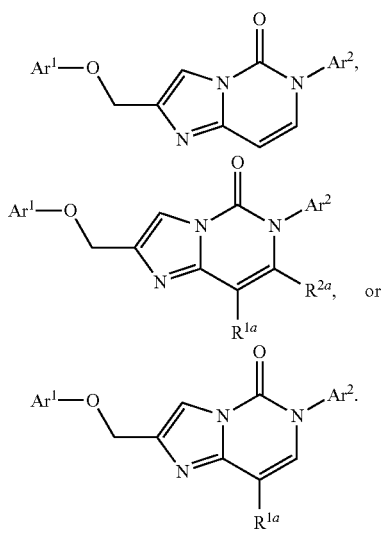

In a further aspect, the compound has a structure represented by a formula:

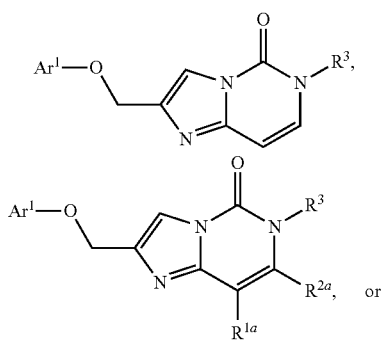

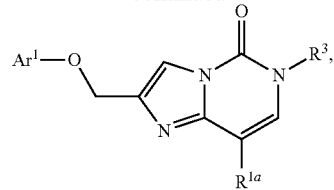

wherein $R^3$ is selected from C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; and (C3-C8 heterocycloalkyl)-C1-C6 alkyl-.

In a further aspect, the compound has a structure represented by a formula:

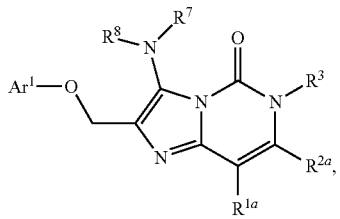

wherein $R^7$ and $R^8$ are independently selected from hydrogen and C1-C4 alkyl.

In a further aspect, the compound has a structure represented by a formula:

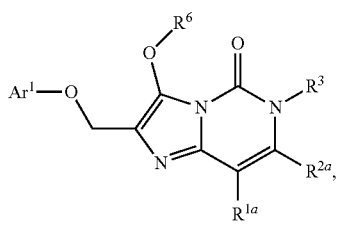

wherein $R^6$ is C1-C4 alkyl.

In a further aspect, the compound has a structure represented by a formula:

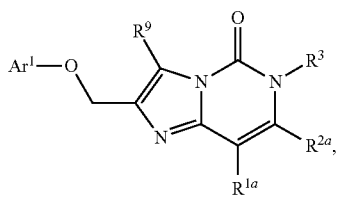

wherein $R^9$ is selected from C1-C4 alkyl, C1-C4 monohaloalkyl, and C1-C4 polyhaloalkyl.

In a further aspect, the compound has a structure represented by a formula:

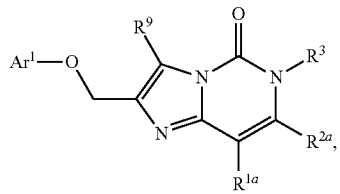

wherein $R^9$ is selected from halogen, C1-C4 alkyl, C1-C4 monohaloalkyl, and C1-C4 polyhaloalkyl.

In a further aspect, the compound has a structure represented by a formula:

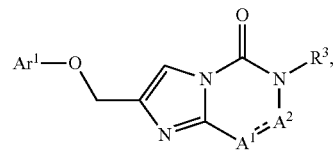

wherein ----- is an optional covalent bond, wherein valence is satisfied; wherein $Ar^1$ is phenyl or monocyclic heteroaryl; each of which may be unsubstituted or substituted with 1-3 substituents independently selected from halogen, cyano, and C1-C4 alkyl; wherein when ----- is present and $A^1$ and $A^2$ are joined by a covalent double bond, wherein $A^1$ is $CR^{1a}$, and $A^2$ is $CR^{2a}$; wherein $R^{1a}$ and $R^{2a}$ are each selected from hydrogen and halogen; wherein when is not present and $A^1$ and $A^2$ are joined by a covalent single bond, wherein $A^1$ is $CH_2$, and $A^2$ is $CH_2$; wherein $R^3$, when ----- is present, is selected from $Ar^2$ and $(Ar^2)$—C1-C4 alkyl; wherein $Ar^2$ is phenyl, which may be unsubstituted or substituted with 1-3 substituents independently selected from halogen, cyano and C1-C4 alkyl; or $Ar^2$ is monocyclic heteroaryl, which may be unsubstituted or substituted with 1-3 substituents independently selected from halogen, C1-C4 alkyl, C1-C4 alkyoxy, and mono- or di-C1-C4-alkylamino; wherein $R^3$, when ----- is not present, is $Ar^2$; and wherein monocyclic heteroaryl is pyridinyl, pyrimidinyl, pyridazinyl or pyrazinyl.

In a further aspect, the compound has a structure represented by a formula:

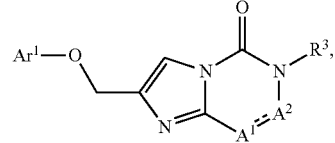

wherein ----- is an optional covalent bond, wherein valence is satisfied; wherein $Ar^1$ is phenyl, which may be unsubstituted or substituted with 1-3 substituents independently selected from halogen, cyano and C1-C4 alkyl; wherein when ----- is present and $A^1$ and $A^2$ are joined by a covalent double bond, wherein $A^1$ is $CR^{1a}$, and $A^2$ is $CR^{2a}$; wherein $R^{1a}$ is selected from hydrogen and halogen and $R^{2a}$ is hydrogen; wherein when ----- is not present and $A^1$ and $A^2$ are joined by a covalent single bond, wherein $A^1$ is $CH_2$, and $A^2$ is $CH_2$; wherein $R^3$, when ----- is present, is selected from phenyl or benzyl, wherein each of which may be unsubstituted or substituted at the phenyl moiety with 1-3 independently selected halogen substituents; or pyridinyl, which may be unsubstituted or substituted with 1-3 substituents independently selected from halogen, C1-C4 alkyl, C1-C4 alkyoxy, and mono- or di-C1-C4-alkylamino; and wherein $R^3$, when ----- is not present, is phenyl, which may be unsubstituted or substituted at the phenyl moiety with 1-3 independently selected halogen substituents; or pyridinyl, which may be unsubstituted or substituted with 1-3 substituents independently selected from halogen, C1-C4 alkyl, C1-C4 alkyoxy, and mono- or di-C1-C4-alkylamino. In a further aspect, the compound has a structure represented by a formula:

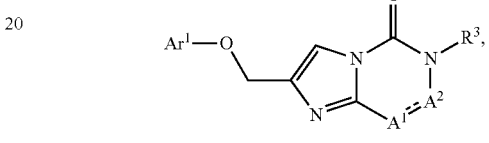

wherein ----- is an optional covalent bond, wherein valence is satisfied; wherein $Ar^1$ is phenyl, which may be unsubstituted or substituted with 1-3 independently selected halogen substituents; wherein when ----- is present and $A^1$ and $A^2$ are joined by a covalent double bond, wherein $A^1$ and $A^2$ are each CH; wherein when ----- is not present and $A^1$ and $A^2$ are joined by a covalent single bond, wherein $A^1$ and $A^2$ are each $CH_2$; wherein $R^3$, when is present, is selected from phenyl or pyridinyl, each of which may be unsubstituted or substituted with 1-3 independently selected halogen substituents; and wherein $R^3$, when ----- is not present, is phenyl or pyridinyl, each of which may be unsubstituted or substituted with 1-3 independently selected halogen substituents.

In a further aspect, the compound has a structure represented by a formula:

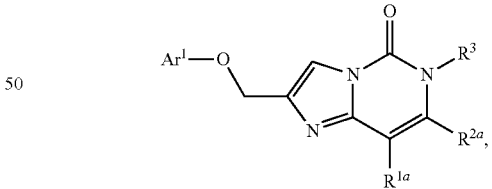

wherein $Ar^1$ is phenyl or monocyclic heteroaryl; each of which may be unsubstituted or substituted with 1-3 substituents independently selected from halogen, cyano, and C1-C4 alkyl; wherein $R^{1a}$ and $R^{2a}$ are each selected from hydrogen and halogen; and wherein $R^3$ is selected from $Ar^2$ and $(Ar^2)$—C1-C4 alkyl; wherein $Ar^2$ is phenyl, which may be unsubstituted or substituted with 1-3 substituents independently selected from halogen, cyano and C1-C4 alkyl; or $Ar^2$ is monocyclic heteroaryl, which may be unsubstituted or substituted with 1-3 substituents independently selected from halogen, C1-C4 alkyl, C1-C4 alkyoxy, and mono- or di-C1-C4-alkylamino.

In a further aspect, the compound has a structure represented by a formula:

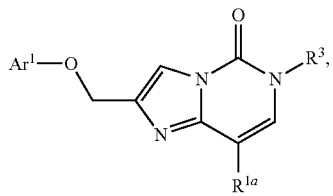

wherein $Ar^1$ is phenyl, which may be unsubstituted or substituted with 1-3 substituents independently selected from halogen, cyano and C1-C4 alkyl; wherein $R^{1a}$ is selected from hydrogen and halogen; and wherein $R^3$ is selected from phenyl or benzyl, wherein each of which may be unsubstituted or substituted at the phenyl or benzyl moiety with 1-3 independently selected halogen substituents; or pyridinyl, which may be unsubstituted or substituted with 1-3 substituents independently selected from halogen, C1-C4 alkyl, C1-C4 alkyoxy, and mono- or di-C1-C4-alkylamino.

In a further aspect, the compound has a structure represented by a formula:

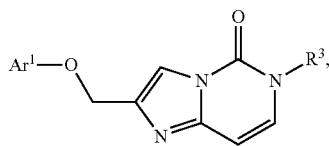

wherein $Ar^1$ is phenyl, which may be unsubstituted or substituted with 1-3 independently selected halogen substituents; and wherein $R^3$ is selected from phenyl or pyridinyl, each of which may be unsubstituted or substituted with 1-3 independently selected halogen substituents.

In a further aspect, the compound has a structure represented by a formula:

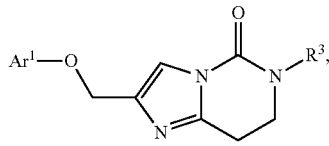

wherein $Ar^1$ is phenyl or monocyclic heteroaryl; each of which may be unsubstituted or substituted with 1-3 substituents independently selected from halogen, cyano, and C1-C4 alkyl; wherein $R^3$ is $Ar^2$; wherein monocyclic heteroaryl is pyridinyl, pyrimidinyl, pyridazinyl or pyrazinyl; and wherein all other variables are as defined herein.

In a further aspect, the compound has a structure represented by a formula:

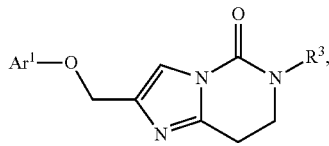

wherein $Ar^1$ is phenyl, which may be unsubstituted or substituted with 1-3 substituents independently selected from halogen, cyano and C1-C4 alkyl; and wherein $R^3$ is phenyl, which may be unsubstituted or substituted at the phenyl moiety with 1-3 independently selected halogen substituents; or pyridinyl, which may be unsubstituted or substituted with 1-3 substituents independently selected from halogen, C1-C4 alkyl, C1-C4 alkyoxy, and mono- or di-C1-C4-alkylamino.

In a further aspect, the compound has a structure represented by a formula:

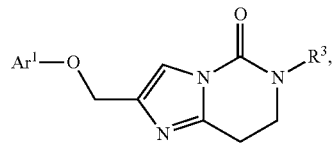

wherein $Ar^1$ is phenyl, which may be unsubstituted or substituted with 1-3 independently selected halogen substituents; and wherein $R^3$ is phenyl or pyridinyl, each of which may be unsubstituted or substituted with 1-3 independently selected halogen substituents.

Suitable substituents are described below.

a. Optional Covalent Bond

In various aspects, ----- is an optional covalent bond, wherein valence is satisfied.

In a further aspect, ----- is present as a covalent bond, thereby joining $A^1$ and $A^2$ with a covalent double bond. In a further aspect, ----- is present, and $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl.

In a further aspect, ----- is present, and $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$.

In a further aspect, ----- is not present, thereby joining $A^1$ and $A^2$ with a covalent single bond. In a further aspect, ----- is not present, and $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2a}$ are covalently bonded and, together with the intermediate atoms, comprise an optionally substituted 3- to 7-membered spirocycloalkyl;

In a further aspect, ----- is not present, and $R^3$ is $Ar^2$;

b. A Groups

In one aspect, when ----- is present, $A^1$ and $A^2$ are joined by a covalent double bond, $A^1$ is $CR^{1a}$ and $A^2$ is $CR^{2a}$. Thus, in a further aspect, the portion of the compound comprising $A^1$ and $A^2$ can have a structure represented by a formula:

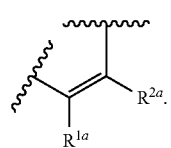

In one aspect, when ----- is not present, $A^1$ and $A^2$ are joined by a covalent single bond, $A^1$ is $CR^{1b}R^{1c}$, and $A^2$ is $CR^{2b}R^{2c}$. Thus, in a further aspect, the portion of the compound comprising $A^1$ and $A^2$ can have a structure represented by a formula:

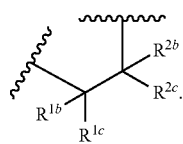

c. $Ar^1$ Groups

In one aspect, $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl.

In a further aspect, $Ar^1$ is unsubstituted. In a still further aspect, $Ar^1$ has 1, 2, or 3 substituents. In a yet further aspect, $Ar^1$ is phenyl. In an even further aspect, $Ar^1$ is phenyl with 1-3 substituents independently selected from halogen, cyano, C1-C4 alkyl, C1-C4 alkyloxy, C1-C4 monohaloalkyl, and C1-C4 polyhaloalkyl.

In a further aspect, $Ar^1$ is heteroaryl. In a still further aspect, $Ar^1$ is pyridinyl, pyridazinyl, pyrimidinyl, or pyrazinyl. In a yet further aspect, $Ar^1$ is pyridinyl, pyridazinyl, pyrimidinyl, or pyrazinyl and has 1-3 substituents independently selected from halogen, cyano, C1-C4 alkyl, C1-C4 alkyloxy, C1-C4 monohaloalkyl, and C1-C4 polyhaloalkyl.

In a further aspect, $Ar^1$ is substituted with 1-3 groups independently selected from halogen, cyano, C1-C4 alkyl, C1-C4 alkyloxy, C1-C4 monohaloalkyl, and C1-C4 polyhaloalkyl. In a yet further aspect, $Ar^1$ is substituted with 1-3 groups selected from halogen, cyano, C1-C4 alkyl, and C1-C4 alkyloxy. In an even further aspect, $Ar^1$ is substituted with 1-3 groups selected from halogen, methyl, trifluoromethyl, ethyl, propyl, and butyl. In a further aspect, $Ar^1$ is substituted with 1-3 groups selected from methoxy, trifluoromethoxy, ethoxy, propyloxy, or butyloxy. In a still further aspect, $Ar^1$ is substituted with 1-3 cyano groups. In a yet further aspect, $Ar^1$ is substituted with 1-3 groups selected from halogen, cyano, methyl, and trifluoromethyl.

In a further aspect, $Ar^1$ is substituted with 0-3 halogens. In a still further aspect, $Ar^1$ is substituted with 1-3 halogens.

d. $Ar^2$ Groups

In one aspect, $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH (C1-C4 alkyl), and —N(C1-C4 alkyl)(C1-C4 alkyl), or $Ar^2$ is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is unsubstituted. In a still further aspect, $Ar^2$ has 1, 2, or 3 substituents.

In a further aspect, $Ar^2$ is phenyl. In an even further aspect, $Ar^2$ is phenyl with 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is phenyl with 1-3 substituents selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is benzyl. In a yet further aspect, $Ar^2$ is benzyl with 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is benzyl with 1-3 substituents selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is —(C2-C6)-phenyl. In a yet further aspect, $Ar^2$ is —(C2-C6)-phenyl with 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is —(C2-C6)-phenyl with 1-3 substituents selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl) (C1-C4 alkyl).

In a further aspect, $Ar^2$ is heteroaryl. In a still further aspect, $Ar^2$ is pyridinyl, pyridazinyl, pyrimidinyl, or pyrazinyl. In a yet further aspect, $Ar^2$ is pyridinyl, pyridazinyl, pyrimidinyl, or pyrazinyl and has 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is pyridinyl, pyridazinyl, pyrimidinyl, or pyrazinyl and has 1-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a still further aspect, $Ar^2$ is pyridinyl. In a yet further aspect, $Ar^2$ is pyridinyl and has 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is pyridinyl and has 1-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is pyridazinyl. In a yet further aspect, $Ar^2$ is pyridazinyl and has 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is pyridazinyl and has 1-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is pyrimidinyl. In a yet further aspect, $Ar^2$ is pyrimidinyl and has 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is pyrimidinyl and has 1-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is pyrazinyl. In a yet further aspect, $Ar^2$ is pyrazinyl and has 1-3 substituents independently selected from halogen, cyano, C1-C4 alkyl, C1-C4 alkyloxy, C1-C4 monohaloalkyl, and C1-C4 polyhaloalkyl. In a still further aspect, $Ar^2$ is pyrazinyl and has 1-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl).

In a further aspect, $Ar^2$ is substituted with 1-3 groups independently selected from halogen, cyano, C1-C4 alkyl, C1-C4 alkyloxy, C1-C4 monohaloalkyl, and C1-C4 polyhaloalkyl. In a yet further aspect, $Ar^2$ is substituted with 1-3 groups selected from halogen, cyano, C1-C4 alkyl, and C1-C4 alkyloxy. In an even further aspect, $Ar^2$ is substituted with 1-3 groups selected from halogen, methyl, trifluoromethyl, ethyl, propyl, and butyl. In a further aspect, $Ar^2$ is substituted with 1-3 groups selected from methoxy, trifluoromethoxy, ethoxy, propyloxy, or butyloxy. In a still further aspect, $Ar^2$ is substituted with 1-3 groups selected from methyl, fluoro, trifluoromethyl, methoxy, and —N(CH$_3$)$_2$.

In a further aspect, $Ar^2$ is substituted with 0-3 halogens. In a still further aspect, $Ar^2$ is substituted with 1-3 halogens. In a yet further aspect, $Ar^2$ is substituted with 0-3 fluoro groups. In an even further aspect, $Ar^2$ is substituted with 1-3 fluoro groups.

e. $R^{1a}$ Groups

In one aspect, when ----- is present, $R^{1a}$ is selected from hydrogen, halogen, C1-C4 alkyl, C1-C4 monohaloalkyl, and C1-C4 polyhaloalkyl. In a further aspect, $R^{1a}$, when present, is hydrogen. In a yet further aspect, $R^{1a}$, when present, is selected from hydrogen and halogen. In an even further aspect, $R^{1a}$, when present, is selected from hydrogen, fluoro, and chloro. In a still further aspect, $R^{1a}$, when present, is selected from hydrogen, fluoro, iodo and chloro. In a still further aspect, $R^{1a}$, when present, is selected from hydrogen, fluoro, and iodo.

In a further aspect, $R^{1a}$, when present, is C1-C4 alkyl. In a still further aspect, $R^{1a}$, when present, is selected from hydrogen, halogen, methyl, trifluoromethyl, ethyl, propyl, and butyl. In a yet further aspect, $R^{1a}$, when present, is selected from hydrogen, fluoro, chloro, methyl, trifluoromethyl, ethyl, propyl, and butyl. In an even further aspect, $R^{1a}$, when present, is selected from hydrogen, fluoro, methyl, trifluoromethyl, ethyl, propyl, and butyl. In a still further aspect, $R^{1a}$, when present, is selected from hydrogen, fluoro, chloro, iodo, methyl, trifluoromethyl, ethyl, propyl, and butyl. In an even further aspect, $R^{1a}$, when present, is selected from hydrogen, fluoro, iodo, methyl, trifluoromethyl, ethyl, propyl, and butyl.

In further aspect, $R^{1a}$, when present, is selected from hydrogen, methyl, trifluoromethyl, ethyl, propyl, and butyl. In a still further aspect, $R^{1a}$, when present, is selected methyl, trifluoromethyl, ethyl, propyl, and butyl.

In a further aspect, $R^{1a}$, when present, is selected halogen, methyl, trifluoromethyl, ethyl, propyl, and butyl. In a yet further aspect, $R^{1a}$, when present, is selected from fluoro, chloro, methyl, trifluoromethyl, ethyl, propyl, and butyl. In an even further aspect, $R^{1a}$, when present, is selected from fluoro, methyl, trifluoromethyl, ethyl, propyl, and butyl. In a still further aspect, $R^{1a}$, when present, is selected from fluoro, chloro, iodo, methyl, trifluoromethyl, ethyl, propyl, and butyl. In an even further aspect, $R^{1a}$, when present, is selected from fluoro, iodo, methyl, trifluoromethyl, ethyl, propyl, and butyl.

In a further aspect, $R^{1a}$ and $R^{2a}$, when present, are optionally covalently bonded and, together with the intermediate atoms, comprise an optionally substituted 3- to 7-membered fused cycloalkyl. In a still further aspect, $R^{1a}$ and $R^{2a}$ are directly covalently bonded to comprise, together with the intermediate atoms, a 3-, 4-, 5-, 6-, or 7-membered fused cycloalkyl. In a yet further aspect, $R^{1a}$ and $R^{2a}$ are directly covalently bonded to comprise, together with the intermediate atoms, a substituted 3-, 4-, 5-, 6-, or 7-membered fused cycloalkyl. In an even further aspect, $R^{1a}$ and $R^{2a}$ are directly covalently bonded to comprise, together with the intermediate atoms, a substituted 3-, 4-, 5-, 6-, or 7-membered fused cycloalkyl, and the fused cycloalkyl is substituted with 1 or 2 groups selected from methyl, ethyl, and propyl.

In a further aspect, $R^{1a}$ and $R^{2a}$ are not directly covalently bonded. In a yet further aspect, $R^{1a}$ and $R^{2a}$, when present, are each hydrogen. In a still further aspect, $R^{1a}$ and $R^{2a}$, when present, are each methyl. In an even further aspect, of $R^{1a}$ and $R^{2a}$, when present, are independently selected from each hydrogen, methyl, and trifluoromethyl.

f. $R^{1b}$ and $R^{1c}$ Groups

In one aspect, when ----- is not present, each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl. In a still further aspect, $R^{1b}$ and $R^{1c}$ when present, are each hydrogen. In a yet further aspect, $R^{1b}$ and $R^{1c}$, when present, are each C1-C4 alkyl. In an even further aspect, each of $R^{1b}$ and $R^{1c}$ when present, are independently selected from hydrogen and C1-C4 alkyl.

In a further aspect, each of $R^{1b}$ and $R^{1c}$ when present, are independently selected from hydrogen and fluoro. In a yet further aspect, each of $R^{1b}$ and $R^{1c}$ when present, are independently selected from fluoro, C1-C4 alkyl, C1-C4 monohaloalkyl, and C1-C4 polyhaloalkyl. In an even further aspect, each of $R^{1b}$ and $R^{1c}$ when present, are independently selected hydrogen fluoro, methyl, trifluoromethyl, ethyl, propyl, and butyl.

In a further aspect, $R^{1b}$ and $R^{1c}$ when present, are independently selected from hydrogen, C1-C4 alkyl, C1-C4 monohaloalkyl, and C1-C4 polyhaloalkyl. In a still further aspect, $R^{1b}$ and $R^{1c}$ when present, are independently selected from hydrogen, methyl, trifluoromethyl, ethyl, propyl, and butyl.

In a further aspect, $R^{1b}$ and $R^{2b}$, when present, are optionally covalently bonded and, together with the intermediate atoms, comprise an optionally substituted 3- to 7-membered fused cycloalkyl. In a still further aspect, $R^{1b}$ and $R^{1c}$ are covalently bonded and, together with the intermediate carbon, comprise a 3- to 7-membered spirocycloalkyl. In a yet further aspect, $R^{1b}$ and $R^{1c}$ are covalently bonded and, together with the intermediate carbon, comprise a substituted 3- to 7-membered spirocycloalkyl. In an even further aspect, $R^{1b}$ and $R^{1c}$ are covalently bonded and, together with the intermediate carbon, comprise a substituted 3- to 7-membered spirocycloalkyl, and the spirocycloalkyl is substituted with 1 or 2 groups selected from methyl, ethyl, and propyl.

g. $R^{2a}$ Groups

In one aspect, when ----- is present, $R^{2a}$ is selected from hydrogen, C1-C4 alkyl, C1-C4 monohaloalkyl, and C1-C4 polyhaloalkyl. In a further aspect, $R^{2a}$, when present, is hydrogen. In a yet further aspect, $R^{2a}$, when present, is methyl. In an even further aspect, $R^{2a}$, when present, is C1-C4 alkyl. In a further aspect, $R^{2a}$, when present, is selected from methyl, trifluoromethyl, ethyl, propyl, and butyl. In a still further aspect, $R^{2a}$, when present, is selected from hydrogen and methyl.

h. $R^{2b}$ and $R^{2c}$ Groups

In one aspect, when ----- is not present, each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl. In a further aspect, each of $R^{2b}$ and $R^{2c}$, when present, are each hydrogen. In a still further aspect, each of $R^{2b}$ and $R^{2c}$, when present, are each C1-C4 alkyl.

In a further aspect, each of $R^{2b}$ and $R^{2c}$, when present, are independently selected from hydrogen and C1-C4 alkyl. In a yet further aspect, each of $R^{2b}$ and $R^{2c}$, when present, are independently selected from hydrogen, methyl, trifluoromethyl, ethyl, propyl, and butyl. In a still further aspect, wherein each of $R^{2b}$ and $R^{2c}$, when present, are independently selected from hydrogen, methyl, and trifluoromethyl. In an even further aspect, wherein each of $R^{2b}$ and $R^{2c}$, when present, are independently selected from hydrogen and methyl.

In a further aspect, $R^{2b}$ and $R^{2c}$ are covalently bonded and, together with the intermediate carbon, comprise a 3- to 7-membered spirocycloalkyl. In a still further aspect, $R^{2b}$ and $R^{2c}$ are covalently bonded and, together with the intermediate carbon, comprise a substituted 3- to 7-membered spirocycloalkyl. In a yet further aspect, $R^{2b}$ and $R^{2c}$ are covalently bonded and, together with the intermediate carbon, comprise a substituted 3- to 7-membered spirocycloalkyl, and the spirocycloalkyl is substituted with 1 or 2 groups selected from methyl, ethyl, and propyl.

i. $R^3$ Groups

In one aspect, $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$.

In one aspect, $R^3$, when ----- is not present, is $Ar^2$.

In a further aspect, $R^3$, when ----- is present, is hydrogen. In a still further aspect, $R^3$, when ----- is present, is selected from hydrogen and C1-C6 alkyl. In an even further aspect, $R^3$, when ----- is present, is selected from methyl, trifluoromethyl, ethyl, propyl, butyl, pentyl, and hexyl.

In a further aspect, $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; and (C3-C8 heterocycloalkyl)-C1-C6 alkyl-. In a still further aspect, $R^3$, when ----- is present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclobutyl, cyclopentyl, cyclohexyl, cyclopropylmethyl, cyclobutylmethyl, cyclopentylmethyl, cyclohexylmethyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, and —$OCH(CH_2CH_3)(CH_3)$. In a yet further aspect, $R^3$, when ----- is present, is selected from hydrogen, methyl, ethyl, propyl, isopropyl, cyclopropyl, cyclobutyl, cyclopentyl, cyclohexyl, cyclopropylmethyl, cyclobutylmethyl, cyclopentylmethyl, cyclohexylmethyl, —$CH_2F$, —$CH_2Cl$, —$CH_2Br$, —$CH_2I$, —$CF_3$, —$CHCl_2$, —$CCl_3$, —$CHBr_2$, —$CBr_3$, —$CHI_2$, —$CI_3$, and —$OCH_3$. In a yet further aspect, hydrogen, methyl, cyclopropyl, cyclopropylmethyl, —$CH_2F$, —$CH_2Cl$, —$CH_2Br$, —$CH_2I$, —$CF_3$, —$CHCl_2$, —$CCl_3$, —$CHBr_2$, —$CBr_3$, —$CHI_2$, —$CI_3$, and —$OCH_3$. In an even further aspect, hydrogen, methyl, cyclopropyl, cyclopropylmethyl, —$CH_2F$, —$CHF_2$, —$CF_3$, and —$OCH_3$.

In a further aspect, $R^3$, when ----- is present, is selected from hydrogen, C1-C6 alkyl; C3-C8 cycloalkyl; and (C3-C8 cycloalkyl)-C1-C6 alkyl-. In a still further aspect, $R^3$, when ----- is present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclobutyl, cyclopentyl, cyclohexyl, cyclopropylmethyl, cyclobutylmethyl, cyclopentylmethyl, and cyclohexylmethyl. In a yet further aspect, $R^3$, when is present, is selected from hydrogen, methyl, ethyl, propyl, isopropyl, cyclopropyl, cyclobutyl, cyclopentyl, cyclohexyl, cyclopropylmethyl, cyclobutylmethyl, cyclopentylmethyl, and cyclohexylmethyl. In an even further aspect, $R^3$, when ----- is present, is selected from hydrogen, methyl, cyclopropyl, and cyclopropylmethyl. In a still further aspect, $R^3$, when ----- is present, is selected from methyl, cyclopropyl, and cyclopropylmethyl. In a yet further aspect, $R^3$, when ----- is present, is selected from hydrogen, cyclopropyl, and cyclopropylmethyl. In an even further aspect, $R^3$, when ----- is present, is selected from cyclopropyl and cyclopropylmethyl. In a still further aspect, $R^3$, when ----- is present, is cyclopropyl. In a yet further aspect, $R^3$, when ----- is present, is cyclopropylmethyl.

In a further aspect, $R^3$, when ----- is present, is phenyl. In a still further aspect, $R^3$, when ----- is present, is phenyl with 1-3 substituents selected from halogen, cyano, C1-C4 alkyl, C1-C4 alkyloxy, monohalo C1-C4 alkyl, and polyhalo C1-C4 alkyl. In a yet further aspect, $R^3$, when ----- is present, is monocyclic heteroaryl. In an even further aspect, $R^3$, when ----- is present, is pyridinyl, pyridazinyl, pyrimidinyl, or pyrazinyl. In a further aspect, $R^3$, when ----- is present, is pyridinyl, pyridazinyl, pyrimidinyl, or pyrazinyl; with 1-3 substituents selected from halogen, cyano, C1-C4 alkyl, C1-C4 alkyloxy, C1-C4 monohaloalkyl, and C1-C4 polyhaloalkyl.

In a further aspect, $R^3$, when ----- is not present, is phenyl. In a still further aspect, $R^3$, when ----- is not present, is phenyl with 1-3 substituents selected from halogen, cyano, C1-C4 alkyl, C1-C4 alkyloxy, monohalo C1-C4 alkyl, and polyhalo C1-C4 alkyl. In a yet further aspect, $R^3$, when ----- is not present, is monocyclic heteroaryl. In an even further aspect, $R^3$, when ----- is not present, is pyridinyl, pyridazinyl, pyrimidinyl, or pyrazinyl. In a further aspect, $R^3$, when ----- is not present, is pyridinyl, pyridazinyl, pyrimidinyl, or pyrazinyl; with 1-3 substituents selected from halogen, cyano, C1-C4 alkyl, C1-C4 alkyloxy, C1-C4 monohaloalkyl, and C1-C4 polyhaloalkyl.

In a further aspect, $R^3$ is phenyl. In a still further aspect, $R^3$ is phenyl with 1-3 substituents selected from halogen, cyano, C1-C4 alkyl, C1-C4 alkyloxy, monohalo C1-C4 alkyl, and polyhalo C1-C4 alkyl. In a yet further aspect, $R^3$ is monocyclic heteroaryl. In an even further aspect, $R^3$ is pyridinyl, pyridazinyl, pyrimidinyl, or pyrazinyl. In a further aspect, $R^3$ is pyridinyl, pyridazinyl, pyrimidinyl, or pyrazinyl; with 1-3 substituents selected from halogen, cyano, C1-C4 alkyl, C1-C4 alkyloxy, C1-C4 monohaloalkyl, and C1-C4 polyhaloalkyl.

j. $R^4$ Groups

In one aspect, $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy. In a further aspect, $R^4$ is hydrogen. In a yet further aspect, $R^4$ is selected from hydrogen and C1-C4 alkyl. In a still further aspect, $R^4$ is C1-C4 alkoxy.

In a further aspect, $R^4$ is selected from halogen, cyano, and C1-C4 alkyl. In a still further aspect, wherein $R^4$ is selected from C1-C4 alkylamino and C1-C4 dialkylamino. In a yet further aspect, $R^4$ is selected from C1-C4 alkyl, C1-C4 monohaloalkyl, and C1-C4 polyhaloalkyl.

In a further aspect, $R^4$ is selected from hydrogen and halogen. In a yet further aspect, $R^4$ is selected from hydrogen, fluoro, chloro, and iodo. In a still further aspect, $R^4$ is selected from hydrogen, fluoro, chloro, and bromo. In an even further aspect, In a yet further aspect, $R^4$ is selected from hydrogen, bromo, and iodo.

k. $R^{5a}$ and $R^{5b}$ Groups

In one aspect, each of $R^{5a}$ and $R^{5b}$ is independently selected from hydrogen, C1-C4 alkyl, C1-C4 monohaloalkyl, and C1-C4 polyhaloalkyl. In a further aspect, $R^{5a}$ and $R^{5b}$ are both hydrogen. In a still further aspect, one of $R^{5a}$ and $R^{5b}$ is hydrogen and the other is C1-C4 alkyl.

l. $R^6$ Groups

In one aspect, $R^6$ is C1-C4 alkyl. In a further aspect, $R^6$ is selected from methyl, ethyl, propyl, isopropyl, butyl, isobutyl, sec-butyl, and tert-butyl. In a yet further aspect, $R^6$ is selected from methyl, ethyl, propyl, and isopropyl. In a still further aspect, $R^6$ is selected from methyl and ethyl. In an even further aspect, $R^6$ is methyl. In a still further aspect, $R^6$ is ethyl.

m. $R^7$ Groups

In one aspect, $R^7$ is selected from hydrogen and C1-C4 alkyl. In a further aspect, $R^7$ is hydrogen. In a still further aspect, $R^7$ is selected from hydrogen, methyl, ethyl, propyl, isopropyl, butyl, isobutyl, sec-butyl, and tert-butyl. In a yet further aspect, $R^7$ is selected from hydrogen, methyl, ethyl, propyl, and isopropyl. In a still further aspect, $R^7$ is selected from hydrogen, methyl and ethyl. In an even further aspect, $R^7$ is hydrogen and methyl. In a still further aspect, $R^7$ is hydrogen and ethyl.

In a further aspect, $R^7$ is selected from methyl, ethyl, propyl, isopropyl, butyl, isobutyl, sec-butyl, and tert-butyl. In a yet further aspect, $R^7$ is selected from methyl, ethyl, propyl, and isopropyl. In a still further aspect, $R^7$ is selected from methyl and ethyl. In an even further aspect, $R^7$ is methyl. In a still further aspect, $R^7$ is ethyl.

In a further aspect, each of $R^7$ and $R^8$ is hydrogen. In a still further aspect, $R^7$ is hydrogen and $R^8$ is methyl. In a yet further aspect, $R^7$ is hydrogen and $R^8$ is ethyl. In an even further aspect, $R^7$ is methyl and $R^8$ is ethyl.

n. $R^8$ Groups

In one aspect, $R^8$ is selected from hydrogen and C1-C4 alkyl. In a further aspect, $R^8$ is hydrogen. In a still further aspect, $R^8$ is selected from hydrogen, methyl, ethyl, propyl, isopropyl, butyl, isobutyl, sec-butyl, and tert-butyl. In a yet further aspect, $R^8$ is selected from hydrogen, methyl, ethyl, propyl, and isopropyl. In a still further aspect, $R^8$ is selected from hydrogen, methyl and ethyl. In an even further aspect, $R^8$ is hydrogen and methyl. In a still further aspect, $R^8$ is hydrogen and ethyl.

In a further aspect, $R^8$ is selected from methyl, ethyl, propyl, isopropyl, butyl, isobutyl, sec-butyl, and tert-butyl. In a yet further aspect, $R^8$ is selected from methyl, ethyl, propyl, and isopropyl. In a still further aspect, $R^8$ is selected from methyl and ethyl. In an even further aspect, $R^8$ is methyl. In a still further aspect, $R^8$ is ethyl.

o. $R^9$ Groups

In one aspect, $R^9$ is selected from halogen, C1-C4 alkyl, C1-C4 monohaloalkyl, and C1-C4 polyhaloalkyl. In various further aspects, $R^9$ is selected from C1-C4 alkyl, C1-C4 monohaloalkyl, and C1-C4 polyhaloalkyl. In a further aspect, $R^9$ is hydrogen.

In one aspect, $R^9$ is selected from halogen and C1-C4 alkyl. In a still further aspect, $R^9$ is selected from halogen, methyl, ethyl, propyl, isopropyl, butyl, isobutyl, sec-butyl, and tert-butyl. In a yet further aspect, $R^9$ is selected from halogen, methyl, ethyl, propyl, and isopropyl. In a still further aspect, $R^9$ is selected from halogen, methyl and ethyl. In an even further aspect, $R^9$ is halogen and methyl. In a still further aspect, $R^9$ is halogen and ethyl.

In a further aspect, $R^9$ is selected from methyl, ethyl, propyl, isopropyl, butyl, isobutyl, sec-butyl, and tert-butyl. In a yet further aspect, $R^9$ is selected from methyl, ethyl, propyl, and isopropyl. In a still further aspect, $R^9$ is selected from methyl and ethyl. In an even further aspect, $R^9$ is methyl. In a still further aspect, $R^9$ is ethyl.

In a further aspect, $R^9$ is selected from —Cl, —Br, and —I. In a yet further aspect, $R^9$ is —Cl. In a still further aspect, $R^9$ is —Br. In an even further aspect, $R^9$ is —I.

In a further aspect, $R^9$ is halogen, methyl, ethyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, and —CH$_2$CI$_3$. In a still further aspect, $R^9$ is halogen, methyl, —CH$_2$F, —CH$_2$Cl, —CH$_2$Br, —CH$_2$I, —CHF$_2$, —CF$_3$, —CHCl$_2$, —CCl$_3$, —CHBr$_2$, —CBr$_3$, —CHI$_2$, and —O$_3$.

p. Halogen (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

It is also contemplated that pseudohalogens (e.g. triflate, mesylate, brosylate, etc.) can be used as leaving groups in place of halogens in certain aspects.

2. Example Compounds

In one aspect, a compound can be present as:

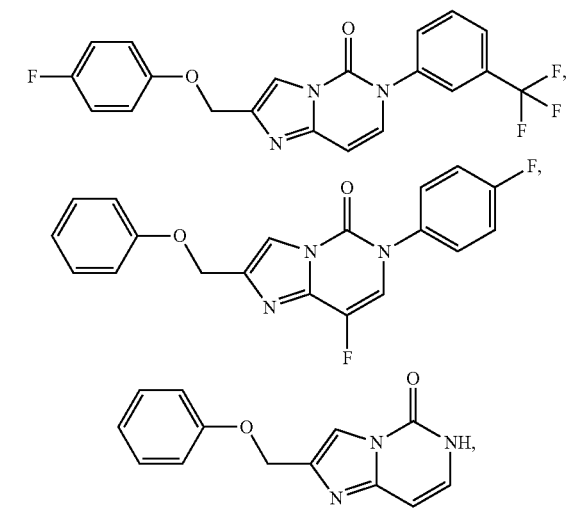

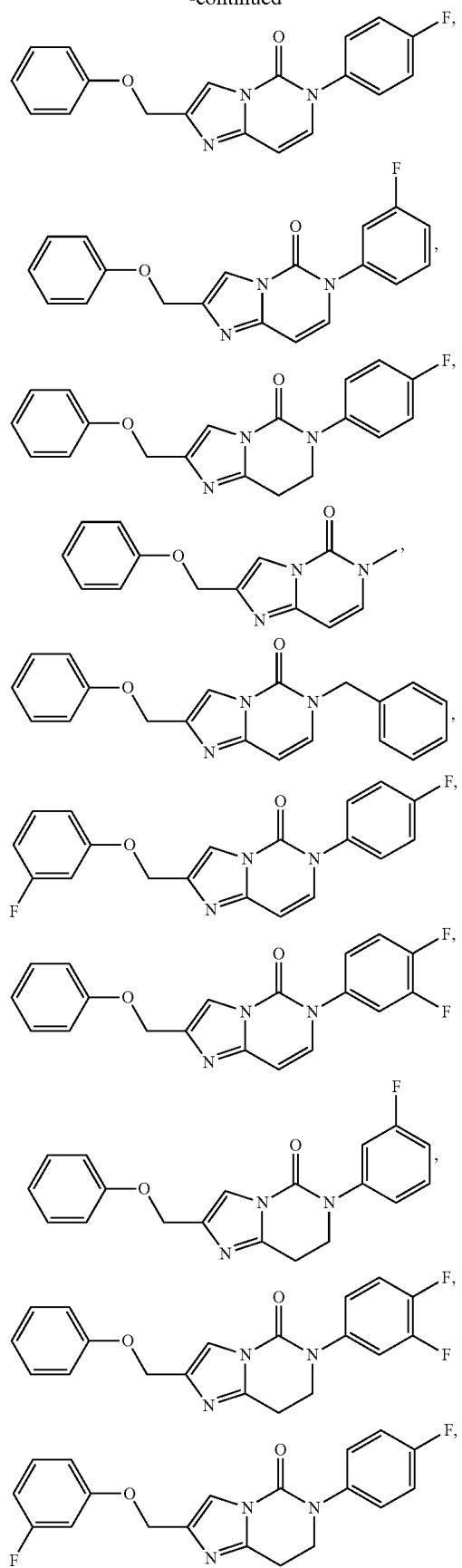
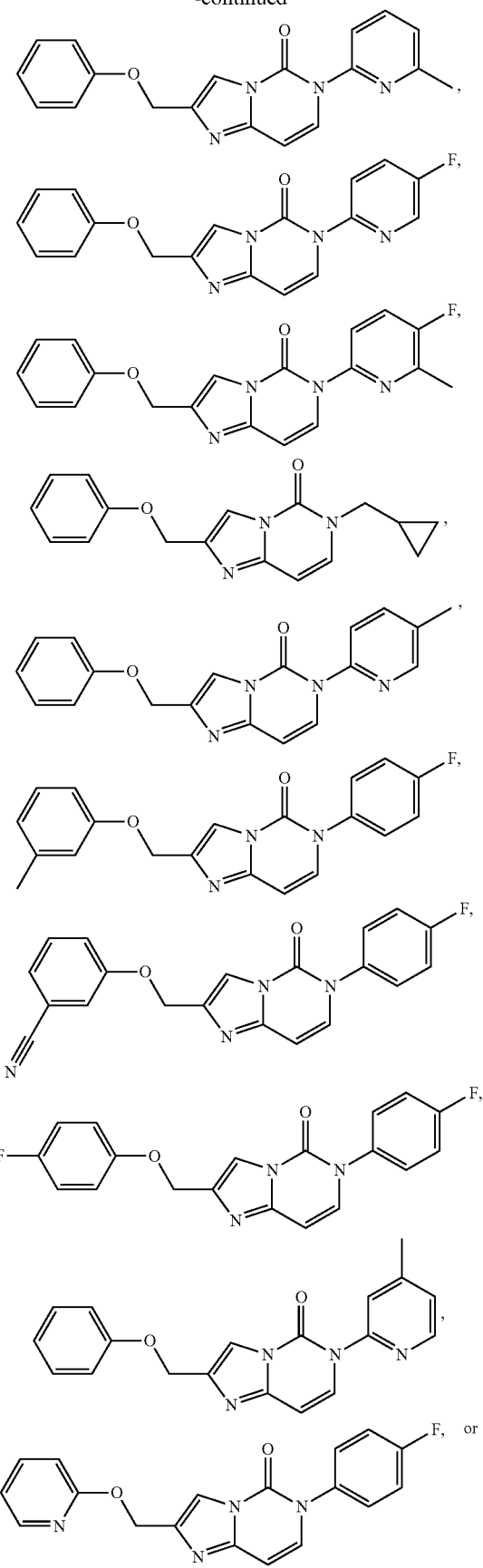

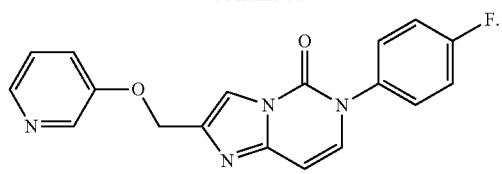
In one aspect, a compound can be present as:
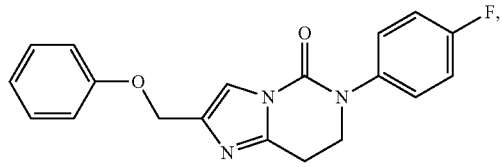
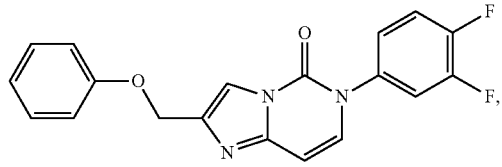
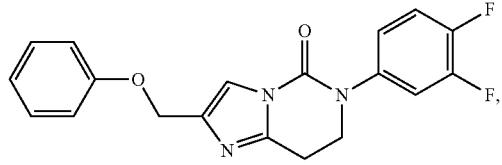
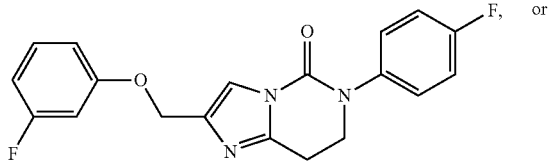 or
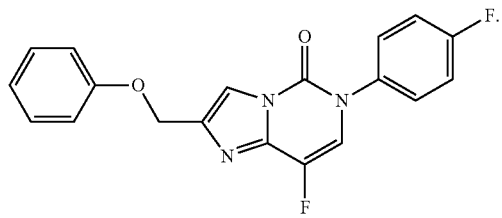
In one aspect, a compound can be present as:
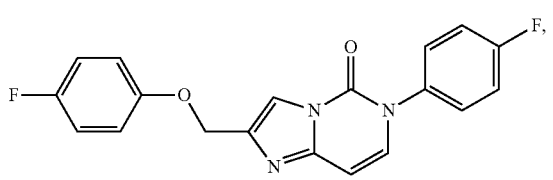
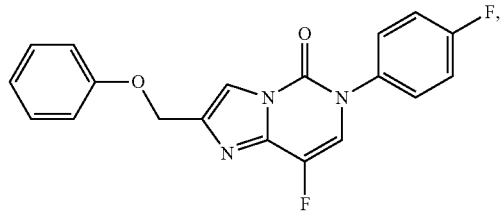
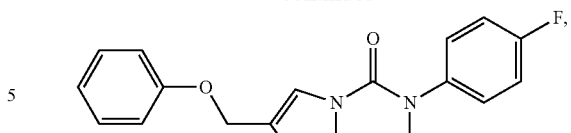
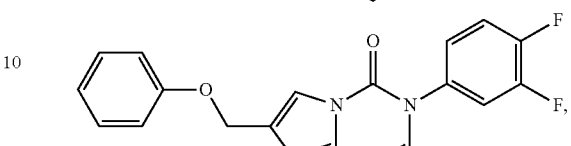
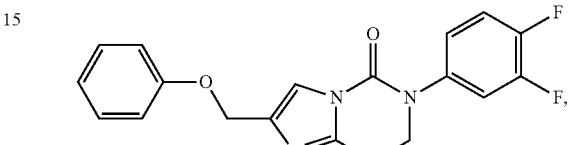
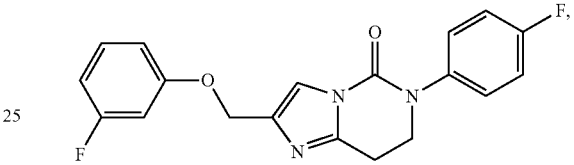
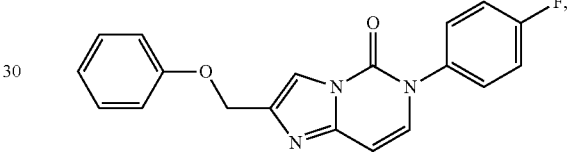
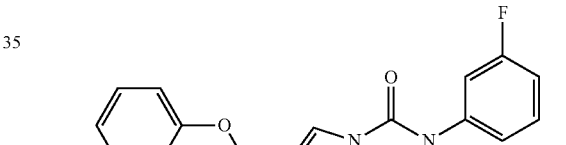
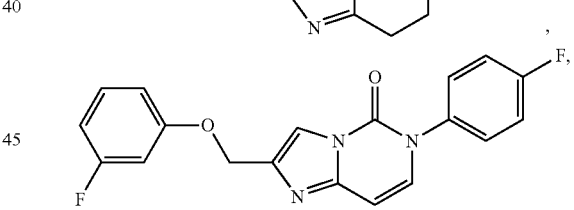
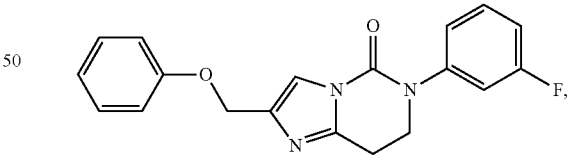
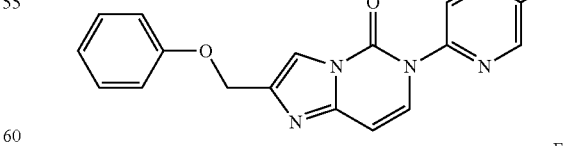
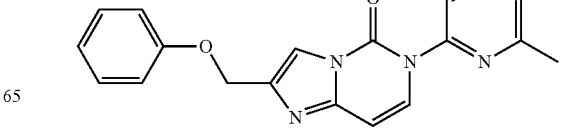

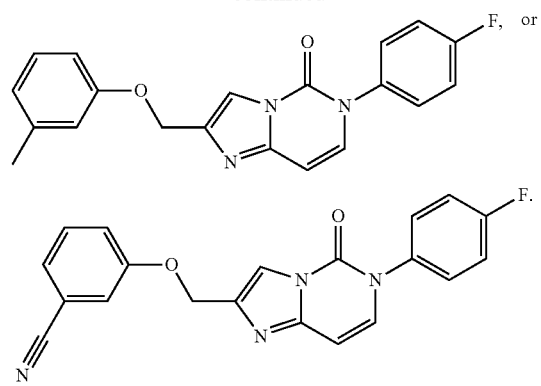
In one aspect, a compound can be present as:
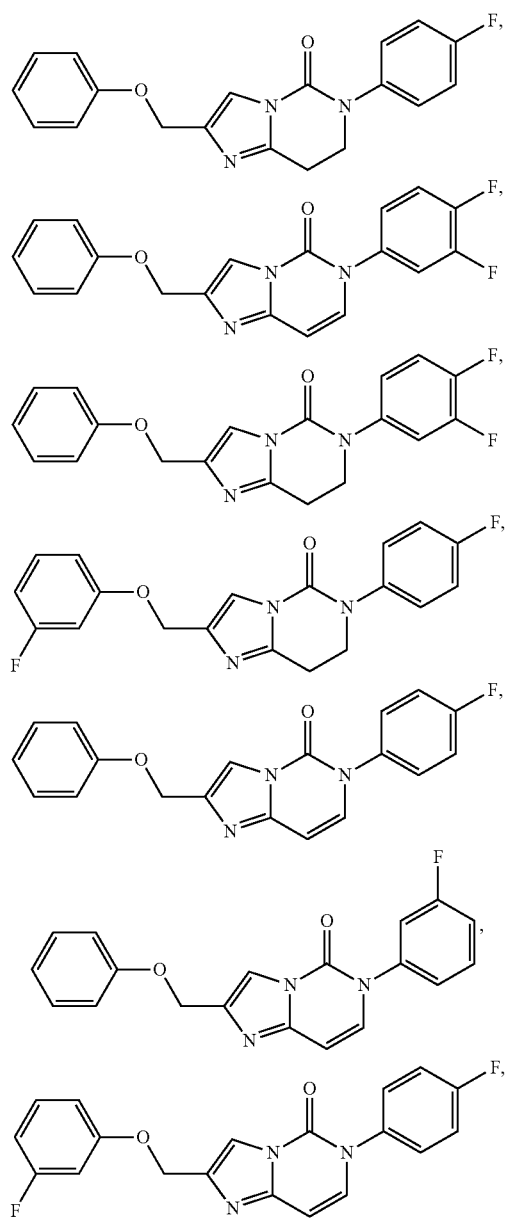
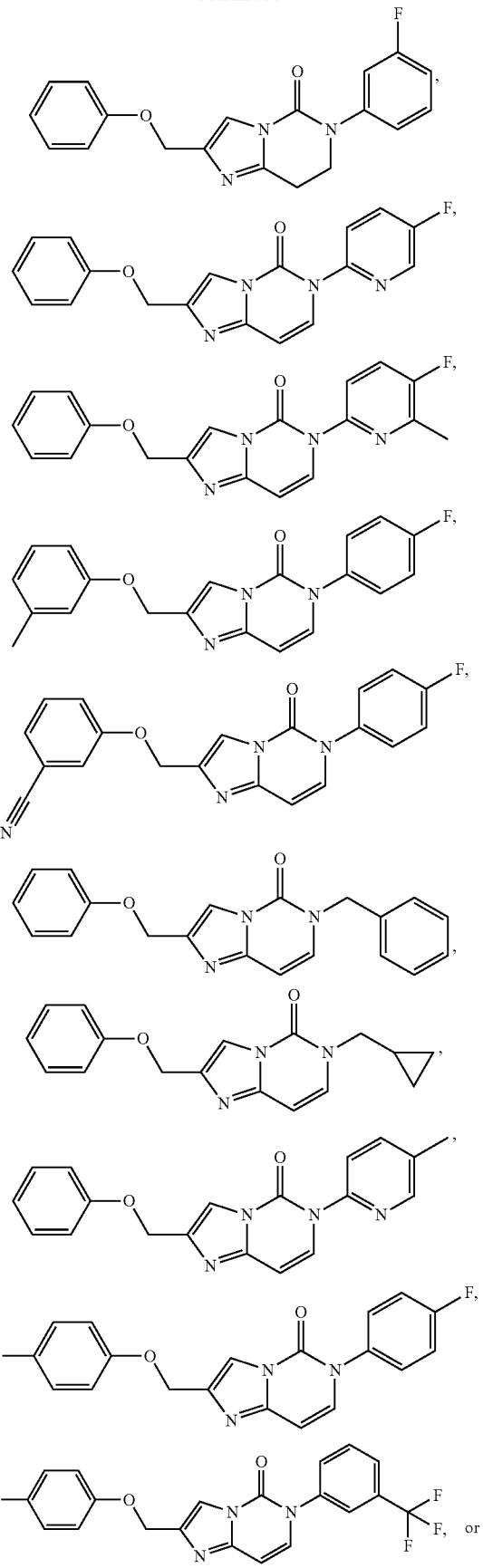

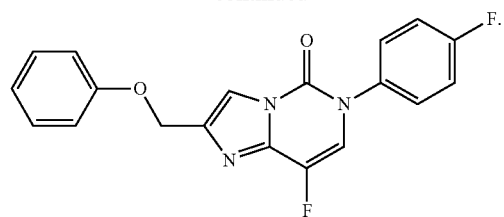
In one aspect, a compound can be present as:
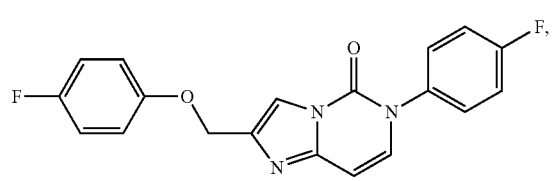
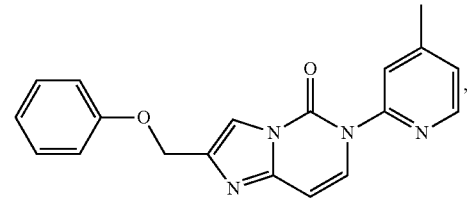
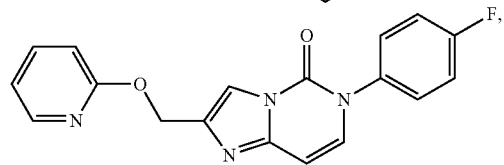
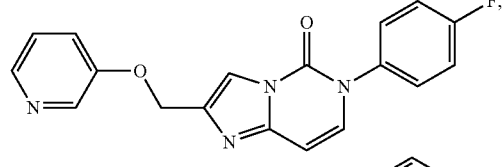
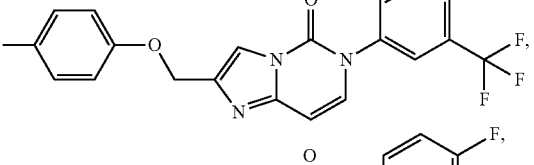
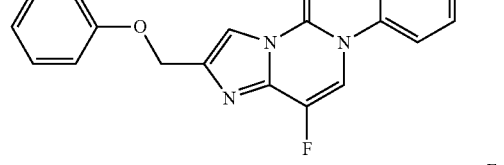
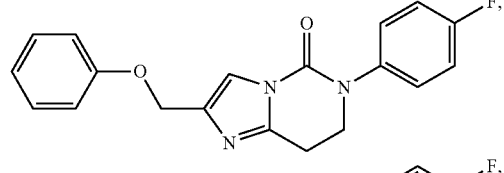
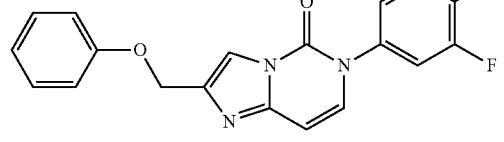
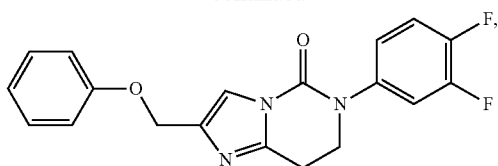
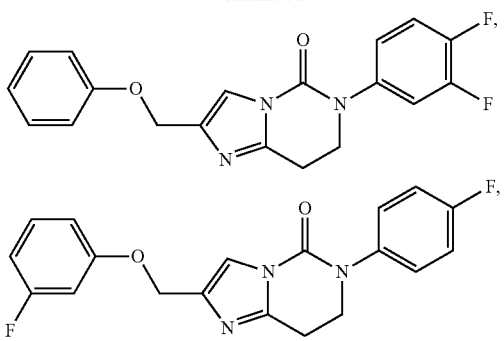
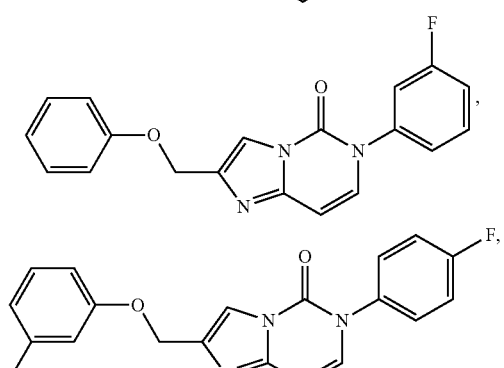
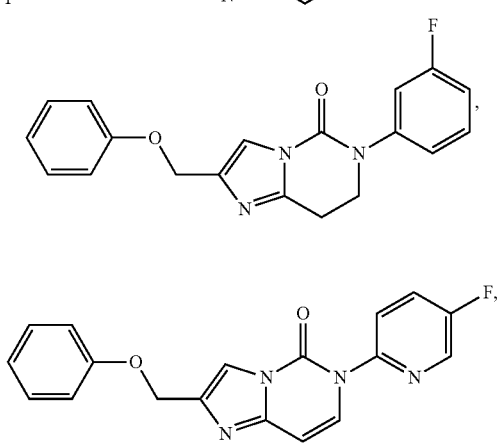
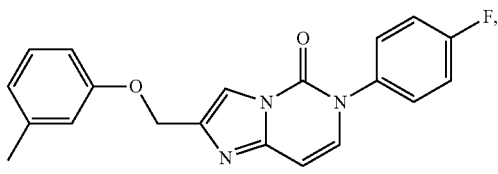

71
-continued
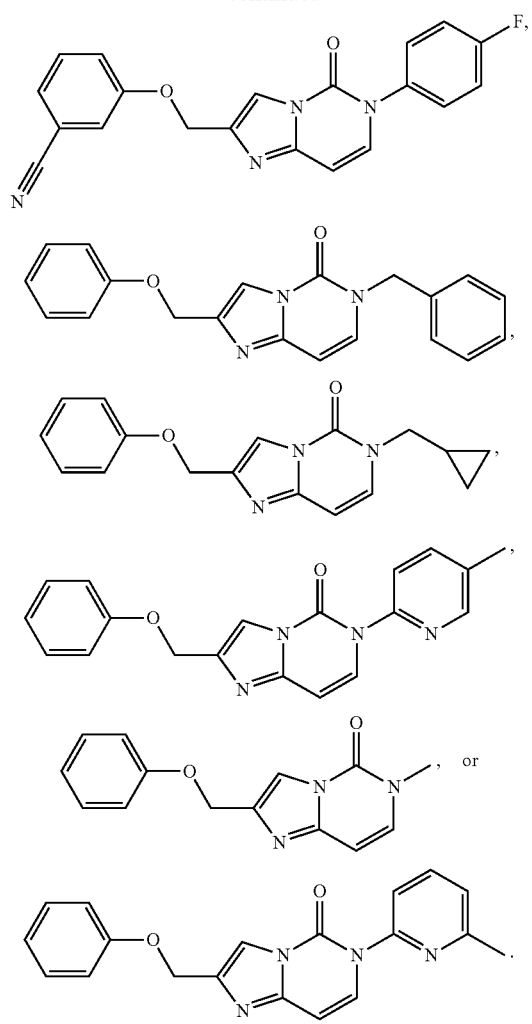
In one aspect, a compound can be present as:
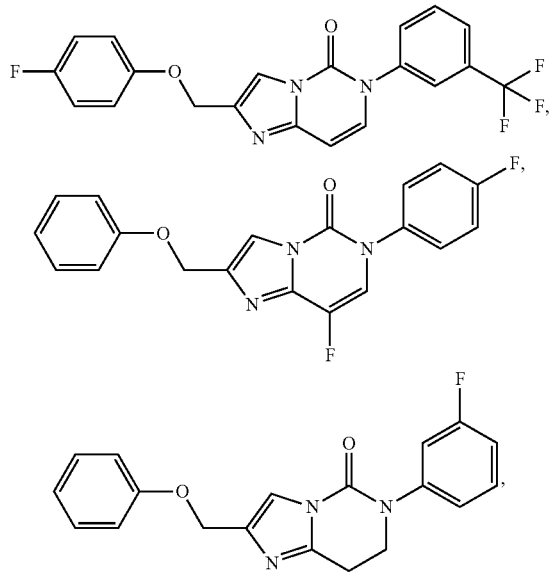
72
-continued
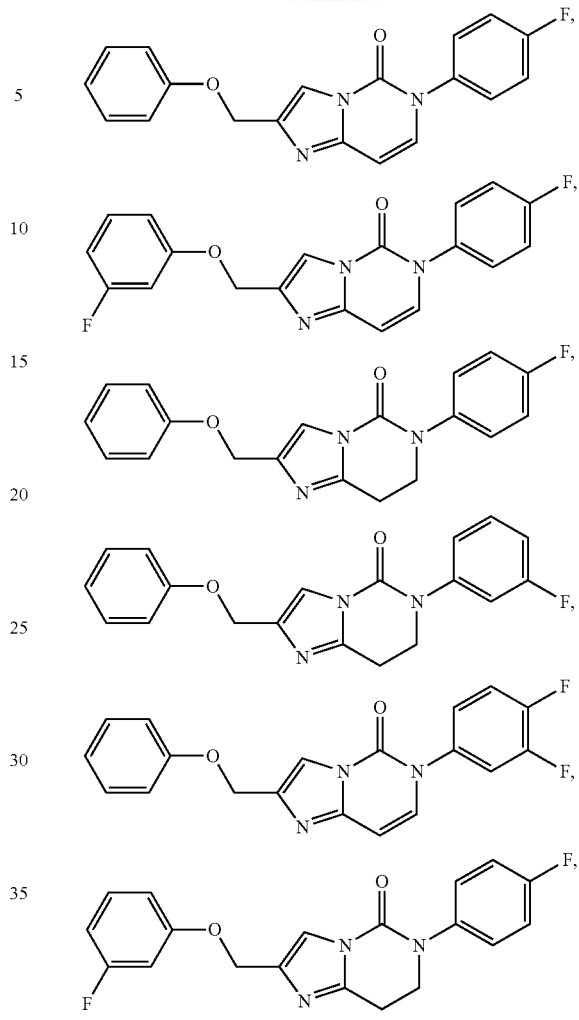
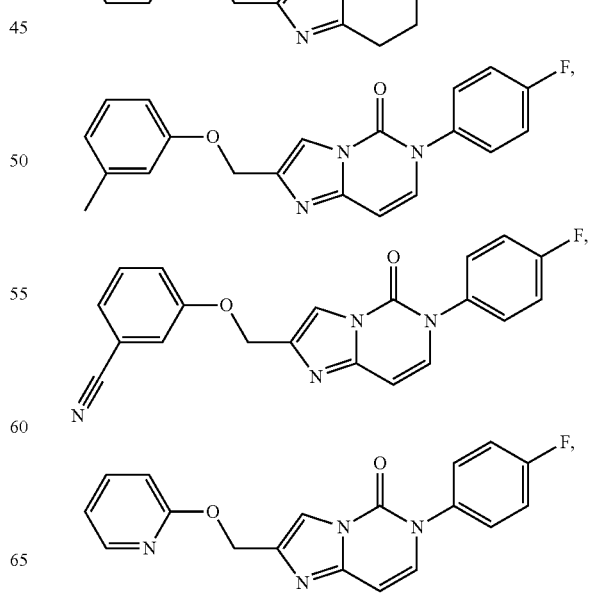

-continued
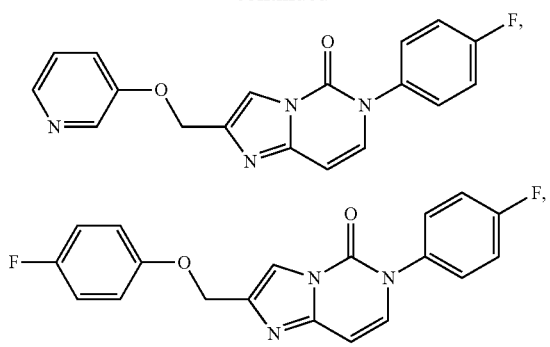
In one aspect, a compound can be present as:
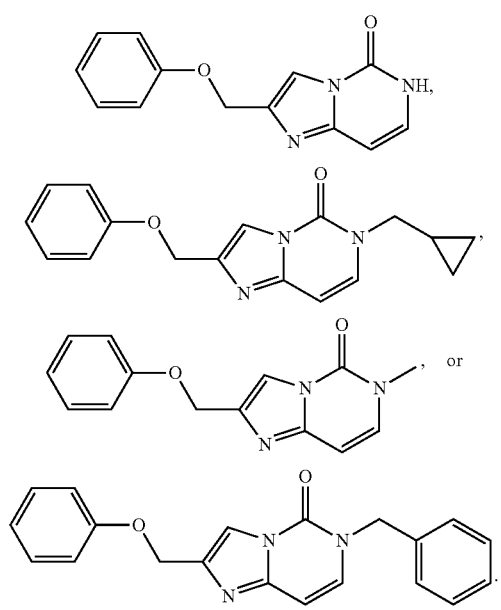
In one aspect, a compound can be present as:
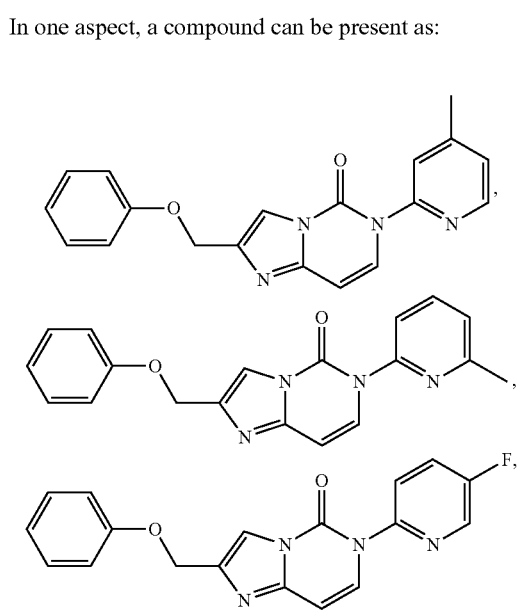
-continued
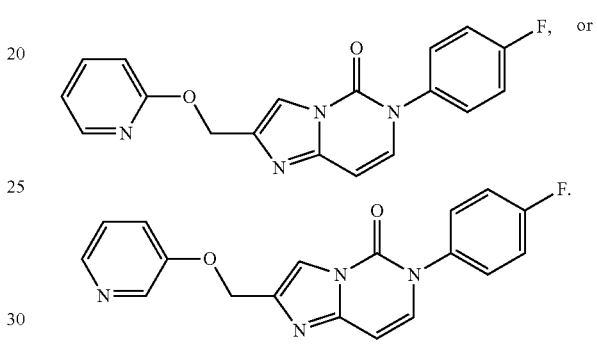
In one aspect, a compound can be present as:
In a further aspect, a compound can be present as:
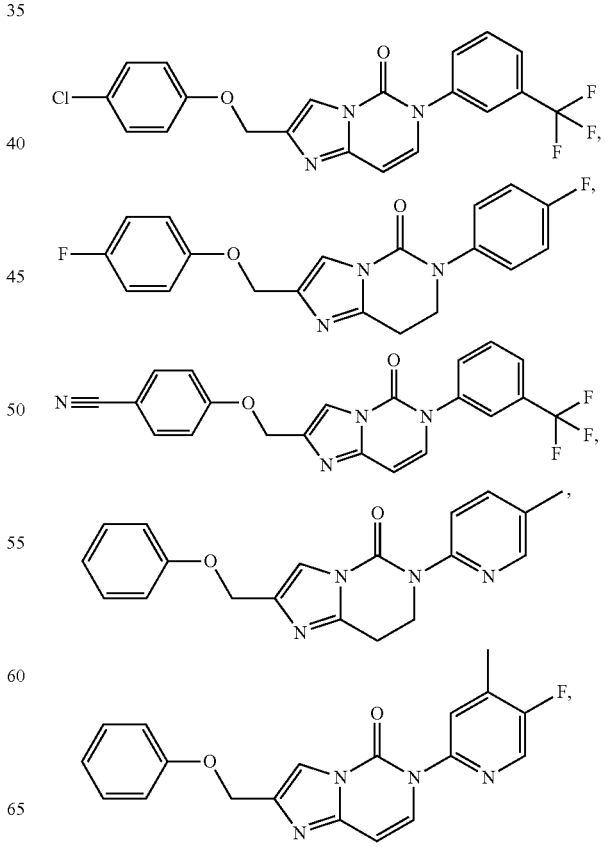

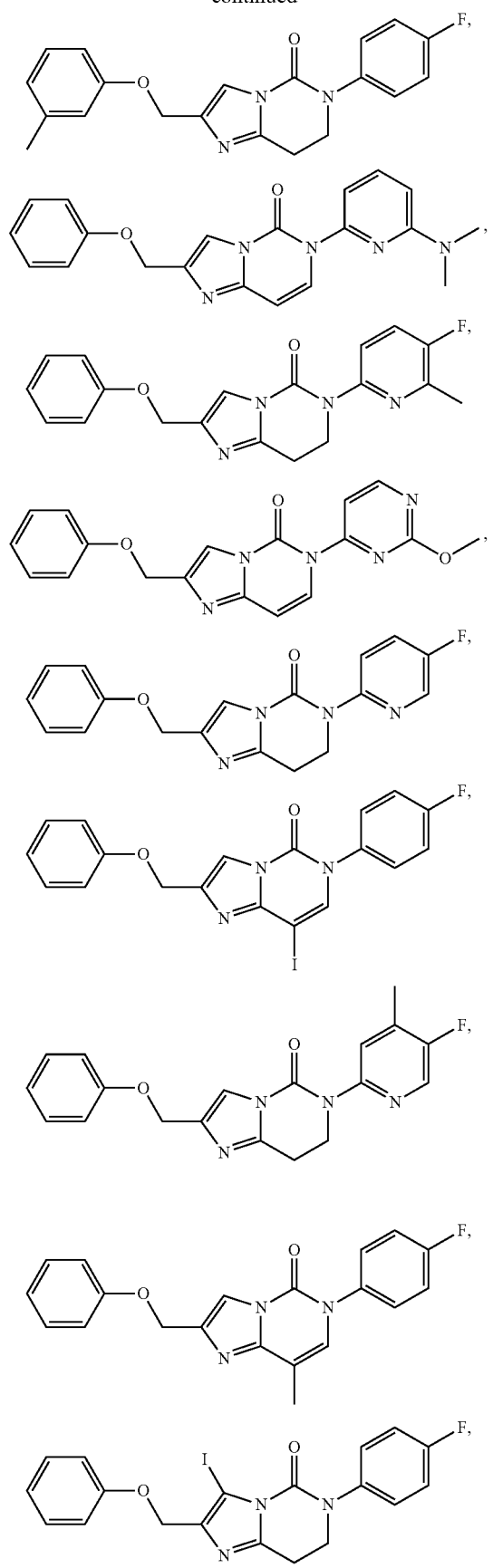
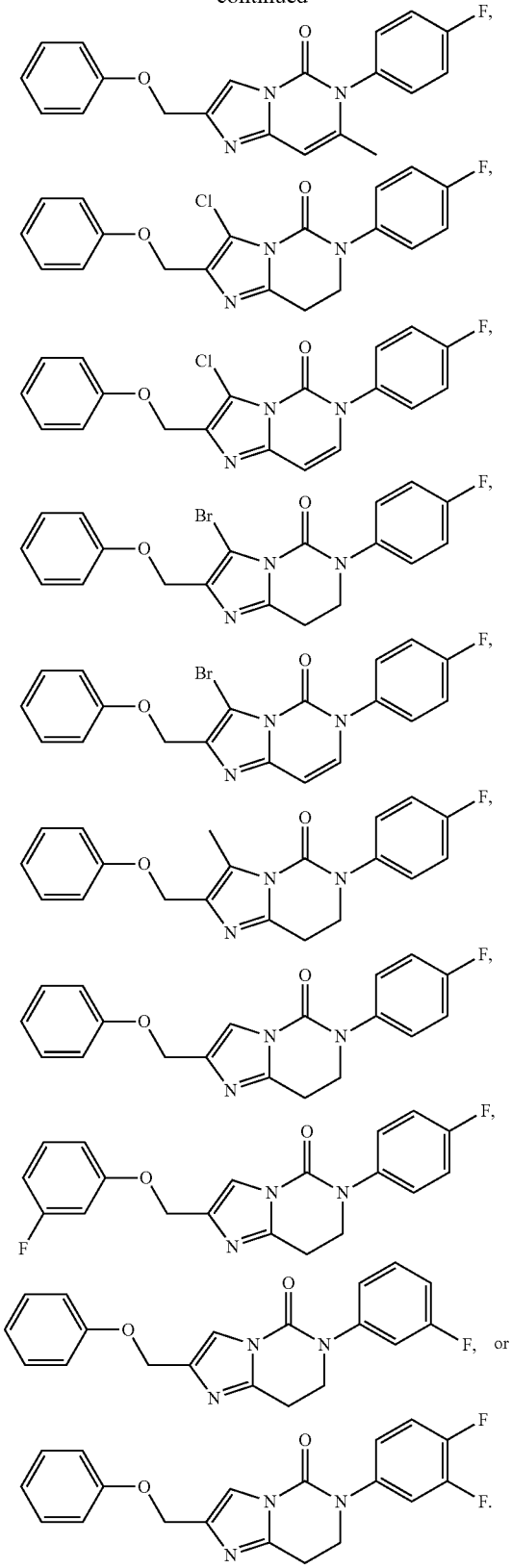
In yet a further aspect, the compound produced exhibits positive allosteric modulation of mGluR5 response to glutamate as a increase in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In yet a further aspect, the compound produced exhibits positive allosteric modulation of mGluR5 after contacting a cell expressing mGluR5.

In a further aspect, the disclosed compounds are allosteric modulators of mGluR5, in particular, positive allosteric modulators of mGluR5. The diclosed compounds can potentiate glutamate responses by binding to an allosteric site other than the glutamate orthosteric binding site. The response of mGluR5 to a concentration of glutamate is increased when the disclosed compounds are present. In a further aspect, the disclosed compounds can have their effect substantially at mGluR5 by virtue of their ability to enhance the function of the receptor.

It is contemplated that one or more compounds can optionally be omitted from the disclosed invention.

3. Positive Allosteric Modulation of mGLuR5 Response

Generally, the disclosed compounds exhibit potentiation of mGluR5 response to glutamate as an increase in response to non-maximal concentrations of glutamate in human embryonic kidney cells transfected with mGluR5 in the presence of the compound, compared to the response to glutamate in the absence of the compound. For example, a compound can exhibit positive allosteric modulation of mGluR5 with an $EC_{50}$ of less than about 10,000 nM, of less than about 5,000 nM. of less than about 1,000 nM, of less than about 500 nM, or of less than about 100 nM. In a further aspect, the mGluR5 is rat mGluR5. In a still further aspect, the mGluR5 is human mGluR5.

In one aspect, the disclosed compounds exhibit potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a yet further aspect, the transfected cell line is the H12H cell line. For example, a compound can exhibit positive allosteric modulation of transfected human mGluR5 ith an $EC_{50}$ of less than about 10,000 nM, of less than about 5,000 nM. of less than about 1,000 nM, of less than about 500 nM, or of less than about 100 nM.

In one aspect, the disclosed compounds exhibit potentiation of mGluR5 response to glutamate as an increase in response to non-maximal concentrations of glutamate in human embryonic kidney cells transfected with rat mGluR5 in the presence of the compound, compared to the response to glutamate in the absence of the compound. For example, a compound can exhibit positive allosteric modulation of transfected rat mGluR5 with an $EC_{50}$ of less than about 10,000 nM, of less than about 5,000 nM. of less than about 1,000 nM, of less than about 500 nM, or of less than about 100 nM.

C. Metabotropic Glutamate Receptor Activity

The utility of the compounds in accordance with the present invention as potentiators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). In the alternative assay, HEK cells transfected with human mGluR5 were plated for assay in the FDSS. In some cases the HEK cells transfected with human mGluR5 were the H10H cell line. Alternatively, the HEK cells transfected with human mGluR5 were the H12H cell line. Rat assay results were found to correlate well with human assay results. The cells were loaded with a $Ca^{2+}$-sensitive fluorescent dye (e.g., Fluo-4), and the plates were washed and placed in the FDSS instrument. After establishment of a fluorescence baseline for twelve seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist (here, glutamate) in the presence of compound compared to the response to agonist in the absence of compound.

The above described assay operated in two modes. In the first mode, a range of concentrations of the present compounds were added to cells, followed by a single fixed concentration of agonist. If a compound acted as a potentiator, an $EC_{50}$ value for potentiation and a maximum extent of potentiation by the compound at this concentration of agonist was determined by non-linear curve fitting. In the second mode, several fixed concentrations of the present compounds were added to various wells on a plate, followed by a range of concentrations of agonist for each concentration of present compound; the $EC_{50}$ values for the agonist at each concentration of compound were determined by non-linear curve fitting. A decrease in the $EC_{50}$ value of the agonist with increasing concentrations of the present compounds (a leftward shift of the agonist concentration-response curve) is an indication of the degree of mGluR5 potentiation at a given concentration of the present compound. An increase in the $EC_{50}$ value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In one aspect, the disclosed compounds exhibit potentiation of mGluR5 response to glutamate as an increase in response to non-maximal concentrations of glutamate in human embryonic kidney cells transfected with a mammalian mGluR5 in the presence of the compound, compared to the response to glutamate in the absence of the compound. For example, human embryonic kidney cells can be transfected with human mGluR5. For example, human embryonic kidney cells can be transfected with rat mGluR5. For example, a compound can exhibit positive allosteric modulation of mGluR5 (e.g., rmGluR5) with an $EC_{50}$ of less than about 10,000 nM, of less than about 5,000 nM. of less than about 1,000 nM, of less than about 500 nM, or of less than about 100 nM. Alternatively, the disclosed compounds exhibit potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a yet further aspect, the transfected cell line is the H12H cell line. For example, a compound can exhibit positive allosteric modulation of mGluR5 (e.g., hmGluR5) with an $EC_{50}$ of less than about 10,000 nM, of less than about 5,000 nM. of less than about 1,000 nM, of less than about 500 nM, or of less than about 100 nM.

In particular, the disclosed compounds exhibit activity in potentiating the mGluR5 receptor in the aforementioned assays, generally with an $EC_{50}$ for potentiation of less than about 10 µM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are selective positive allosteric modulators (potentiators) of human and rat mGluR5 compared to the other seven subtypes of metabotropic glutamate receptors.

In vivo efficacy for disclosed compounds can be measured in a number of preclinical rat behavioral model where known, clinically useful antipsychotics display similar positive responses. For example, disclosed compounds can reverse amphetamine-induced hyperlocomotion in male Sprague-Dawley rats at doses ranging from 1 to 100 mg/kg p.o.

D. Methods of Making the Compounds

In one aspect, the invention relates to methods of making compounds useful as positive allosteric modulators of the metabotropic glutamate receptor subtype 5 (mGluR5), which can be useful in the treatment neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In a further aspect, the compound produced exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

1. Route I

In one aspect, substituted imidazo[1,2-c]pyrimidin-5(6H)-one analogs of the present invention can be prepared generically as shown below.

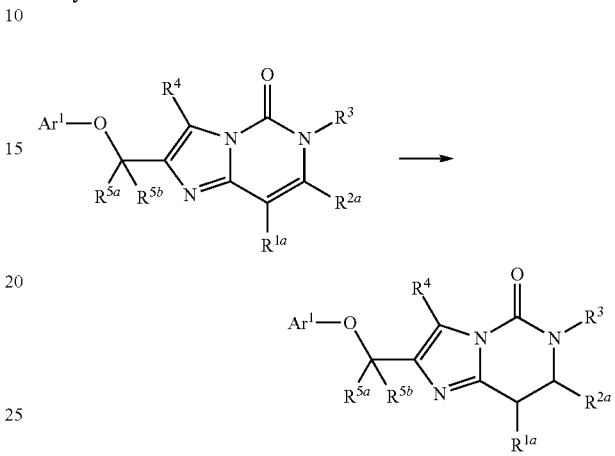

Compounds are represented in generic form, with substituents as noted in compound descriptions elsewhere herein. A more specific example is set forth below.

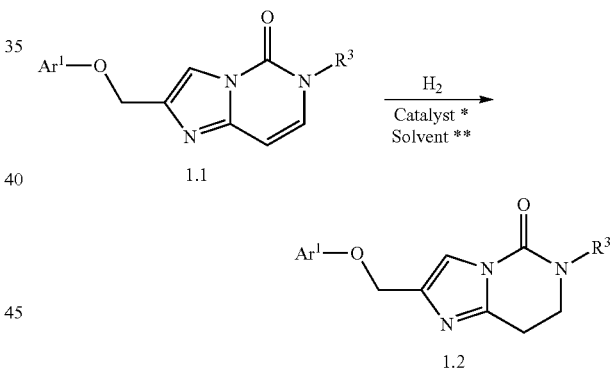

\* For example, Pd(OH)$_2$ or Raney nickel
\*\* For example, MeOH, EtOH or mixture of MeOH/DMF In one aspect, compounds of type 1.2 can be prepared by hydrogenation of the corresponding unsaturated analog as represented by compound 1.1. Briefly, reaction comprising compound 1.1 and hydrogen gas is performed in the presence of a suitable catalyst, e.g. palladium hydroxide or Raney nickel, and an inert solvent such as methanol, ethanol or a mixture of methanol and N,N-dimethylformamide. Typically the reaction is performed at about 30° C. to about 70° C., with a hydrogen gas pressure of about normal atmospheric pressure to about 50 psi or at about 30° C. to about 100° C. with a continuous flow of hydrogen gas, for a period of time sufficient to complete the reaction.

Thus, in one aspect, the invention relates to a method of making a compound comprising the steps of: (a) providing a compound having a structure represented by a formula:

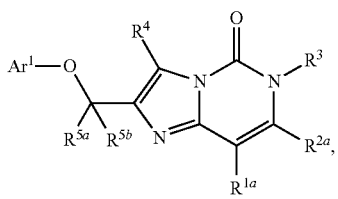

wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein R$^3$ is selected from phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein R$^4$ is selected from hydrogen, halogen, cyano, and C1-C4 alkyl; wherein each of R$^{5a}$ and R$^{5b}$ is independently selected from hydrogen and C1-C4 alkyl; wherein R$^{1a}$ and R$^{2a}$ are optionally covalently bonded and, together with the intermediate atoms, comprise an optionally substituted 3- to 7-membered fused cycloalkyl, and (b) hydrogenating the compound, thereby yielding a compound having a structure represented by a formula:

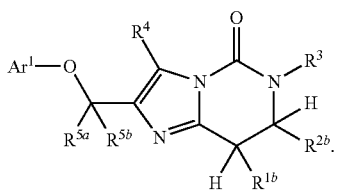

In a further aspect, hydrogenating comprises reaction with hydrogen in the presence of a palladium catalyst. In a yet further aspect, hydrogenating comprises reaction with hydrogen in the presence of Raney nickel.

2. Route II

In one aspect, substituted imidazo[1,2-c]pyrimidin-5(6H)-one analogs of the present invention can be prepared generically by one of the synthetic schemes as shown below.

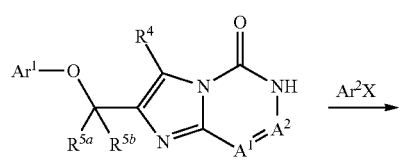

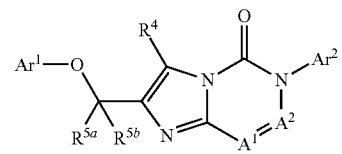

Compounds are represented in generic form, with substituents as noted in compound descriptions elsewhere herein. More specific examples are set forth below.

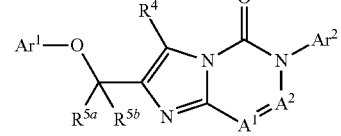

* X is Br, Cl or I
** For example, dimethylethylenediamine or 2-dicyclohexylphosphino-2',4',6'-triiso-propyl-1,1'-biphenyl

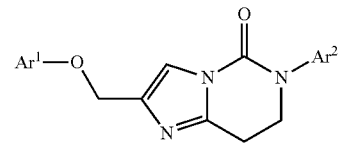

* X is Br, Cl or I
** For example, dimethylethylenediamine or 2-dicyclohexylphosphino-2',4',6'-triiso-propyl-1,1'-biphenyl

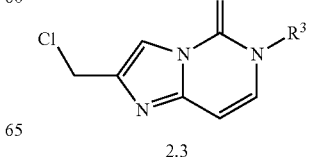

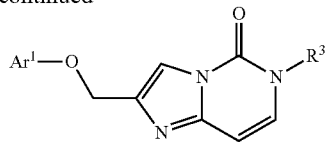

1.1

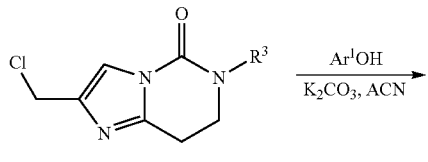

2.4

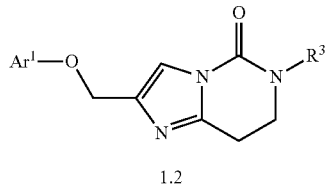

1.2

In one aspect, compounds of type 1.1 can be prepared from compounds of type 2.1 by reaction with a suitable, aryl halide or heteroaryl halide, wherein the halo moiety is bromo, chloro or iodo, in the presence of a coupling agent, e.g. copper(I) iodide or palladium (II) acetate, a ligand, e.g. N,N-dimethyl-ethylenediamine or 2-dicyclohexylphosphino-2',4',6'-triiso-propyl-1,1'-biphenyl, and a base, e.g. potassium carbonate or cesium carbonate. Reactions of this type are typically carried out in an inert solvent such as toluene or 1,4-dioxane at an appropriate reaction temperature, e.g. from about 100° C. to about 140° C., for a period of time sufficient to complete the reaction.

In one aspect, compounds of type 1.1 can alternatively be prepared from compounds of type 2.3 by reaction with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction.

In one aspect, compounds of type 1.2 can be prepared from compounds of type 2.2 by reaction with a suitable, aryl halide or heteroaryl halide, wherein the halo moiety is bromo, chloro or iodo, in the presence of a coupling agent, e.g. copper(I) iodide or palladium (II) acetate, a ligand, e.g. N,N-dimethyl-ethylenediamine or 2-dicyclohexylphosphino-2',4',6'-triiso-propyl-1,1'-biphenyl, and a base, e.g. potassium carbonate or cesium carbonate. Reactions of this type are typically carried out in an inert solvent such as toluene or 1,4-dioxane at an appropriate reaction temperature, e.g. from about 100° C. to about 140° C., for a period of time sufficient to complete the reaction.

In one aspect, compounds of type 1.2 can alternatively be prepared from compounds of type 2.4 by reaction with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction.

Thus, in one aspect, the invention relates to a method of making a compound comprising the steps of: (a) providing a compound having a structure represented by a formula:

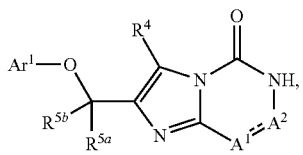

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) reacting the compound with $R^3X$, wherein X is a leaving group, and wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; thereby substituting at the amide. In a further aspect, X is a halogen.

In a further aspect, the prepared compound has a structure represented by a formula:

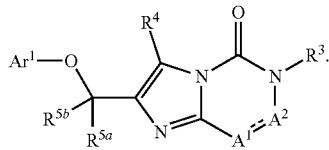

Thus, in one aspect, the invention relates to a method of making a compound comprising the steps of: (a) providing a compound having a structure represented by a formula:

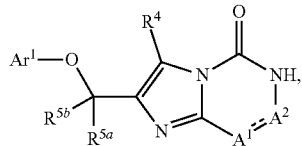

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) coupling the compound with $R^3X$, in the presence of a coupling reagent, wherein X is bromo or iodo, and wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; thereby substituting at the amide. In a further aspect, the coupling reagent is copper(I)iodide.

In a further aspect, the prepared compound has a structure represented by a formula:

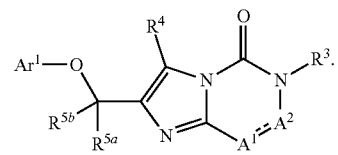

In a further aspect, the compound provided has a structure represented by a formula:

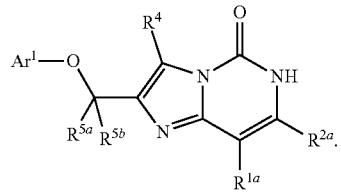

In a still further aspect, the compound formed when the above compound is the compound provided has a structure represented by a formula:

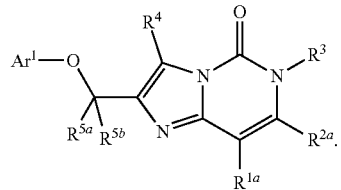

In a yet further aspect, the method further comprises hydrogenating the compound formed, thereby yielding a compound having a structure represented by a formula:

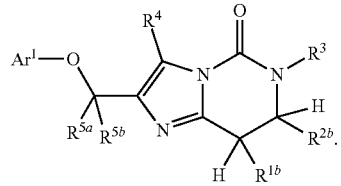

In an even further aspect, hydrogenating comprises reaction with hydrogen in the presence of a palladium catalyst. In a further aspect, hydrogenating comprises reaction with hydrogen in the presence of Raney nickel.

In a further aspect, the compound provided has a structure represented by a formula:

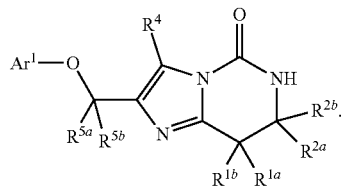

In a still further aspect, the compound formed when the above compound is the compound provided has a structure represented by a formula:

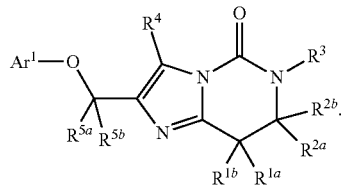

Thus, in one aspect, the invention relates to a method of making a compound comprising the steps of: (a) providing a compound having a structure represented by a formula:

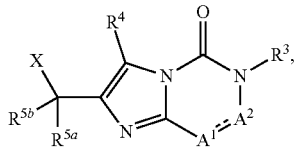

wherein X is a leaving group; wherein ----- is an optional covalent bond, wherein valence is satisfied; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, and (b) reacting the compound with $Ar^1OH$, wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl, thereby forming:

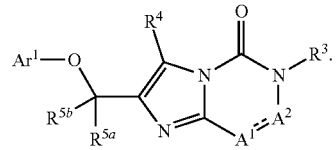

In a further aspect, the leaving group is a halogen. In a still further aspect, the halogen is chloro. In a yet further aspect, the reaction is performed in the presence of base.

In a further aspect, the compound provided has a structure represented by the formula:

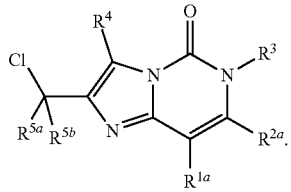

In a still further aspect, the compound formed when the above compound is the compound provided has a structure represented by a formula:

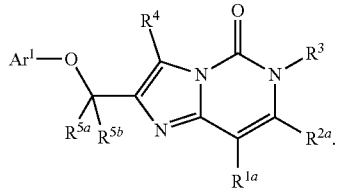

In a yet further aspect, the method further comprises hydrogenating the compound formed, thereby yielding a compound having a structure represented by a formula:

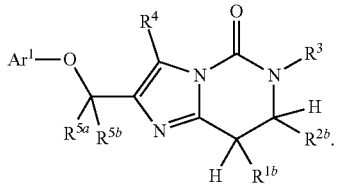

In an even further aspect, hydrogenating comprises reaction with hydrogen in the presence of a palladium catalyst. In a further aspect, hydrogenating comprises reaction with hydrogen in the presence of Raney nickel.

In a further aspect, the compound provided has a structure represented by the formula:

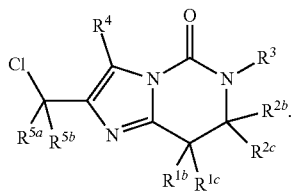

In a still further aspect, the compound formed when the above compound is the compound provided has a structure represented by a formula:

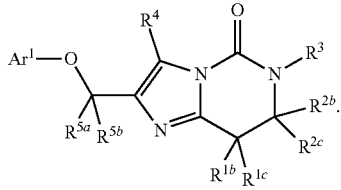

3. Route III

In one aspect, substituted imidazo[1,2-c]pyrimidin-5(6H)-one analogs of the present invention can be prepared generically as shown below.

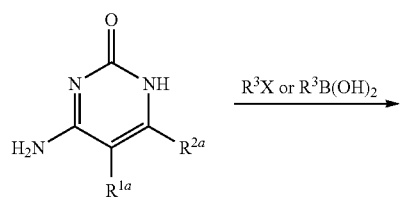

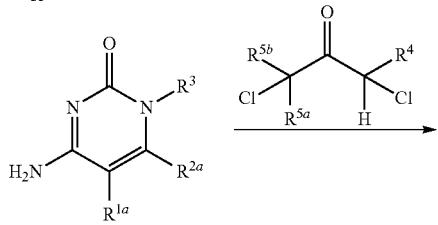

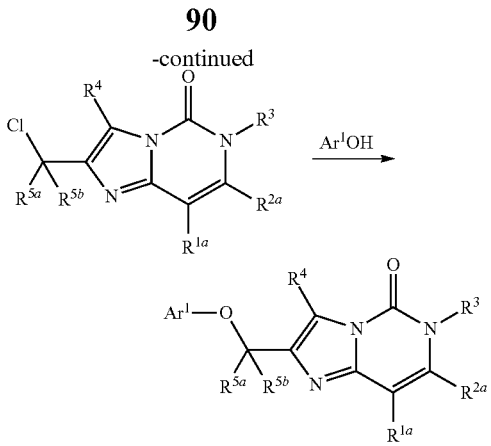

Compounds are represented in generic form, with substituents as noted in compound descriptions elsewhere herein. More specific examples are set forth below.

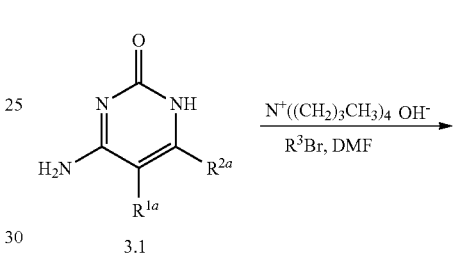

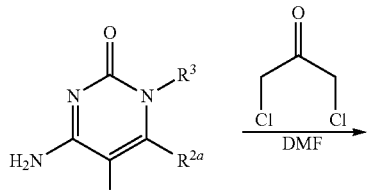

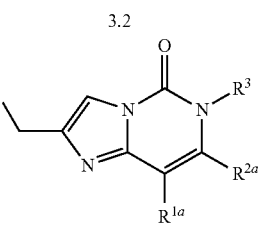

2.3

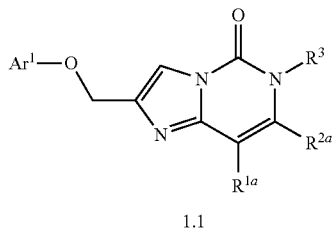

1.1

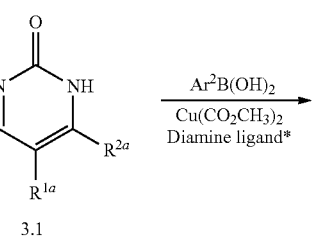

3.1

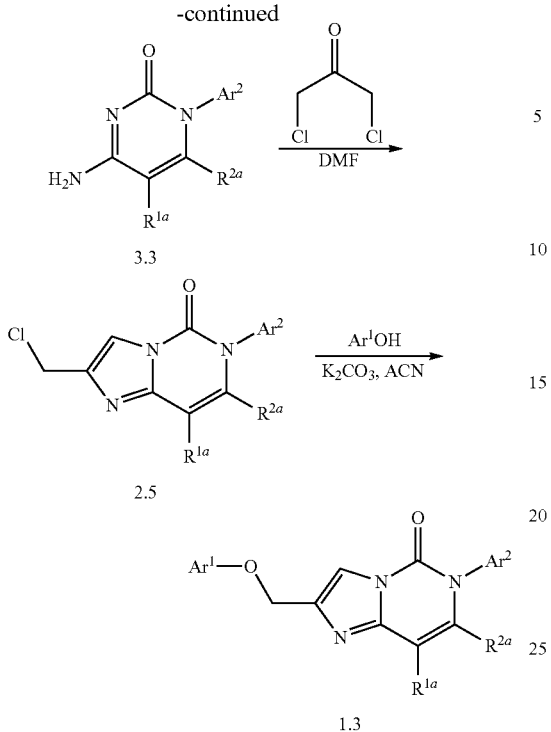

\* For example, dimethylethylenediamine

In one aspect, compounds of type 1.1 can be prepared starting with 4-aminopyrimidin-2(1H)-one analogs shown as compound type 3.1. Compound type 3.1 is reacted with a suitable alkylating compound with an appropriate leaving group, such as $R^3Br$ (although leaving groups other than bromo can also be utilized). The reaction is carried out in the presence of a suitable base, e.g. tetra-N-butylammonium hydroxide, in an inert solvent such as N,N-dimethylformamide at a suitable temperature, e.g. from about 0° C. to about 40° C., for a period of time sufficient to complete the reaction. Similar procedures are described in Eur. J. Med. Chem. (2009) 44:1172-1179. The product of this reaction, compound 3.2, is then reacted with a suitable dihaloketone, e.g. 1,2-dichloroacetone, in the presence of an inert solvent, e.g. N,N-dimethylformamide, to afford a compound of type 2.3. This reaction can be carried out by heating with microwave irradiation for a period of time sufficient to insure completion. Conversion of the product, compound 2.3, to a compound of type 1.1 is accomplished by methods described above for Route II. Briefly, the compound is reacted with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction.

In one aspect, compounds of type 1.3 can be prepared starting with 4-aminopyrimidin-2(1H)-one analogs shown as compound type 3.1. Compound type 3.1 is reacted with an appropriate aryl (including heteroaryl) boronic derivative represented by the formula $Ar^2B(OH)_2$ in the presence of a suitable coupling agent, e.g. copper(II)acetate monohydrate and a suitable ligand, e.g. N,N,N',N'-tetramethylethylenediamine. The reaction is carried out in an inert solvent such as toluene at a suitable temperature, e.g. from about 0° C. to about 40° C. for a period of time sufficient to insure completion of the reaction. Procedures similar to those described in Eur. J. Org. Chem. (2005) 5154-5157 can be used. The product of this reaction, compound 3.3, is then reacted with a suitable dihaloketone, e.g. 1,2-dichloroacetone, in the presence of an inert solvent, e.g. N,N-dimethylformamide, to afford a compound of type 2.5. This reaction can be carried out by heating with microwave irradiation for a period of time sufficient to insure completion. Conversion of the product, compound 2.5, to a compound of type 1.3 is accomplished by methods described above for Route II. Briefly, the compound is reacted with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction.

Thus, in one aspect, the invention relates to a method of making a compound comprising the steps of: (a) providing a compound having a structure represented by a formula:

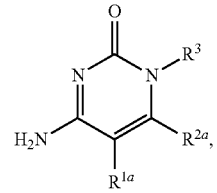

wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, (b) reacting the compound with a compound represented by the formula:

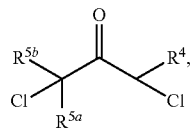

wherein $R^4$ is selected from hydrogen, halogen, cyano, and C1-C4 alkyl; and wherein each of $R^{5a}$ and $R^{5b}$ is independently selected from hydrogen and C1-C4 alkyl. In a still further aspect, reacting is carried out using microwave irradiation.

In various aspects, the compound represented by the formula:

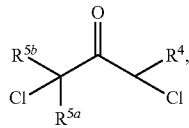

$R^4$ is hydrogen or C1-C4 alkyl. In a further aspect, $R^4$ is hydrogen. In a still further aspect, $R^4$ is hydrogen, methyl, ethyl, propyl or isopropyl. In a yet further aspect, $R^4$ is hydrogen or methyl.

In a further aspect, the prepared compound has a structure represented by a formula:

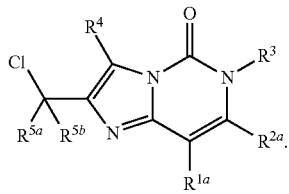

In a further aspect, the method further comprises the step of reacting the compound formed with $Ar^1OH$, wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl, thereby forming a compound represented by a formula:

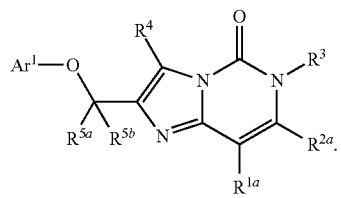

In a still further aspect, reacting the compound formed with $Ar^1OH$ is performed in the presence of base. In a yet further aspect, the method further comprises hydrogenating the compound formed following reaction with $Ar^1OH$, thereby yielding a compound having a structure represented by a formula:

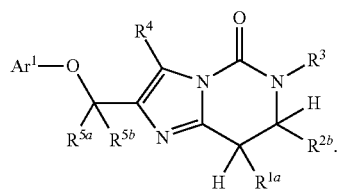

4. Route IV

In one aspect, substituted imidazo[1,2-c]pyrimidin-5(6H)-one analogs of the present invention can be prepared generically as shown below.

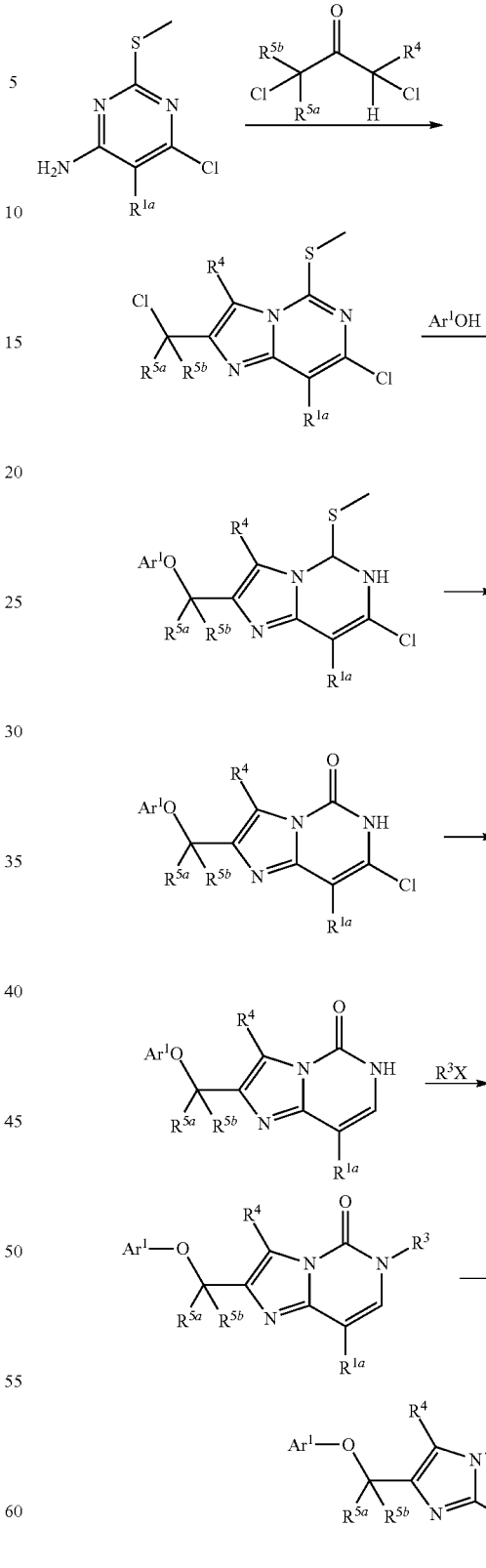

Compounds are represented in generic form, with substituents as noted in compound descriptions elsewhere herein. A more specific example is set forth below.

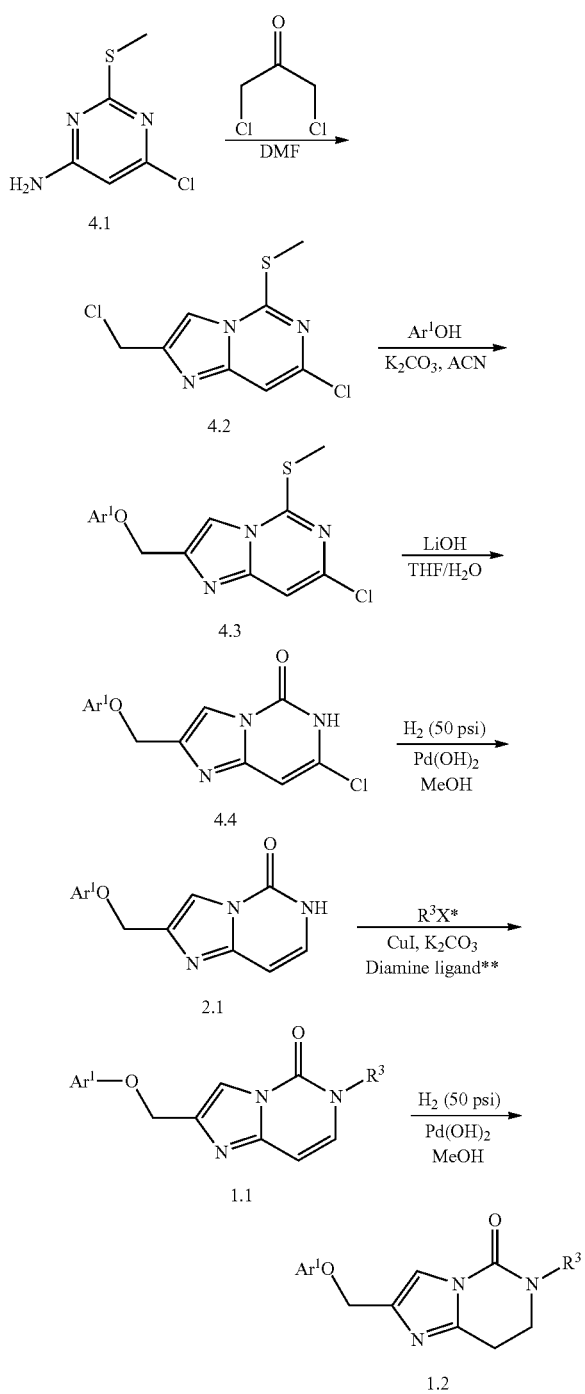

\* X is Br or I
\*\* For example, dimethylethylenediamine

In one aspect, compounds of type 1.1 and 1.2 can be prepared starting with a suitable 6-chloro-2-(methylthio)pyrimidin-4-amine analog, such as compound type 4.1, and reacting with a suitable dihaloketone, e.g. 1,2-dichloroacetone. The reaction is carried out in an appropriate inert solvent, e.g. N,N-dimethylformamide, at a convenient reaction temperature, e.g. from about 20° C. to about 70° C., for a period of time to insure completion of the reaction. Similar procedures to those described in patent application number PCT/EP2008/001682 (Publication number WO/2008/113469) can be used. Appropriate 6-chloro-2-(methylthio)pyrimidin-4-amine analogs can be purchased commercially. The product can be reacted with a suitable aryl alcohol to afford compounds of type 4.3 using procedures described above for Route II. Briefly, the reaction can be performed in the presence of a suitable base, e.g. potassium carbonate, in an inert solvent such as acetonitrile. Reactions of this type are typically carried out at an appropriate reaction temperature, e.g. from about 20° C. to about 100° C., for a period of time sufficient to insure completion of the reaction. The product of this reaction can be converted to a compound of type 4.4 by hydrolysis in the presence of lithium hydroxide. The reaction is carried out in an appropriate inert solvent, e.g. tetrahydrofuran and water, at a convenient and suitable temperature, e.g from about 30° C. to about 70° C., for a period of time to insure completion of the reaction. A compound of type 2.1 is prepared from the product by a hydrogenation reaction in the presence of hydrogen gas and a suitable catalyst, e.g. palladium hydroxide. The reaction is carried out in an inert solvent, e.g. methanol, at a convenient and suitable temperature, e.g. from about 30° C. to about 80° C., under a suitable hydrogen pressure, e.g. from about atmospheric pressure to about 50 psi, for a period of time to insure completion of the reaction. The reaction steps and condition leading from compound of type 2.1 to compound type 1.1, and then from compound type 1.1 to compound 1.2 are as described above for Routes I and II.

Thus, in one aspect, the invention relates to a method of making a compound comprising the steps of: (a) providing a compound having a structure represented by a formula:

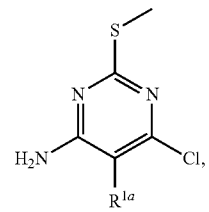

wherein $R^{1a}$ is selected from hydrogen, halogen, C1-C4 alkyl, C1-C4 monohaloalkyl, and C1-C4 polyhaloalkyl, and (b) reacting the compound with a compound represented by a formula:

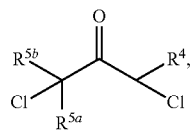

wherein $R^4$ is selected from hydrogen, halogen, cyano, and C1-C4 alkyl; and wherein each of $R^{5a}$ and $R^{5b}$ is independently selected from selected from hydrogen, C1-C4 alkyl, C1-C4 monohaloalkyl, and C1-C4 polyhaloalkyl.

In a further aspect, the prepared compound has a structure represented by a formula:

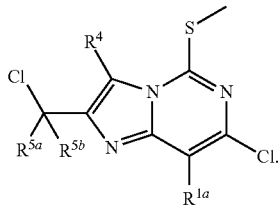

In a further aspect, the method further comprises the step of reacting the compound formed with Ar¹OH, wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl, thereby forming a compound represented by a formula:

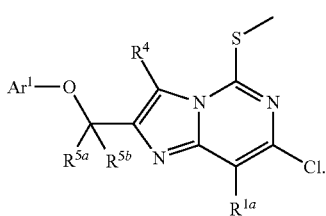

In a yet further aspect, the reaction is performed in the presence of base. In a still further aspect, the method further comprises the step of hydrolysis on the compound formed from reaction with Ar¹OH, wherein hydrolysis is performed in the presence of lithium hydroxide, thereby forming a compound represented by a formula:

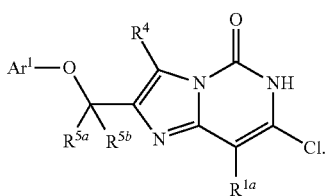

Thus, in one aspect, the invention relates to a method of making a compound comprising the steps of: (a) providing a compound having a structure represented by a formula:

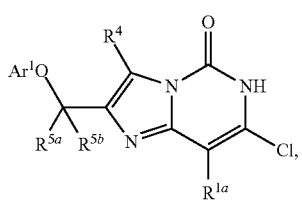

wherein Ar¹ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar¹ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein $R^{1a}$ is selected from hydrogen, halogen, C1-C4 alkyl, C1-C4 monohaloalkyl, and C1-C4 polyhaloalkyl; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl, (b) hydrogenating the compound to yield a compound represented by the formula:

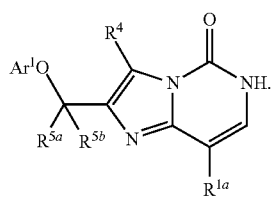

In a yet further aspect, hydrogenation is carried out with hydrogen in the presence of a palladium catalyst. In a still further aspect, the palladium catalyst is palladium hydroxide.

In a further aspect, the method further comprises the step of coupling the compound formed with $R^3X$, in the presence of a coupling reagent, wherein X is bromo or iodo; wherein $R^3$, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); and thereby substituting at the amide. In a yet further aspect, the coupling reagent is copper(I)iodide. In an even further aspect, the amide formed has a structure represented by a formula:

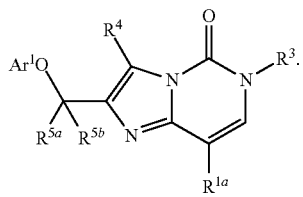

In a further aspect, the method further comprises the step of reacting the compound formed with $R^3X$, wherein X is a leaving group; wherein $R^3$, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl), or Ar² is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); thereby substituting at the amide. In an even further aspect, X is a halogen. In a still further aspect, the amide formed has a structure represented by a formula:

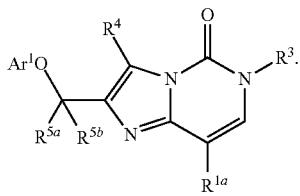

5. Route V

In one aspect, substituted imidazo[1,2-c]pyrimidin-5(6H)-one analogs of the present invention can be prepared generically as shown below.

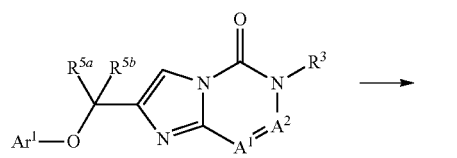

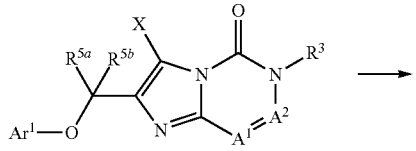

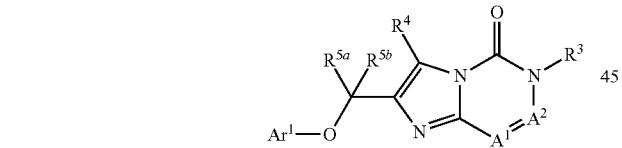

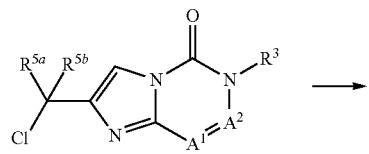

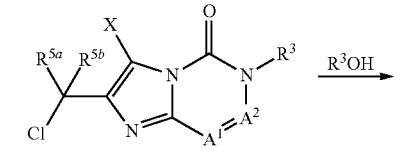

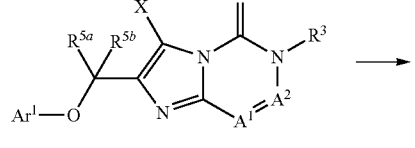

Compounds are represented in generic form, with substituents as noted in compound descriptions elsewhere herein. More specific examples are set forth below.

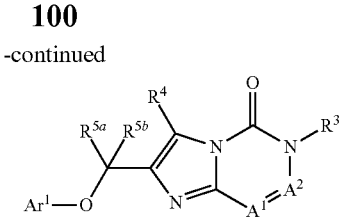

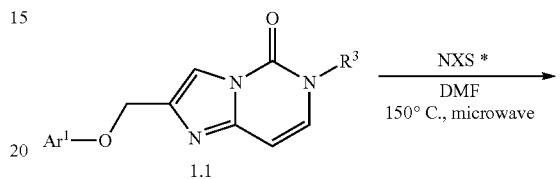

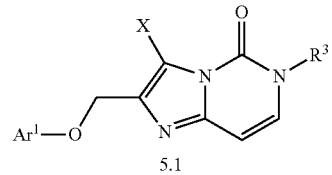

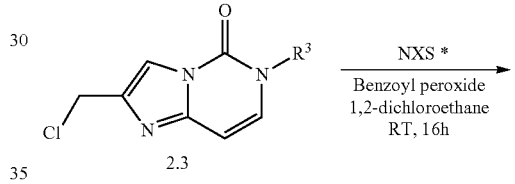

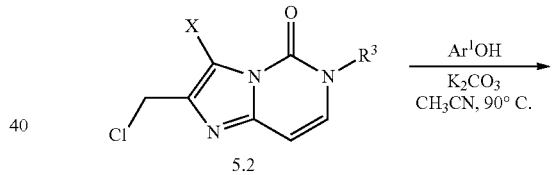

* NXS is N-halo succinimide, e.g. N-Chlorosuccinimide or N-bromosuccinimide.

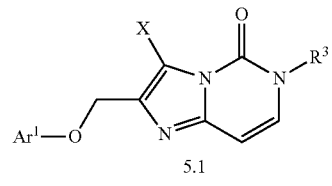

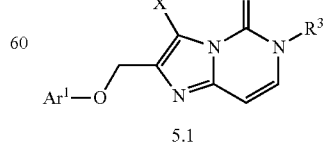

-continued

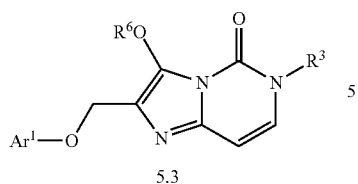
5.3

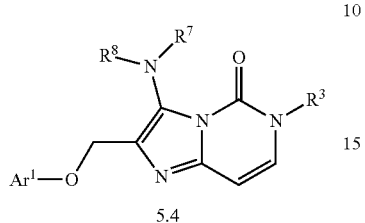
5.4

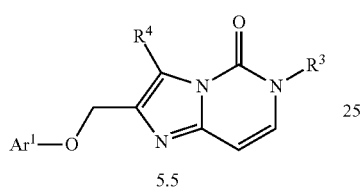
5.5

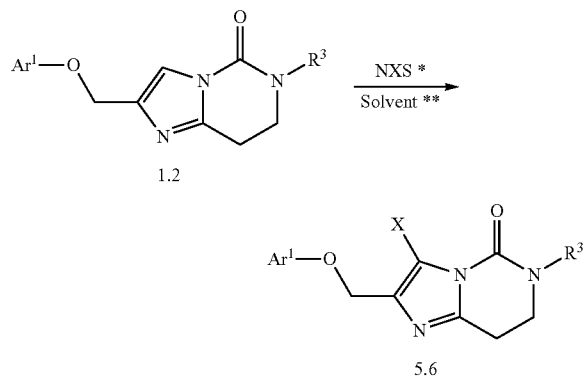

* NXS is N-halosuccinimide, e.g. N-chlorosuccinimide, N-iodosuccinimide or N-bromosuccinimide
** For example, mixture of acetonitrile/acetic acid, N,N-dimethylformamide or 1,2-dichloroethane

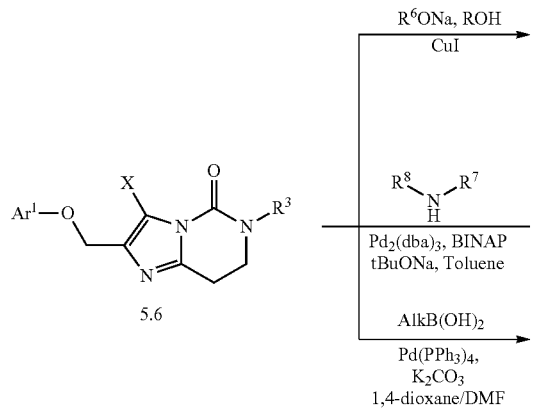

-continued

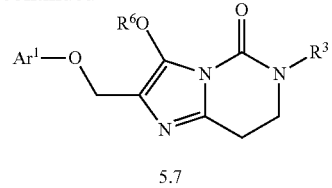
5.7

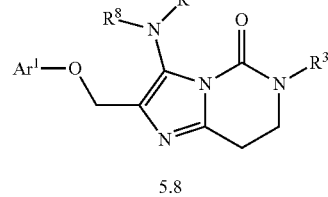
5.8

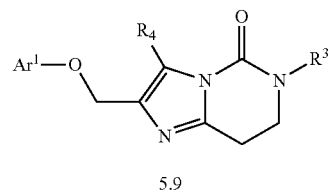
5.9

In one aspect, compounds of type 5.1 can be prepared from the analogous compound of type 1.1 by reaction with an appropriate N-halosuccinimide, e.g. N-chlorosuccinimide, in an inert solvent, e.g. N,N-dimethylformamide. The reaction is carried out at an appropriate temperature, e.g. from about 120° C. to about 150° C., for a period of time sufficient to insure completion of the reaction.

In one aspect, compounds of type 5.1 can alternatively be prepared starting with a compound of type 2.3. The reaction for the first step is carried out by reacting compound 2.3 with a suitable N-halosuccinimide, e.g. N-bromosuccinimide, in the presence of benzoyl peroxide in an appropriate inert solvent, e.g. 1,2-dichloroethane. The reaction is carried out at an appropriate temperature, e.g. from about room temperature to about 60° C., for a period of time to insure completion of the reaction to afford compound type 5.2. The conversion of compound type 5.2 to compound type 5.1 is carried out using reaction conditions as described above for Route II.

The halogenated compound type 5.1 can be converted to a number of derivatives, including the corresponding alkoxy (compound type 5.3), alkylamine (compound type 5.4), and alkyl (compound type 5.5). The typical reaction conditions for preparing each derivative are illustrated in the reaction schemes above.

In one aspect, compounds of type 5.6 can be prepared from the analogous compound of type 1.2 by reaction with an appropriate N-halosuccinimide, e.g. N-chlorosuccinimide, N-iodosuccinimide or N-bromosuccinimide, in an inert solvent, e.g. N,N-dimethylformamide, mixture of acetonitrile and acetic acid or in the presence of benzoyl peroxide in 1,2-dichloroethane. The reaction is carried out at an appropriate temperature, e.g. at room temperature or by heating with microwave irradiation, for a period of time sufficient to insure completion of the reaction.

The halogenated compound type 5.6 can be converted to a number of derivatives, including the corresponding alkoxy (compound type 5.7), alkylamine (compound type 5.8), and alkyl (compound type 5.9). The typical reaction conditions for preparing each derivative are illustrated in the reaction schemes above.

Thus, in one aspect, the invention relates to a method of making a compound comprising the steps of: (a) providing a compound having a structure represented by a formula:

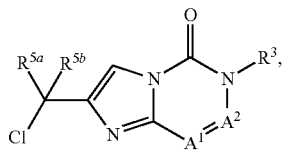

wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and wherein each of $R^{5a}$ and $R^{5b}$ is independently selected from hydrogen, C1-C4 alkyl, C1-C4 monohaloalkyl, and C1-C4 polyhaloalkyl; and (b) halogenating the compound by reaction with N-halosuccinimide. In a yet further aspect, halogenating is reaction with N-bromosuccinimide. In a still further aspect, halogenating is reaction with N-chlorosuccinimide.

In a further aspect, the halogenated compound formed has a structure represented by a formula:

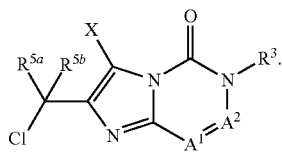

In a further aspect, the method further comprises the step of reacting the halogenated compound formed with Ar$^1$OH, wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl, thereby forming a compound represented by a formula:

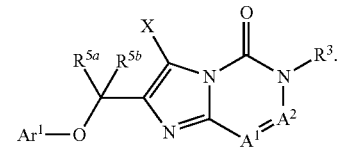

Thus, in one aspect, the invention relates to a method of making a compound comprising the steps of: (a) providing a compound having a structure represented by a formula:

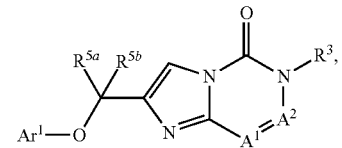

wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein each of R$^{5a}$ and R$^{5b}$ is independently selected from hydrogen, C1-C4 alkyl, C1-C4 monohaloalkyl, and C1-C4 polyhaloalkyl; and (b) halogenating the compound by reaction with N-halosuccinimide. In a still further aspect, halogenating is reacting with N-bromosuccinimide. In a yet further aspect, halogenating is reacting with N-chlorosuccinimide.

In a further aspect, the halogenated compound has a structure represented by a formula:

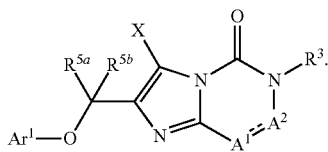

Thus, in one aspect, the invention relates to a method of making a compound comprising the steps of: (a) providing a compound having a structure represented by a formula:

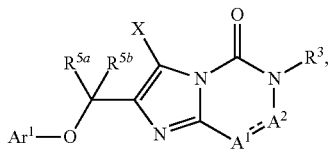

wherein X is halogen; wherein Ar$^1$ is phenyl substituted with 0-3 substituents independently selected from halogen, cyano, C1-C4 alkyl, C1-C4 alkyloxy, C1-C4 monohaloalkyl and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein R$^{1b}$ and R$^{2b}$, when present, are optionally covalently bonded and, together with the intermediate atoms, comprise an optionally substituted 3- to 7-membered fused cycloalkyl; wherein R$^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety Ar$^2$; wherein Ar$^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or Ar$^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein each of R$^{5a}$ and R$^{5b}$ is independently selected from hydrogen, C1-C4 alkyl, C1-C4 monohaloalkyl, and C1-C4 polyhaloalkyl; and (b) reacting the compound with R$^6$OH in the presence of a metal catalyst, wherein R$^6$ is C1-C4 alkyl, thereby forming,

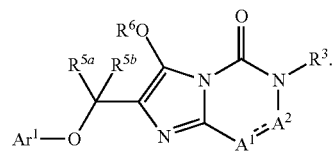

In a further aspect, the metal catalyst comprises palladium, copper, or both. In a still further aspect, the metal catalyst is copper(I)iodide. In a yet further aspect, X is chloro or bromo.

Thus, in one aspect, the invention relates to a method of making a compound comprising the steps of: (a) providing a compound having a structure represented by a formula:

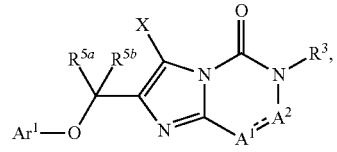

wherein X is halogen; wherein Ar$^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or Ar$^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and A$^1$ and A$^2$ are joined by a covalent double bond, A$^1$ is CR$^{1a}$, and A$^2$ is CR$^{2a}$; wherein R$^{1a}$ is selected from hydrogen, halogen, C1-C4 alkyl, C1-C4 monohaloalkyl, and C1-C4 polyhaloalkyl; wherein R$^{2a}$ is selected from hydrogen, C1-C4 alkyl, C1-C4 monohaloalkyl, and C1-C4 polyhaloalkyl; wherein when ----- is not present and A$^1$ and A$^2$ are joined by a covalent single bond, A$^1$ is CR$^{1b}$R$^{1c}$, and A$^2$ is CR$^{2b}$R$^{2c}$; wherein each of R$^{1b}$ and R$^{1c}$ are independently selected from hydrogen, fluoro, C1-C4 alkyl, C1-C4 monohaloalkyl, and C1-C4 polyhaloalkyl, or R$^{1b}$ and R$^{1c}$ are covalently bonded and, together with the intermediate atoms, comprise an optionally substituted 3- to 7-membered spirocycloalkyl; wherein each of R$^{2b}$ and R$^{2c}$ are independently selected from hydrogen, C1-C4 alkyl, C1-C4 monohaloalkyl, and C1-C4 polyhaloalkyl, or R$^{2b}$ and R$^{2c}$ are covalently bonded and, together with the intermediate atoms, comprise an optionally substituted 3- to 7-membered spirocycloalkyl; wherein R$^{1a}$ and R$^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein each of $R^{5a}$ and $R^{5b}$ is independently selected from hydrogen, C1-C4 alkyl, C1-C4 monohaloalkyl, and C1-C4 polyhaloalkyl; and (b) reacting the compound with $NR^7R^8$ in the presence of a metal catalyst, wherein each of $R^7$ and $R^7$ are independently selected from H and C1-C4 alkyl, thereby forming,

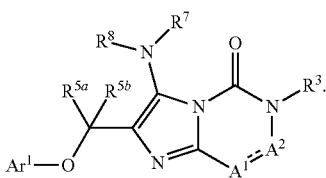

In a further aspect, X is chloro or bromo. In a yet further aspect, the metal catalyst comprises a palladium compound. In an even further aspect, the metal catalyst comprises a palladium compound which is tris(dibenzylideneacetone)dipalladium(0). In a further aspect, the metal catalyst comprises a palladium compound which is tris(dibenzylideneacetone)dipalladium(0):2,2'-Bis(diphenylphosphino)-1,1'-binaphthyl:sodium tert-butoxide.

Thus, in one aspect, the invention relates to a method of making a compound comprising the steps of: (a) providing a compound having a structure represented by a formula:

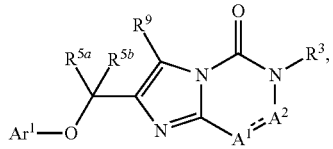

wherein X is halogen; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$;

wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$ is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein each of $R^{5a}$ and $R^{5b}$ is independently selected from hydrogen, C1-C4 alkyl, C1-C4 monohaloalkyl, and C1-C4 polyhaloalkyl; and (b) reacting the compound with $R^9B(OH)_2$ in the presence of a metal catalyst, wherein $R^9$ is selected from C1-C4 alkyl, C1-C4 monohaloalkyl, and C1-C4 polyhaloalkyl thereby forming,

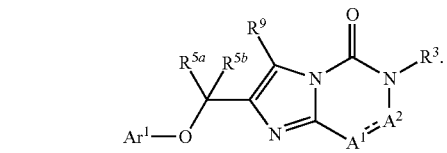

In a further aspect, X is bromo or chloro. In a yet further aspect, the metal catalyst comprises a palladium or copper compound. In a still further aspect, the metal catalyst comprises tris(dibenzylideneacetone)dipalladium(0). In an even further aspect, the metal catalyst comprises tetrakis(triphenylphosphine)palladium(0). In a further aspect, the copper compound is present as copper(I)iodide.

6. Route VI

In one aspect, substituted imidazo[1,2-c]pyrimidin-5(6H)-one analogs of the present invention can be prepared generically as shown below.

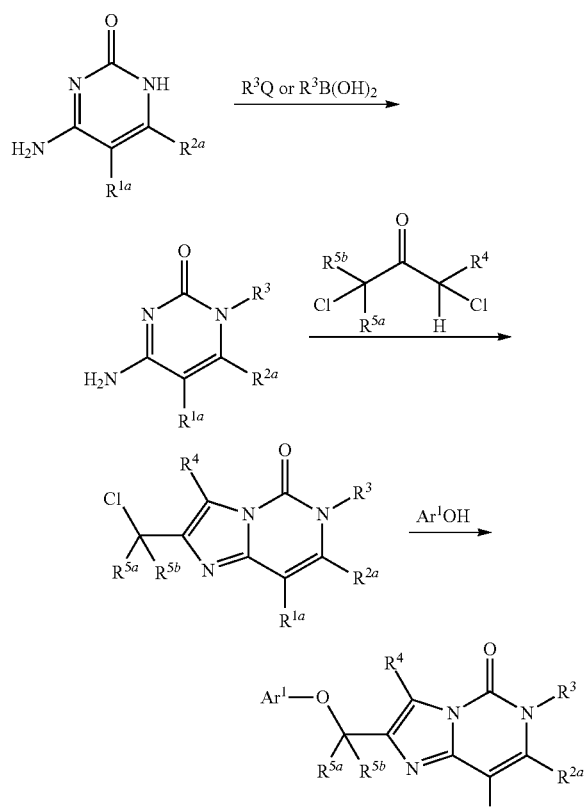
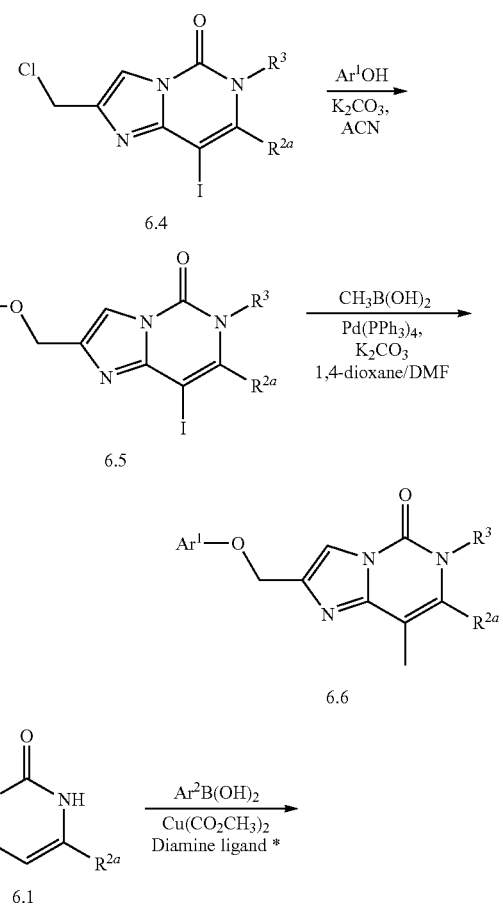
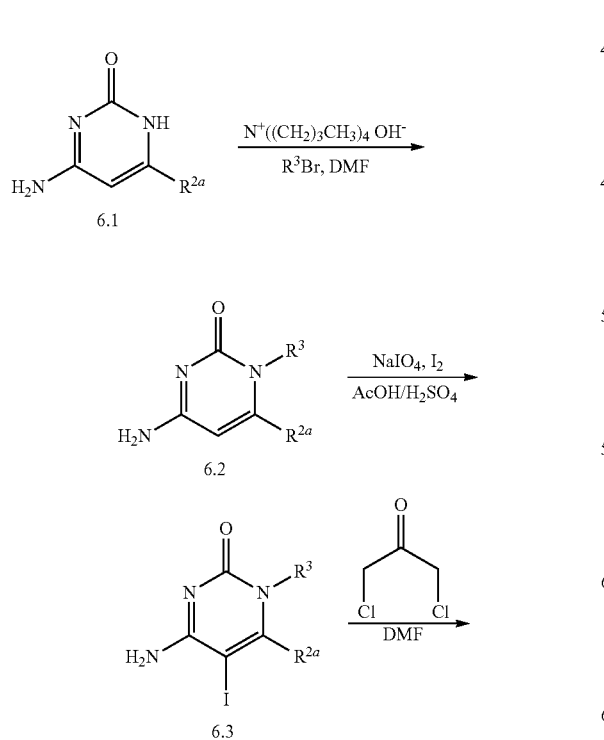
Compounds are represented in generic form, with substituents as noted in compound descriptions elsewhere herein. More specific examples are set forth below.

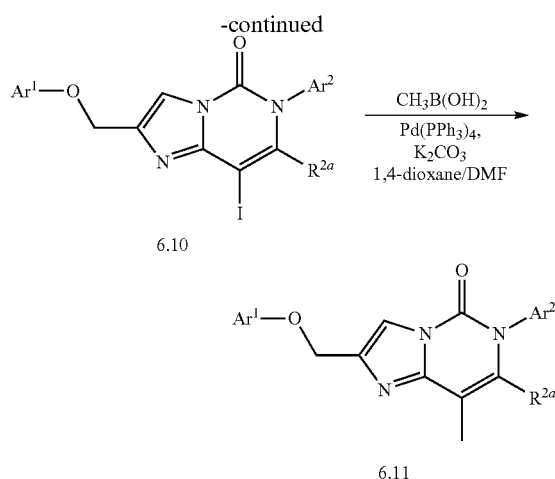

* For example, dimethylethylenediamine

In one aspect, compounds of type 6.6 can be prepared starting with 4-aminopyrimidin-2(1H)-one analogs shown as compound type 6.1. Compound of type 6.1 is reacted with a suitable alkylating compound with an appropriate leaving group, such as $R^3Br$ (although leaving groups other than bromo can also be utilized). The reaction is carried out in the presence of a suitable base, e.g. tetra-N-butylammonium hydroxide, in an inert solvent such as N,N-dimethylformamide at a suitable temperature, e.g. from about 0° C. to about 40° C., for a period of time sufficient to complete the reaction. Similar procedures are described in Eur. J. Med. Chem. (2009) 44:1172-1179. The product of this reaction, compound 6.2, is then reacted with sodium metaperiodate in the presence of iodine in an appropriate mixture of inert solvents, e.g. acetic acid, water and sulfuric acid, at a convenient reaction temperature, e.g. from about 60° C. to about 100° C., for a period of time sufficient to complete the reaction. The compound of type 6.3 is then reacted with a suitable dihaloketone, e.g. 1,2-dichloroacetone, in the presence of an inert solvent, e.g. N,N-dimethylformamide, to afford a compound of type 6.4. This reaction can be carried out by heating with microwave irradiation for a period of time sufficient to insure completion. Conversion of the product, compound 6.4, to a compound of type 6.5 is accomplished by methods described above for Route II. Briefly, the compound is reacted with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction. The compound of type 6.5 is then reacted with methylboronic acid in the presence of an appropriate coupling agent, e.g. tetrakis(triphenylphosphine)palladium(0) and a base, e.g. potassium carbonate. Reactions of this type are typically carried out in a suitable mixture of inert solvents, e.g. 1,4-dioxane and N,N-dimethylformamide. This reaction can be carried out by heating with microwave irradiation for a period of time sufficient to insure completion.

In one aspect, compounds of type 6.11 can be prepared starting with 4-aminopyrimidin-2(1H)-one analogs shown as compound type 6.1. Compound type 6.1 is reacted with an appropriate aryl (including heteroaryl) boronic derivative represented by the formula $Ar^2B(OH)_2$ in the presence of a suitable coupling agent, e.g. copper(II)acetate monohydrate and a suitable ligand, e.g. N,N,N'N'-tetramethylethylenediamine. The reaction is carried out in an inert solvent such as toluene at a suitable temperature, e.g. from about 0° C. to about 40° C. for a period of time sufficient to insure completion of the reaction. Procedures similar to those described in Eur. J. Org. Chem. (2005) 5154-5157 can be used. The product of this reaction, compound 6.7, is then reacted with sodium metaperiodate in the presence of iodine in an appropriate mixture of inert solvents, e.g. acetic acid, water and sulfuric acid, at a convenient reaction temperature, e.g. from about 60° C. to about 100° C., for a period of time sufficient to complete the reaction. The compound of type 6.8 is then reacted with a suitable dihaloketone, e.g. 1,2-dichloroacetone, in the presence of an inert solvent, e.g. N,N-dimethylformamide, to afford a compound of type 6.9. This reaction can be carried out by heating with microwave irradiation for a period of time sufficient to insure completion. Conversion of the product, compound 6.9, to a compound of type 6.10 is accomplished by methods described above for Route II. Briefly, the compound is reacted with a suitable aryl alcohol in the presence of a suitable base, e.g. potassium carbonate, in an inert solvent such as acetonitrile. Reactions of this type are typically carried out at an appropriate reaction temperature, e.g. from about 60° C. to about 100° C., for a period of time sufficient to insure completion of the reaction. The compound of type 6.10 is then reacted with methylboronic acid in the presence of an appropriate coupling agent, e.g., tetrakis(triphenylphosphine)palladium(0) and a base, e.g. potassium carbonate. Reactions of this type are typically carried out in a suitable mixture of inert solvents, e.g. 1,4-dioxane and N,N-dimethylformamide. This reaction can be carried out by heating with microwave irradiation for a period of time sufficient to insure completion.

In a further aspect, the compound produced exhibits positive allosteric modulation of mGluR5 response to glutamate as an increase in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5.

In a further aspect, the compound produced exhibits positive allosteric modulation of mGluR5 (e.g., rmGluR5) with an $EC_{50}$ of less than about 10,000 nM, of less than about 5,000 nM. of less than about 1,000 nM, of less than about 500 nM, or of less than about 100 nM. In a still further aspect, the compound produced exhibits potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a still further aspect, the transfected cell line is the H12H cell line. In a yet further aspect, the compound produced exhibits positive allosteric modulation of mGluR5 (e.g., hmGluR5) with an $EC_{50}$ of less than about 10,000 nM, of less than about 5,000 nM. of less than about 1,000 nM, of less than about 500 nM, or of less than about 100 nM.

In particular, the compound produced exhibits activity in potentiating the mGluR5 receptor in the disclosed assays, generally with an $EC_{50}$ for potentiation of less than about 10 μM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are selective positive allosteric modulators (potentiators) of human and rat mGluR5 compared to the other seven subtypes of metabotropic glutamate receptors.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Table I below lists specific compounds, preferred synthetic route(s), and characterization data. Table II below lists specific compounds with experimentally determined mGluR5 activity determined in a cell-based assay. The mGluR5 activity was determined using the metabotropic glutamate receptor activity assays in human embryonic kidney cells as described herein, wherein the human embryonic kidney cells were transfected with human mGluR5. The compounds in Table I were synthesized with methods identical or analogous to those shown herein. The Synthetic Route Reference indicated in Table I refers to the Reaction Scheme number described above. The requisite starting materials were commercially available, described in the literature, or readily synthesized by one skilled in the art of organic synthesis.

TABLE I

| No. | Structure | Synthetic Route Reference | Parent MW | M + H |
|---|---|---|---|---|
| 1 | 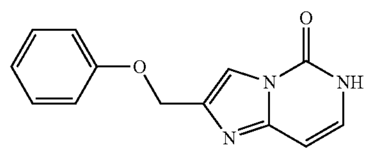 [SMILES: O=c1[nH]ccc2nc(COc3ccccc3)cn12] | IV | 241.1 | 242 |
| 2 | 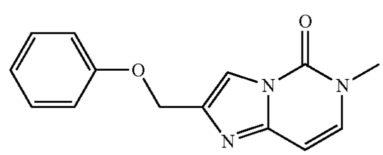 [SMILES: Cn1ccc2nc(COc3ccccc3)cn2c1=O] | II, III | 255.1 | 256 |
| 3 | 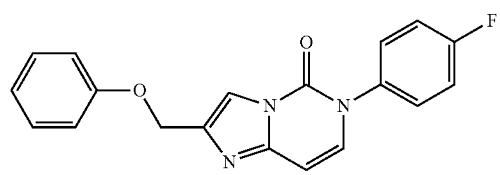 | II, III | 335.1 | 336 |
| 4 | 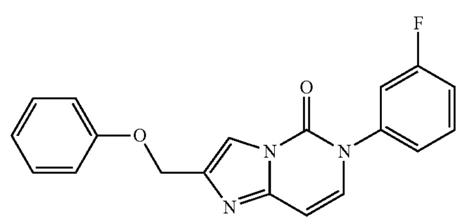 [SMILES: O=c1n(-c2cccc(F)c2)ccc2nc(COc3ccccc3)cn12] | II, III | 335.1 | 336 |
| 5 | 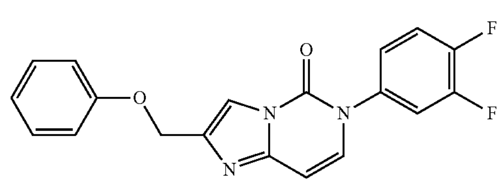 | II, III | 353.1 | 354 |
| 6 | 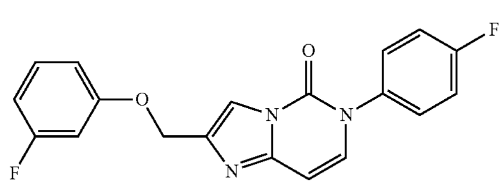 [SMILES: O=c1n(-c2ccc(F)cc2)ccc2nc(COc3cccc(F)c3)cn12] | II, III | 353.1 | 354 |

TABLE I-continued

| No. | Structure | Synthetic Route Reference | Parent MW | M + H |
|-----|-----------|---------------------------|-----------|-------|
| 7   | *structure* | II, III | 331.1 | 332 |
| 8   | *structure* | II, IV  | 332.1 | 333 |
| 9   | *structure* | II, IV  | 336.1 | 337 |
| 10  | *structure* | II, IV  | 350.1 | 351 |
| 11  | *structure* | II, IV  | 332.1 | 333 |
| 12  | *structure* | II, III | 349.1 | 350 |
| 13  | *structure* | II, III | 360.1 | 361 |
| 14  | *structure* | II, III | 353.1 | 354 |

TABLE I-continued

| No. | Structure | Synthetic Route Reference | Parent MW | M + H |
|---|---|---|---|---|
| 15 | 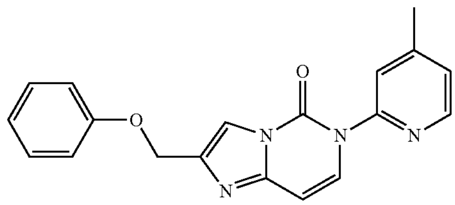 [SMILES: Cc1ccnc(-n2ccc3nc(COc4ccccc4)cn3c2=O)c1] | II, IV | 332.1 | 333 |
| 16 | 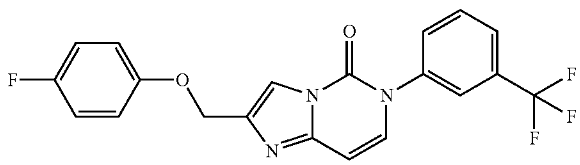 [SMILES: O=c1n(-c2cccc(C(F)(F)F)c2)ccc2nc(COc3ccc(F)cc3)cn12] | II, III | 403.1 | 404 |
| 17 | 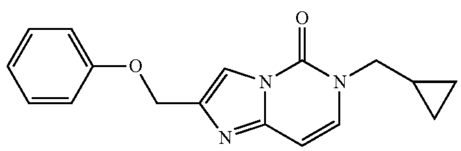 [SMILES: O=c1n(CC2CC2)ccc2nc(COc3ccccc3)cn12] | II, III | 295.1 | 296 |
| 18 | 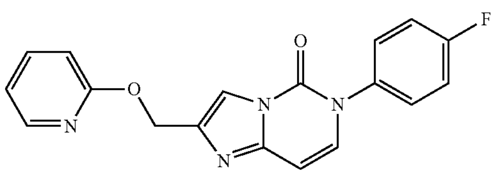 | II, III | 336.1 | 337 |
| 19 | 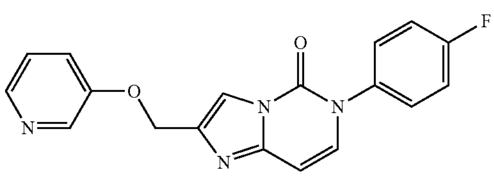 | II, III | 336.1 | 337 |
| 20 | 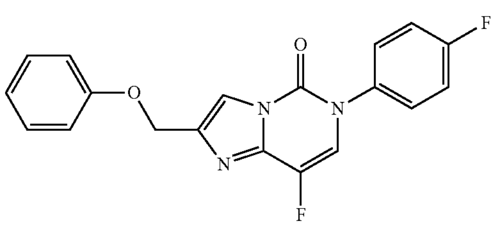 | II, III | 353.1 | 354 |
| 21 | 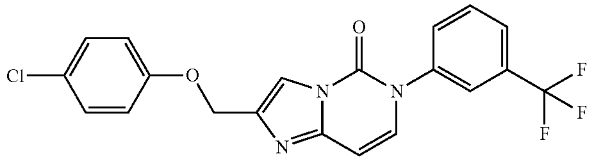 [SMILES: O=c1n(-c2cccc(C(F)(F)F)c2)ccc2nc(COc3ccc(Cl)cc3)cn12] | II, III | 419.1 | 420 |
| 22 | 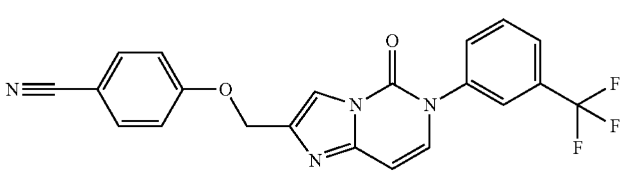 [SMILES: N#Cc1ccc(OCc2cn3c(=O)n(-c4cccc(C(F)(F)F)c4)ccc3n2)cc1] | II, III | 410.1 | 411 |

TABLE I-continued
| No. | Structure | Synthetic Route Reference | Parent MW | M + H |
|---|---|---|---|---|
| 23 | 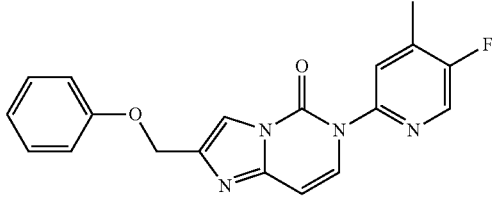 [SMILES: Cc1cc(-n2ccc3nc(COc4ccccc4)cn3c2=O)ncc1F] | II, IV | 350.1 | 351 |
| 24 | 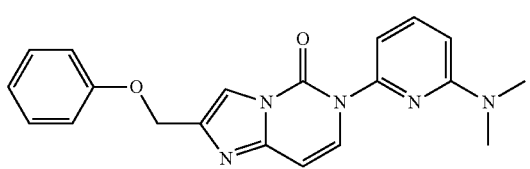 [SMILES: CN(C)c1cccc(-n2ccc3nc(COc4ccccc4)cn3c2=O)n1] | II, IV | 361.1 | 362 |
| 25 | 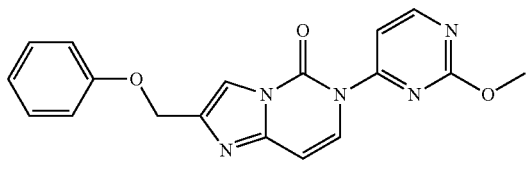 | II, IV | 349.1 | 350 |
| 26 | 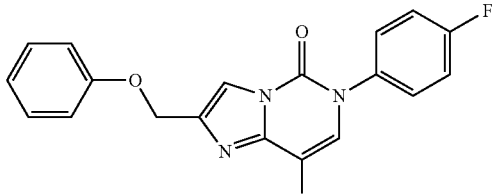 | VI | 461.0 | 462 |
| 27 | 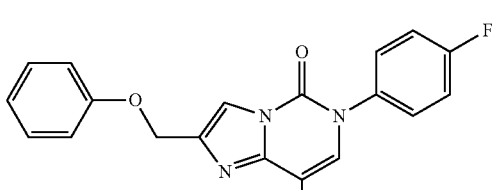 | VI | 349.1 | 350 |
| 28 | 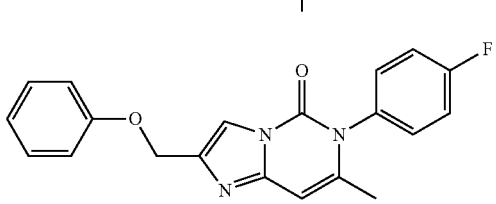 | II, III | 349.1 | 350 |
| 29 | 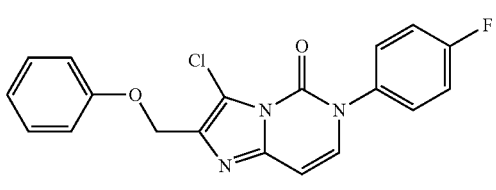 | V | 369.1 | 370 |
| 30 | 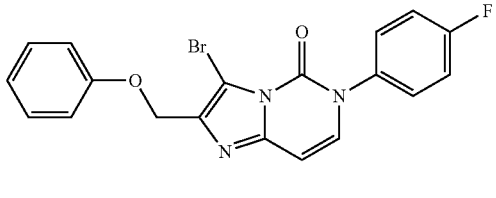 [SMILES: O=c1n(-c2ccc(F)cc2)ccc2nc(COc3ccccc3)c(Br)n12] | V | 413.0 | 414 |

TABLE I-continued

| No. | Structure | Synthetic Route Reference | Parent MW | M + H |
|---|---|---|---|---|
| 31 | 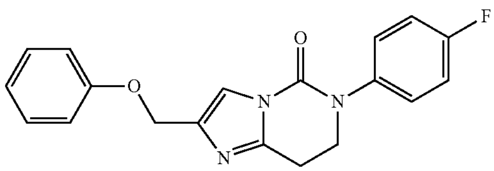 [SMILES: O=C1N(c2ccc(F)cc2)CCc2nc(COc3ccccc3)cn21] | I | 337.1 | 338 |
| 32 | 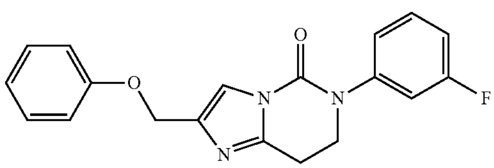 [SMILES: O=C1N(c2cccc(F)c2)CCc2nc(COc3ccccc3)cn21] | I | 337.1 | 338 |
| 33 | 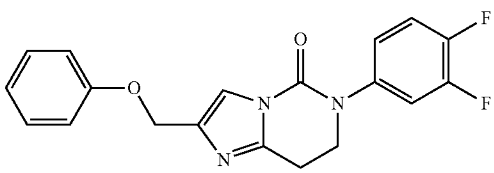 | I | 355.1 | 356 |
| 34 | 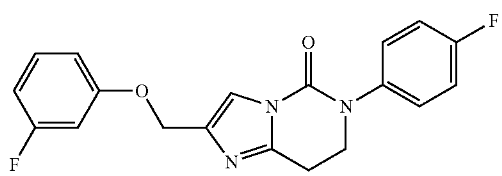 | I | 355.1 | 356 |
| 35 | 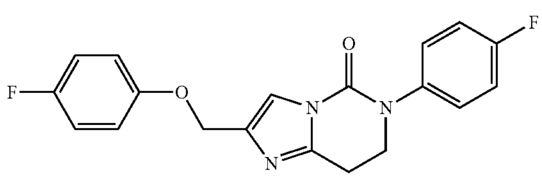 [SMILES: O=C1N(c2ccc(F)cc2)CCc2nc(COc3ccc(F)cc3)cn21] | I | 355.1 | 356 |
| 36 | 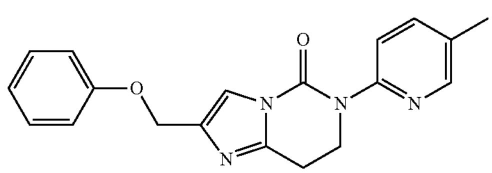 [SMILES: Cc1ccc(N2CCc3nc(COc4ccccc4)cn3C2=O)nc1] | I | 334.1 | 335 |
| 37 | 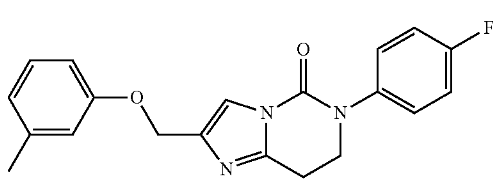 [SMILES: Cc1cccc(OCc2cn3c(n2)CCN(c2ccc(F)cc2)C3=O)c1] | I | 351.1 | 352 |
| 38 | 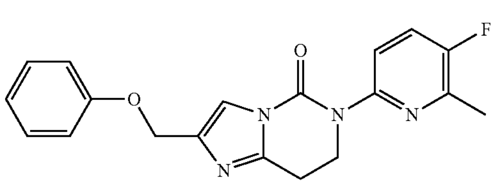 | I | 352.1 | 353 |

TABLE I-continued
| No. | Structure | Synthetic Route Reference | Parent MW | M + H |
|---|---|---|---|---|
| 39 | 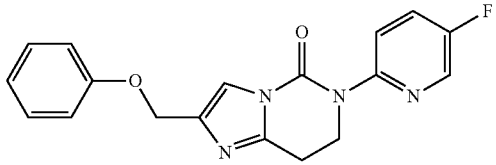 | I | 338.1 | 339 |
| 40 | 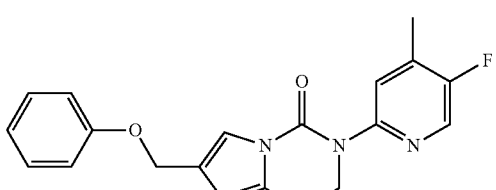 | I | 352.1 | 353 |
| 41 | 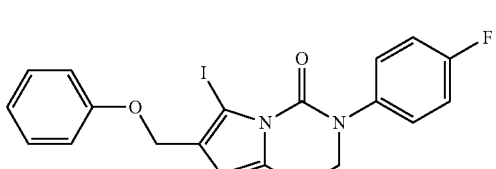 | V | 463.0 | 464 |
| 42 | 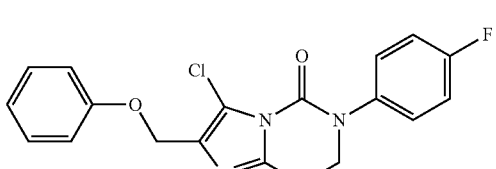 | V | 371.1 | 372 |
| 43 | 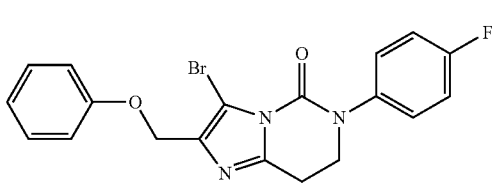 [SMILES: O=C1N(c2ccc(F)cc2)CCc2nc(COc3ccccc3)c(Cl)n21] | V | 415.0 | 416 |
| 44 | 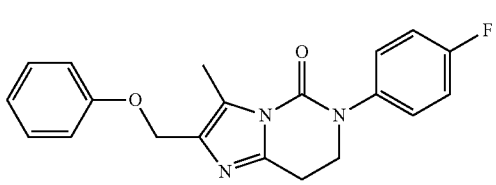 [SMILES: Cc1c(COc2ccccc2)nc2n1C(=O)N(c1ccc(F)cc1)CC2] | V | 351.1 | 352 |
TABLE II
| No. | Structure | $EC_{50}$ (nM) | $pEC_{50}$ | $E_{max}$(%) |
|---|---|---|---|---|
| 1 | 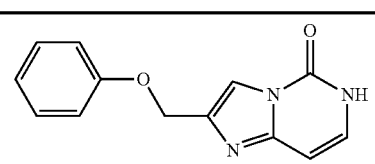 | >30,200 | <4.52 | 19 |
| 2 | 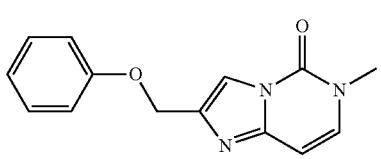 [SMILES: Cn1ccc2nc(COc3ccccc3)cn2c1=O] | >10,000 | <5 | 69 |

TABLE II-continued
| No. | Structure | EC$_{50}$ (nM) | pEC$_{50}$ | E$_{max}$(%) |
|---|---|---|---|---|
| 3 | 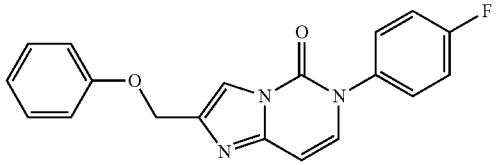 [SMILES: O=c1n(-c2ccc(F)cc2)ccc2nc(COc3ccccc3)cn12] | 392 | 6.57 | 79 |
| 4 | 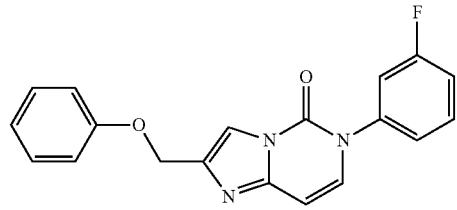 [SMILES: O=c1n(-c2cccc(F)c2)ccc2nc(COc3ccccc3)cn12] | 525 | 6.29 | 68 |
| 5 | 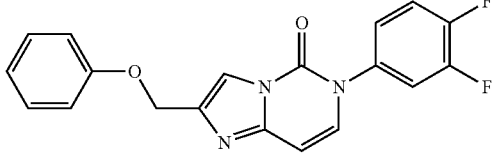 | 228 | 6.67 | 79 |
| 6 | 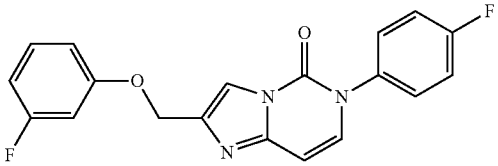 [SMILES: O=c1n(-c2ccc(F)cc2)ccc2nc(COc3cccc(F)c3)cn12] | 224 | 6.67 | 73 |
| 7 | 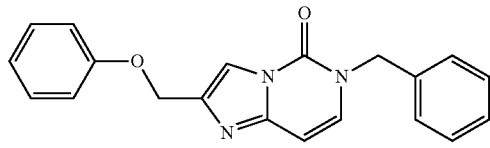 [SMILES: O=c1n(Cc2ccccc2)ccc2nc(COc3ccccc3)cn12] | 1,245 | 5.9 | 80 |
| 8 | 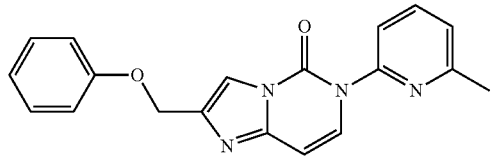 [SMILES: Cc1cccc(-n2ccc3nc(COc4ccccc4)cn3c2=O)n1] | 2,291 | 5.66 | 43 |
| 9 | 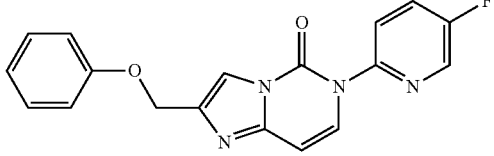 | 490 | 6.31 | 75 |
| 10 | 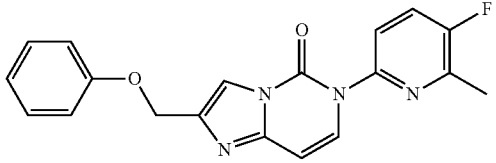 | 292 | 6.5 | 70 |

TABLE II-continued

| No. | Structure | EC$_{50}$ (nM) | pEC$_{50}$ | E$_{max}$(%) |
|---|---|---|---|---|
| 11 | 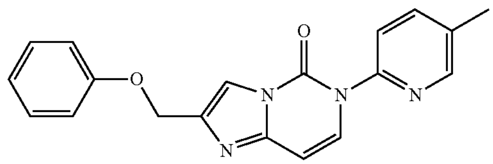 [SMILES: Cc1ccc(-n2ccc3nc(COc4ccccc4)cn3c2=O)nc1] | 1,318 | 5.94 | 59 |
| 12 | 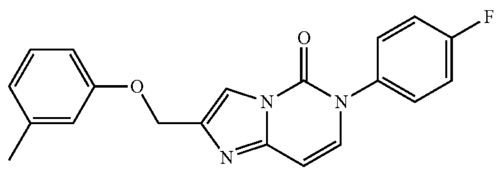 | 468 | 6.29 | 33 |
| 13 | 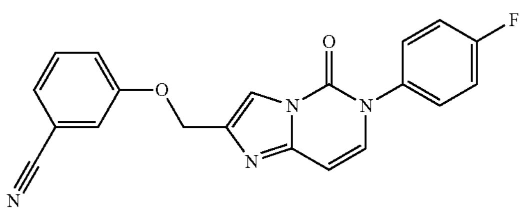 [SMILES: N#Cc1cccc(OCc2cn3c(=O)n(-c4ccc(F)cc4)ccc3n2)c1] | 350 | 6.46 | 40 |
| 14 | 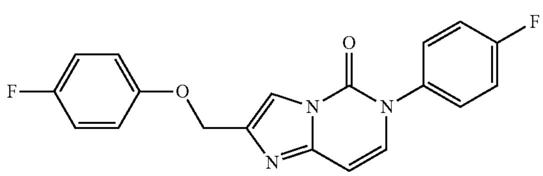 | 302 | 6.51 | 72 |
| 15 | 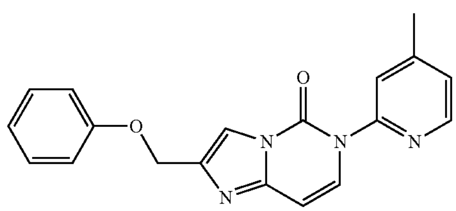 [SMILES: Cc1ccnc(-n2ccc3nc(COc4ccccc4)cn3c2=O)c1] | 8,318 | <5 | 51 |
| 16 | 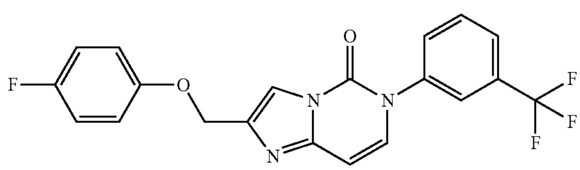 [SMILES: O=c1n(-c2cccc(C(F)(F)F)c2)ccc2nc(COc3ccc(F)cc3)cn12] | 1,288 | 5.93 | 50 |
| 17 | 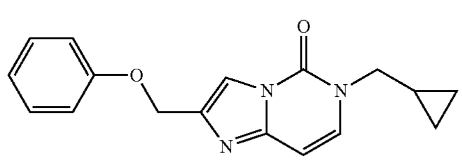 [SMILES: O=c1n(CC2CC2)ccc2nc(COc3ccccc3)cn12] | 1,096 | 5.98 | 51 |
| 18 | 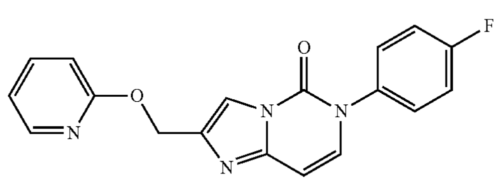 [SMILES: O=c1n(-c2ccc(F)cc2)ccc2nc(COc3ccccn3)cn12] | 2,512 | 5.67 | 66 |

TABLE II-continued
| No. | Structure | EC$_{50}$ (nM) | pEC$_{50}$ | E$_{max}$(%) |
|---|---|---|---|---|
| 19 | 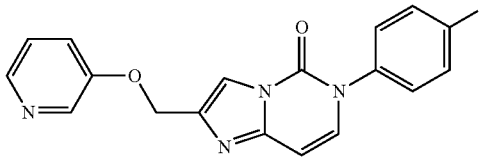 | >30,200 | <4.52 | 59 |
| 20 | 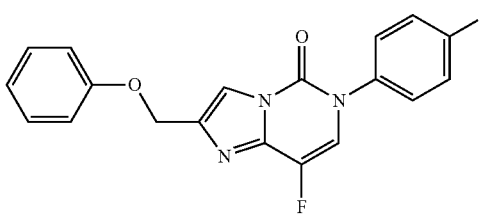 | 78 | 7.07 | 73 |
| 21 | 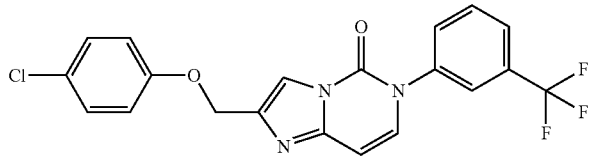 [SMILES: O=c1n(-c2cccc(C(F)(F)F)c2)ccc2nc(COc3ccc(Cl)cc3)cn12] | >10,000 | <5 | — |
| 22 | 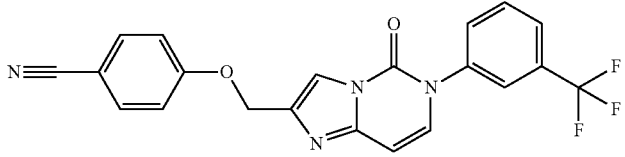 [SMILES: N#Cc1ccc(OCc2cn3c(=O)n(-c4cccc(C(F)(F)F)c4)ccc3n2)cc1] | >10,000 | <5 | — |
| 23 | 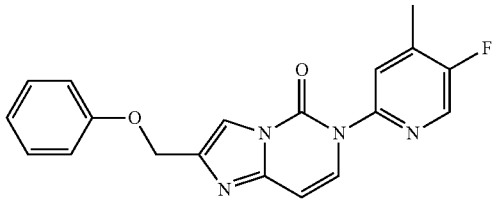 [SMILES: Cc1cc(-n2ccc3nc(COc4ccccc4)cn3c2=O)ncc1F] | 327 | 6.48 | 60 |
| 24 | 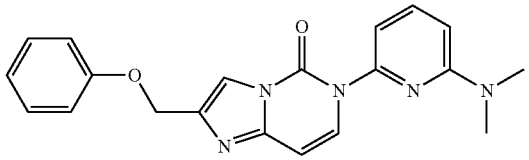 [SMILES: CN(C)c1cccc(-n2ccc3nc(COc4ccccc4)cn3c2=O)n1] | 201 | 6.68 | 64 |
| 25 | 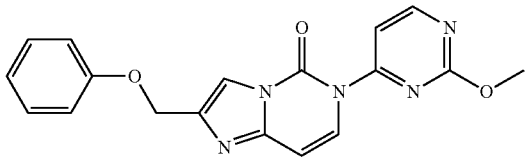 [SMILES: COc1nccc(-n2ccc3nc(COc4ccccc4)cn3c2=O)n1] | 570 | 6.24 | 46 |
| 26 | 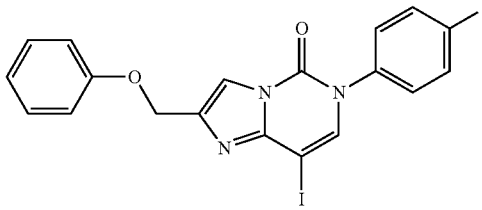 | n.d. | n.d. | n.d. |

TABLE II-continued

| No. | Structure | EC$_{50}$ (nM) | pEC$_{50}$ | E$_{max}$(%) |
|---|---|---|---|---|
| 27 | 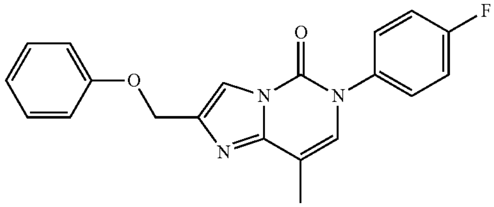 [SMILES: Cc1cn(-c2ccc(F)cc2)c(=O)n2cc(COc3ccccc3)nc12] | >30,200 | <4.52 | 16 |
| 28 | 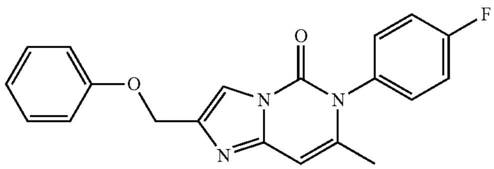 [SMILES: Cc1cc2nc(COc3ccccc3)cn2c(=O)n1-c1ccc(F)cc1] | 1862 | 5.83 | 49 |
| 29 | 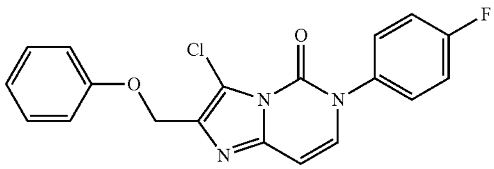 | >30,200 | <4.52 | 17 |
| 30 | 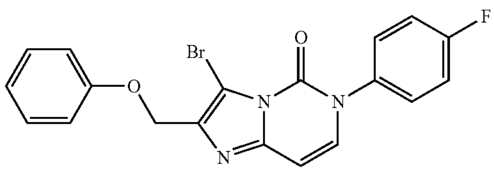 | n.d. | n.d. | n.d. |
| 31 | 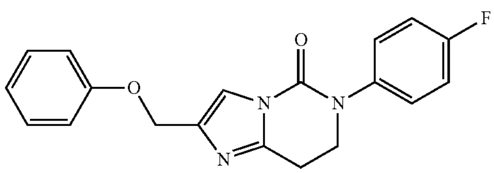 [SMILES: O=C1N(c2ccc(F)cc2)CCc2nc(COc3ccccc3)cn21] | 97 | 6.99 | 71 |
| 32 | 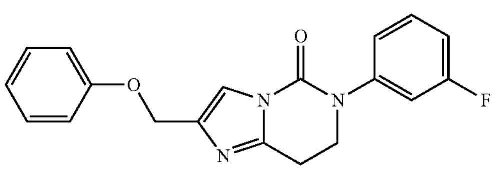 [SMILES: O=C1N(c2cccc(F)c2)CCc2nc(COc3ccccc3)cn21] | 226 | 6.61 | 70 |
| 33 | 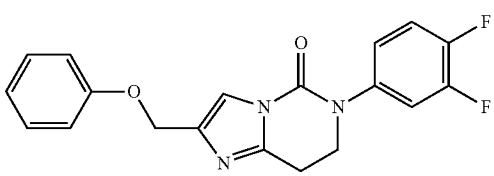 | 97 | 6.99 | 75 |
| 34 | 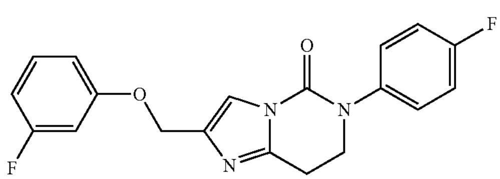 [SMILES: O=C1N(c2ccc(F)cc2)CCc2nc(COc3cccc(F)c3)cn21] | 65 | 7.17 | 73 |

TABLE II-continued

| No. | Structure | EC$_{50}$ (nM) | pEC$_{50}$ | E$_{max}$(%) |
|---|---|---|---|---|
| 35 | 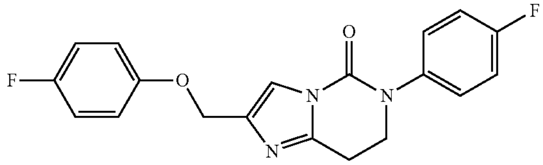 [SMILES: O=C1N(c2ccc(F)cc2)CCc2nc(COc3ccc(F)cc3)cn21] | 188 | 6.77 | 68 |
| 36 | 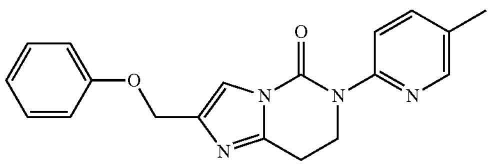 [SMILES: Cc1ccc(N2CCc3nc(COc4ccccc4)cn3C2=O)nc1] | 468 | 6.33 | 63 |
| 37 | 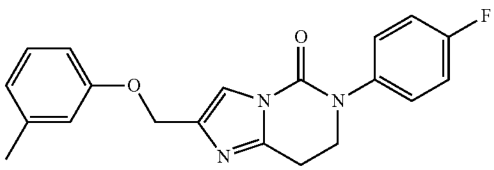 | 191 | 6.69 | 48 |
| 38 | 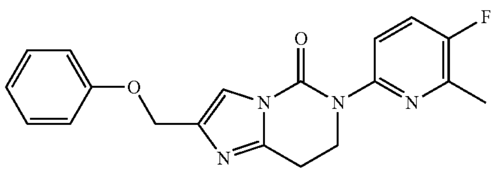 | 166 | 6.75 | 72 |
| 39 | 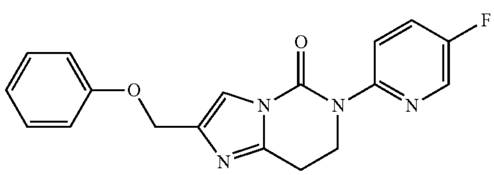 | 389 | 6.50 | 64 |
| 40 | 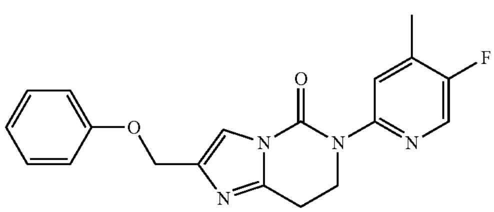 [SMILES: Cc1cc(N2CCc3nc(COc4ccccc4)cn3C2=O)ncc1F] | 351 | 6.57 | 61 |
| 41 | 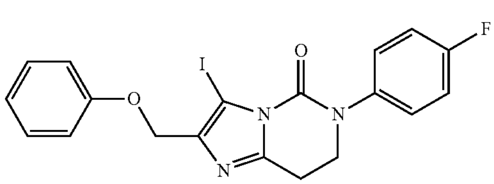 [SMILES: O=C1N(c2ccc(F)cc2)CCc2nc(COc3ccccc3)c(I)n21] | n.d. | n.d. | n.d. |
| 42 | 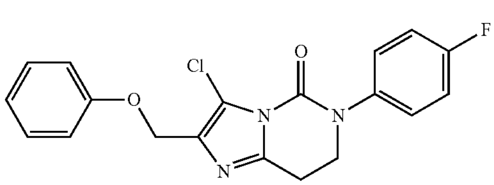 | >30,200 | <4.52 | 17 |

TABLE II-continued

| No. | Structure | EC$_{50}$ (nM) | pEC$_{50}$ | E$_{max}$(%) |
|---|---|---|---|---|
| 43 | [structure] | n.d. | n.d. | n.d. |
| 44 | [structure] | >30,200 | <4.52 | 20 |

"n.d." means not determined

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of Using the Compounds and Compositions

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia general psychosis and cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre-or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through $G\alpha q/11$ to increase inositol phosphate and metabolism and resultant increases in intracellular calcium. Group I mGluRs are primarily located post-synaptically and have a modualtory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to $G\alpha i$ and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et. al. J. Neurosci. 21:5925-5934 (2001)). Therefore, modulation of mGluRs is an approach to modulating glutamatergic transmission. Numerous reports indicate that mGluR5 plays a role in a number of disease states including anxiety (Spooren et. al. J. Pharmacol. Exp. Therapeut. 295:1267-1275 (2000), Tatarczynska et al. Br. J. Pharmaol. 132:1423-1430 (2001)), schizophrenia (reviewed in Chavez-Noriega et al. Curr. Drug Targets: CNS & Neurological Disorders 1:261-281 (2002), Kinney, G. G. et al. J. Pharmacol. Exp. Therapeut. 313:199-206 (2005)), addiction to cocaine (Chiamulera et al. Nature Neurosci. 4:873-874 (2001), Parkinson's disease (Awad et al. J. Neurosci. 20:7871-7879 (2000), Ossowska et al. Neuropharmacol. 41: 413-420 (2001), and pain (Salt and Binns Neurosci. 100: 375-380 (2001).

Figure 2:
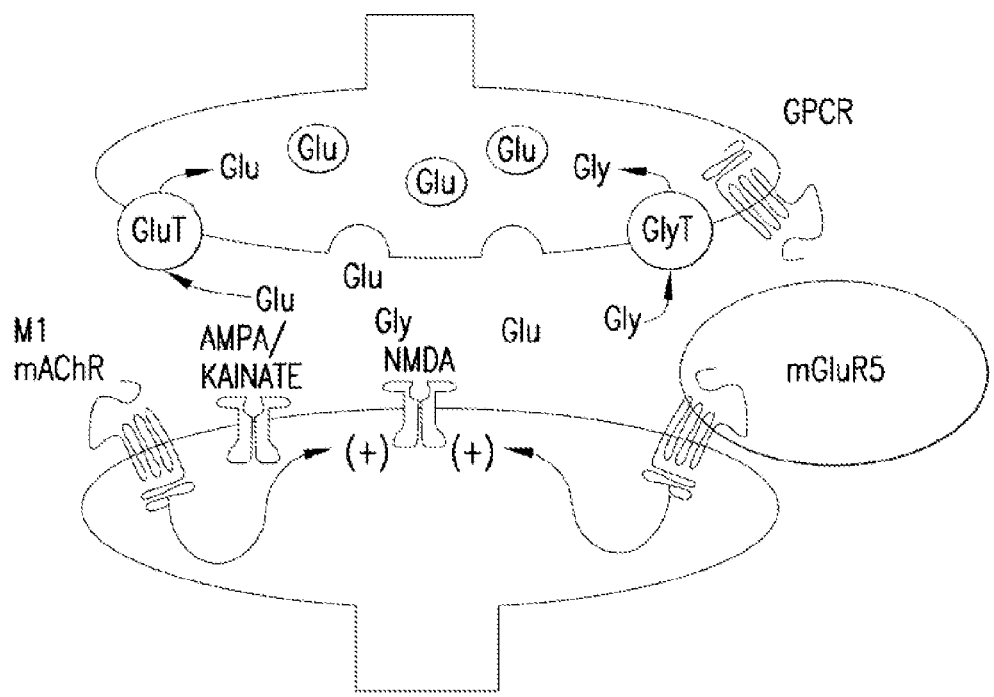
FIG. 2 shows a schematic illustrating that activation of mGluR5 potentiates NMDA receptor function.
Figure 3:
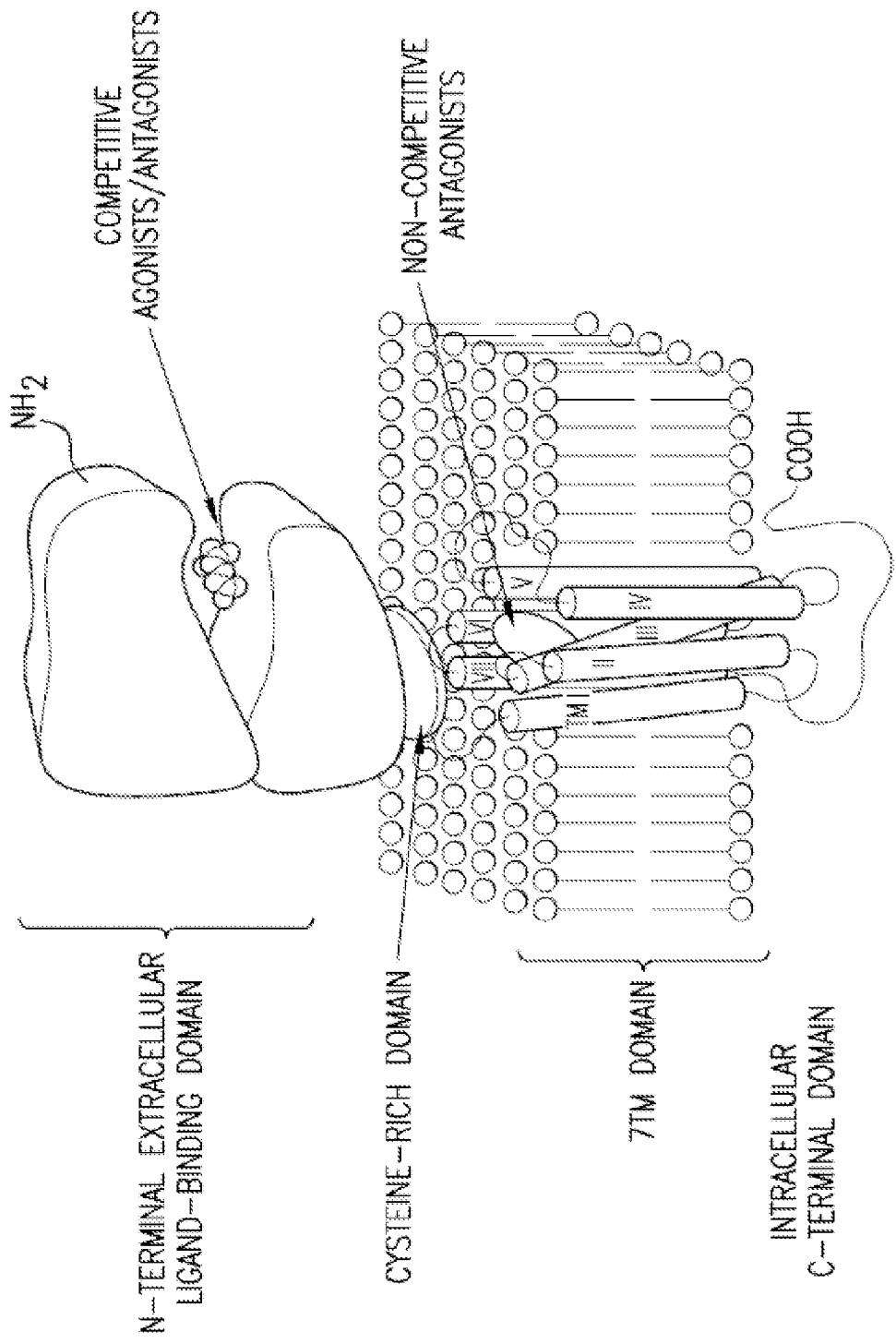
FIG. 3 shows a schematic illustrating structural features of mGluR5 and allosteric binding.

Phencyclidine (PCP) and other NMDA receptor antagonists induce a psychotic state in humans similar to schizophrenia. In schizophrenia patients, PCP and ketamine exacerbate/precipitate preexisting positive and negative symptoms in stable patients. Treatment with NMDA receptor co-agonists can improve positive and negative symptoms. A schematic of the NMDA receptor is shown in FIG. 1. Activation of mGluR5 potentiates NMDA receptor function as shown in FIG. 2. Orthosteric ligands lack subtype selectivity and can cause unwanted side effects. Allosteric modulators (see FIG. 3) that can target transmembrane domains offer a pharmacologically attractive alternative. In one aspect, transmembrane domains can be significantly less conserved than extracellular loop regions.

The compounds disclosed herein are allosteric modulators of metabotropic glutamate receptors, in particular they are positive allosteric modulators of mGluR5. Without wishing to be bound by a particular theory, the The compounds disclosed herein are allosteric modulators of metabotropic glutamate receptors, in particular they are positive allosteric modulators of mGluR5. Again, without wishing to be bound by a particular theory, the compounds disclosed herein do not appear to bind to the glutamate recognition site, the orthosteric ligand site, but instead to an allosteric site. In the presence of glutamate or an agonist of mGluR5, the compounds of this invention increase the mGluR5 response. The compounds disclosed herein are expected to have their effect at mGluR5 by virtue of their ability to increase the response of such receptors to glutamate or mGluR5 agonists, enhancing the response of the receptor.

Hence, the present invention relates compounds disclosed herein for use as a medicament, as well as to the use of a compound disclosed herein or a pharmaceutical composition according to the invention for the manufacture of a medicament, including, for example, the manufacture of a medicament for treating or preventing, in particular treating, a condition in a mammal, including a human, the treatment or prevention of which is affected or facilitated by the neuromodulatory effect of allosteric modulators of mGluR5, e.g. positive allosteric modulators thereof. The present invention also relates to a compound disclosed herein or a pharmaceutical composition according to the invention for use in the treatment or prevention of a condition in a subject such as a mammal, including a human, the treatment or prevention of which is affected or facilitated by the neuromodulatory effect of allosteric modulators of mGluR5, e.g. positive allosteric modulators thereof.

1. Treatment Methods

The compounds disclosed herein are useful for treating, preventing, ameliorating, controlling or reducing the risk of a variety of neurological and psychiatric disorders associated with glutamate dysfunction. In various aspects, the compounds disclosed herein are useful for treating, preventing, ameliorating, controlling or reducing the risk of a variety of neurological and psychiatric disorders associated with glutamate dysfunction, in a subject such as a mammal, including a human, the treatment or prevention of which is affected or facilitated by the neuromodulatory effect of allosteric modulators of mGluR5, e.g. particular positive allosteric modulators thereof. The present invention also relates to the use of a compound disclosed herein or a pharmaceutical composition according to the invention for the manufacture of a medicament for treating, preventing, ameliorating, controlling or reducing the risk of various neurological and psychiatric disorders associated with glutamate dysfunction in a subject such as a mammal, including a human, the treatment or prevention of which is affected or facilitated by the neuromodulatory effect of allosteric modulators of mGluR5, e.g. positive allosteric modulators thereof.

Examples of disorders associated with glutamate dysfunction include: autism, acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Epilepsy can be treated or prevented by the compositions disclosed herein, including absence epilepsy. In various aspects, the compositions disclosed herein can have a protective role for spike and wave discharges associated with absence seizures. Metabotropic glutamate (mGlu) receptors positioned at synapses of the cortico-thalamo-cortical circuitry that generates spike-and-wave discharges (SWDs) associated with absence seizures. Thus, without wishing to be bound by a particular theory, mGluR receptors are therapeutic targets for the treatment of absence epilepsy (e.g. see Epilepsia, 52(7):1211-1222, 2011; Neuropharmacology 60 (2011) 1281e1291; and abstract from 7th International conference on metabotropic glutamate receptors, Oct. 2-6, 2011 Taormina, Italy, "Pharmacological activation of metabotropic glutamate receptor subtype reduces Spike and Wave Discharges in the WAG/Rij rat model of absence epilepsy," I. Santolini, V. D'Amore, C. M. van Rijn, A. Simonyi, A, Prete, P. J. Conn, C. Lindsley, S. Zhou, P. N. Vinson, A. L. Rodriguez, C. K. Jones, S. R. Stauffer, F. Nicoletti, G. van Luijtelaar and R. T. Ngomba).

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, including positive and negative symptoms thereof and cognitive dysfunction related to schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

Thus, provided is a method for treating or preventing schizophrenia, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including schizophrenia and related disorders.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

In various aspects, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

In a further aspect, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

In a further aspect, the central nervous system disorder is a psychotic disorder selected from the group of schizophrenia, delusional disorder, schizoaffective disorder, schizophreniform disorder and substance-induced psychotic disorder In a further aspect, the central nervous system disorder is a personality disorder selected from the group of obsessive-compulsive personality disorder and schizoid, schizotypal disorder.

In a further aspect, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

In a further aspect, the central nervous system disorder is an eating disorder selected from the group of anorexia nervosa and bulimia nervosa.

In a further aspect, the central nervous system disorder is a mood disorder selected from the group of bipolar disorders (I & II), cyclothymic disorder, depression, dysthymic disorder, major depressive disorder and substance-induced mood disorder.

In a further aspect, the central nervous system disorder is migraine.

In a further aspect, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

In a further aspect, the central nervous system disorder is attention-deficit/hyperactivity disorder.

In a further aspect, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a disclosed compound, or a pharmaceutically acceptable salt, including pharmaceutically acceptable acid or base addition salts, hydrate, solvate, polymorphy, or stereoisomeric form thereof, for use in the treatment of any one of the diseases mentioned hereinbefore.

In a further aspect, the invention also relates to a disclosed compound, or a pharmaceutically acceptable salt, including pharmaceutically acceptable acid or base addition salts, hydrate, solvate, polymorphy, or stereoisomeric form thereof, for the treatment or prevention, in particular treatment, of any one of the diseases mentioned hereinbefore.

In a further aspect, the invention relates to relates to a disclosed compound, or a pharmaceutically acceptable salt, including pharmaceutically acceptable acid or base addition salts, hydrate, solvate, polymorphy, or stereoisomeric form thereof, for the manufacture of a medicament for the treatment or prevention of any one of the disease conditions mentioned hereinbefore.

In a further aspect, the invention also relates to the use of relates to a disclosed compound, or a pharmaceutically acceptable salt, including pharmaceutically acceptable acid or base addition salts, hydrate, solvate, polymorphy, or stereoisomeric form thereof, for the manufacture of a medicament for the treatment of any one of the disease conditions mentioned hereinbefore.

In a further aspect, the invention relates to a disclosed compound, or a pharmaceutically acceptable salt, including pharmaceutically acceptable acid or base addition salts, hydrate, solvate, polymorphy, or stereoisomeric form thereof, administered to mammals, e.g. humans, for the treatment or prevention of any one of the diseases mentioned hereinbefore.

In a further aspect, relates to a method of treating warm-blooded animals, such as mammals including humans, suffering from any one of the diseases mentioned hereinbefore, and a method of preventing in warm-blooded animals, such as mammals including humans, any one of the diseases mentioned hereinbefore by administering a disclosed compound, or a pharmaceutically acceptable salt, including pharmaceutically acceptable acid or base addition salts, hydrate, solvate, polymorphy, or stereoisomeric form thereof. Said methods comprise the administration, i.e. the systemic or topical administration, preferably oral administration, of a therapeutically effective amount of a disclosed compound, or a pharmaceutically acceptable salt, including pharmaceutically acceptable acid or base addition salts, hydrate, solvate, polymorphy, or stereoisomeric form thereof, to warm-blooded animals, such as mammals including humans.

In various aspects, the invention also relates to a method for the prevention and/or treatment of any one of the diseases mentioned hereinbefore comprising administering a therapeutically effective amount of a disclosed compound, or a pharmaceutically acceptable salt, including pharmaceutically acceptable acid or base addition salts, hydrate, solvate, polymorphy, or stereoisomeric form thereof, to a patient in need thereof.

In various aspects, a disclosed compound is a positive allosteric modulators of mGluR5, and can enhance the response of mGluR5 to glutamate, thus it is an advantage that the present methods utilize endogenous glutamate. In a further aspect, positive allosteric modulators of mGluR5, such as the disclosed compounds, enhance the response of mGluR5 to agonists, it is understood that the present invention extends to the treatment of neurological and psychiatric disorders associated with glutamate dysfunction by administering an effective amount of a disclosed compound, or a pharmaceutically acceptable salt, including pharmaceutically acceptable acid or base addition salts, hydrate, solvate, polymorphy, or stereoisomeric form thereof, in combination with an mGluR5 agonist.

The compounds of the present invention may be utilized in combination with one or more other drugs in the treatment, prevention, control, amelioration, or reduction of risk of diseases or conditions for which a disclosed compound, or a pharmaceutically acceptable salt, including pharmaceutically acceptable acid or base addition salts, hydrate, solvate, polymorphy, or stereoisomeric form thereof, or the other drugs may have utility, where the combination of the drugs together are safer or more effective than either drug alone.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with anti-Alzheimer's agents, beta-secretase inhibitors, gamma-secretase inhibitors, muscarinic agonists, muscarinic potentiatorsHMG-CoA reductase inhibitors, NSAIDs and anti-amyloid antibodies.

In another aspect, the subject compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

In another aspect, the subject compound can be used in combination with levodopa (with or without a selective extracerebral decarboxylase inhibitor), anticholinergics such as biperiden, COMT inhibitors such as entacapone, A2a adenosine antagonists, cholinergic agonists, NMDA receptor antagonists and dopamine agonists.

The pharmaceutical compositions and methods of the present invention can further comprise other therapeutically active compounds as noted herein which are usually applied in the treatment of the above mentioned pathological conditions.

a. Treatment of a Neurological and/or Psychiatric Disorder Associated With Glutamate Dysfunction In one aspect, the invention relates to a method for the treatment of a disorder associated with mGluR5 activity in a mammal comprising the step of administering to the mammal at least one disclosed compound or at least one disclosed product in a dosage and amount effective to treat the disorder in the mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In one aspect, the invention relates to a method for the treatment of a neurological and/or psychiatric disorder associated with glutamate dysfunction in a mammal comprising the step of administering to the mammal a therapeutically effective amount of at least one compound having a structure represented by a formula:

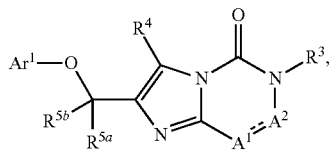

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

b. Treatment of a Disease of Uncontrolled Cellular Proliferation

In one aspect, the invention relates to a method for the treatment of a disease of uncontrolled cellular proliferation in a mammal comprising the step of administering to the mammal at least one disclosed compound or at least one disclosed product in a dosage and amount effective to treat the disease in the mammal. In a further aspect, the mammal is a human. In a further aspect, the mammal has been diagnosed with a need for treatment of the disease prior to the administering step. In a further aspect, the method further comprises the step of identifying a mammal in need of treatment of the disease.

In a further aspect, the disorder is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

c. Potentiation of Metabotropic Glutamate Receptor Activity

In one aspect, the invention relates to a method for potentiation of mGluR5 activity in a mammal comprising the step of administering to the mammal at least one disclosed compound or at least one disclosed product in a dosage and amount effective to increase mGluR5 activity in the mammal either in the presence or absence of the endogenous ligand. In a further aspect, the mammal is a human. In a further aspect, the mammal has been diagnosed with a need for increasing mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of increasing mGluR5 activity.

In one aspect, the invention relates to a method for potentiation of metabotropic glutamate receptor activity in a mammal comprising the step of administering to the mammal a therapeutically effective amount of at least one compound having a structure represented by a formula:

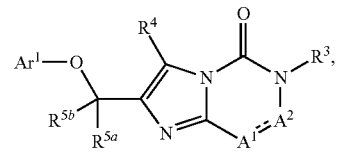

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In various aspects, the invention relates to a method for potentiation of metabotropic glutamate receptor activity in a mammal comprising the step of administering to the mammal at least one disclosed compound or at least one disclosed product in a dosage and amount effective to increase metabotropic glutamate receptor activity in the mammal either in the presence or absence of the endogenous ligand.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In a further aspect, the compound exhibits potentiation of mGluR5 with an $EC_{50}$ of less than about 10,000 nM. In a still further aspect, the compound exhibits potentiation of mGluR5 with an $EC_{50}$ of less than about 5,000 nM. In an even further aspect, the compound exhibits potentiation of mGluR5 with an $EC_{50}$ of less than about 1,000 nM. In a further aspect, the compound exhibits potentiation of mGluR5 with an $EC_{50}$ of less than about 500 nM. In a yet further aspect, the compound exhibits potentiation of mGluR5 with an $EC_{50}$ of less than about 100 nM.

In a further aspect, the compound exhibits potentiation of mGluR5 with an $EC_{50}$ of between about 10,000 nM to about 1 nM. In a still further aspect, the compound exhibits potentiation of mGluR5 with an $EC_{50}$ of between about 1,000 nM to about 1 nM. In a yet further aspect, the compound exhibits potentiation of mGluR5 with an $EC_{50}$ of between about 100 nM to about 1 nM. In an even further aspect, the compound exhibits potentiation of mGluR5 with an $EC_{50}$ of between about 10 nM to about 1 nM. In a still further aspect, potentiation of mGluR5 activity is positive allosteric modulation of mGluR5 activity.

In one aspect, the mammal is a human. In a further aspect, the mammal has been diagnosed with a need for potentiation of metabotropic glutamate receptor activity prior to the administering step. In a further aspect, the method further comprises comprising the step of identifying a mammal in need for potentiation of metabotropic glutamate receptor activity. In a further aspect, the metabotropic glutamate receptor is mGluR5.

In a yet further aspect, the potentiation of mGluR5 activity treats a disorder associated with mGluR5 activity in the mammal. In a still further aspect, the mammal has been diagnosed with a need for treatment of the disorder prior to the administering step. In an even further aspect, treatment further comprises the step of identifying a mammal in need of treatment of the disorder.

In a further aspect, potentiation of metabotropic glutamate receptor activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, potentiation of metabotropic glutamate receptor activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

d. Partial Agonism of Metabotropic Glutamate Receptor Activity

In one aspect, the invention relates to a method for partial agonism of metabotropic glutamate receptor activity in a mammal. In a further aspect, the method relates to a method for partial agonism of metabotropic glutamate receptor activity in a mammal by contacting at least one cell in the mammal, comprising the step of contacting the at least one cell with at least one disclosed compound or at least one disclosed product in an amount effective to inhibit mGluR5 activity in the at least one cell.

In one aspect, the invention relates to a method for partial agonism of metabotropic glutamate receptor activity in a mammal comprising the step of administering to the mammal a therapeutically effective amount of at least one compound having a structure represented by a formula:

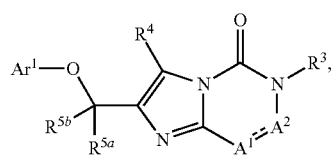

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, A1 is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In a further aspect, the mammal has been diagnosed with a need for partial agonism of metabotropic glutamate receptor activity prior to the administering step. In a still further aspect, the method further comprises the step of identifying a mammal in need for partial agonism of metabotropic glutamate receptor activity. In a yet further aspect, the metabotropic glutamate receptor is mGluR5.

In a further aspect, partial agonism of metabotropic glutamate receptor activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, partial agonism of metabotropic glutamate receptor activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

e. Enhancing Cognition

In one aspect, the invention relates to a method for enhancing cognition in a mammal comprising the step of administering to the mammal an effective amount of at least one disclosed compound.

In one aspect, the invention relates to a method for enhancing cognition in a mammal comprising the step of administering to the mammal an effective amount of at least one compound having a structure represented by a formula:

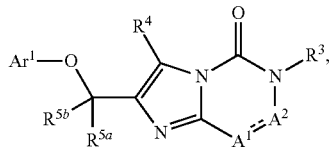

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, A1 is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In one aspect, the mammal has been diagnosed with a need for cognition enhancement prior to the administering step. In a still further aspect, the method further comprises the step of identifying a mammal in need of cognition enhancement prior to the administering step. In a further aspect, the cognition enhancement is a statistically significant increase in Novel Object Recognition. In a further aspect, the cognition enhancement is a statistically significant increase in performance of the Wisconsin Card Sorting Test. In a further aspect, the method further comprises the step of identifying a mammal in need of increasing mGluR5 activity.

f. Modulating mGluR5 Activity in Mammals

In one aspect, the invention relates to a method for modulating mGluR5 activity in a mammal comprising the step of administering to the mammal an effective amount of at least one disclosed compound.

In one aspect, the invention relates to a method for modulating mGluR5 activity in a mammal comprising the step of administering to the mammal an effective amount of at least one compound having a structure represented by a formula:

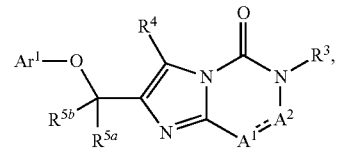

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, A1 is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In a further aspect, the compound exhibits positive allosteric modulation of mGluR5 with an EC$_{50}$ of less than about 10,000 nM. In a still further aspect, the compound exhibits positive allosteric modulation of mGluR5 with an EC$_{50}$ of less than about 5,000 nM. In an even further aspect, the compound exhibits positive allosteric modulation of mGluR5 with an EC$_{50}$ of less than about 1,000 nM. In a further aspect, the compound exhibits positive allosteric modulation of mGluR5 with an EC$_{50}$ of less than about 500 nM. In a yet further aspect, the compound exhibits positive allosteric modulation of mGluR5 with an EC$_{50}$ of less than about 100 nM.

In one aspect, modulating is increasing. In a further aspect, modulating is potentiation. In a further aspect, modulating is partial agonism.

In one aspect, the mammal is a human. In a further aspect, the mammal has been diagnosed with a need for modulating mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of increasing mGluR5 activity.

In one aspect, an effective amount is a therapeutically effective amount.

In a further aspect, modulating mGluR5 activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, modulating mGluR5 activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

g. Modulating mGluR5 Activity in Cells

In one aspect, the invention relates to a method for modulating mGluR5 activity in at least one cell, comprising the step of contacting the at least one cell with an effective amount of at least one disclosed compound.

In one aspect, the invention relates to a method for modulating mGluR5 activity in at least one cell, comprising the step of contacting the at least one cell with an effective amount of at least one compound having a structure represented by a formula:

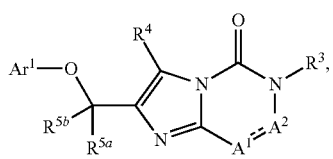

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, A1 is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In a further aspect, the compound exhibits potentiation of mGluR5 with an $EC_{50}$ of less than about 10,000 nM. In a still further aspect, the compound exhibits potentiation of mGluR5 with an $EC_{50}$ of less than about 5,000 nM. In an even further aspect, the compound exhibits potentiation of mGluR5 with an $EC_{50}$ of less than about 1,000 nM. In a further aspect, the compound exhibits potentiation of mGluR5 with an $EC_{50}$ of less than about 500 nM. In a yet further aspect, the compound exhibits potentiation of mGluR5 with an $EC_{50}$ of less than about 100 nM.

In a further aspect, the compound exhibits potentiation of mGluR5 with an $EC_{50}$ of between about 10,000 nM to about 1 nM. In a still further aspect, the compound exhibits potentiation of mGluR5 with an $EC_{50}$ of between about 1,000 nM to about 1 nM. In a yet further aspect, the compound exhibits potentiation of mGluR5 with an $EC_{50}$ of between about 100 nM to about 1 nM. In an even further aspect, the compound exhibits potentiation of mGluR5 with an $EC_{50}$ of between about 10 nM to about 1 nM. In a still further aspect, potentiation of mGluR5 activity is positive allosteric modulation of mGluR5 activity.

In one aspect, modulating is increasing. In a further aspect, modulating is potentiation. In a further aspect, modulating is partial agonism.

In one aspect, the cell is mammalian. In a further aspect, the cell is human. In a further aspect, the cell has been isolated from a mammal prior to the contacting step.

In a further aspect, contacting is via administration to a mammal. In a further aspect, the mammal has been diagnosed with a need for modulating mGluR5 activity prior to the administering step. In a further aspect, the mammal has been diagnosed with a need for treatment of a disorder related to mGluR5 activity prior to the administering step.

In one aspect, modulating mGluR5 activity in at least one cell treats a neurological and/or psychiatric disorder. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, modulating mGluR5 activity in at least one cell treats a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

2. Cotherapeutic Methods

The present invention is further directed to administration of a mGluR5 potentiator for improving treatment outcomes in the context of cognitive or behavioral therapy. That is, in one aspect, the invention relates to a cotherapeutic method comprising the step of administering to a mammal an effective amount of at least one disclosed compound; at least one product of a disclosed method of making; or a pharmaceutically effective salt, hydrate, solvate, or polymorph thereof.

In a further aspect, the mammal is a human. In a still further aspect, an effective amount is a therapeutically effective amount. In a yet further aspect, an effective amount is a prophylatically effective amount. In an even further aspect, treatment is symptom amelioration or prevention, and wherein an effective amount is a prophylatically effective amount.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, or 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound. It is understood that the disclosed cotherapeutic methods can be used in connection with the disclosed compounds, compositions, kits, and uses.

3. Manufacture of a Medicament

In one aspect, the invention relates to a method for the manufacture of a medicament for potentiation of metabotropic glutamate receptor activity in a mammal comprising combining a therapeutically effective amount of a disclosed compound or product of a disclosed method with a pharmaceutically acceptable carrier or diluent.

In various aspect, the invention relates methods for the manufacture of a medicament for modulating the activity mGluR5 (e.g., treatment of one or more neurological and/or psychiatric disorder associated with mGluR5 dysfunction) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

4. Use of Compounds

In one aspect, the invention relates to the use of a disclosed compound or a product of a disclosed method of making. In a further aspect, the use relates to the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation. In a further aspect, a use relates to treatment of a neurological and/or psychiatric disorder associated with glutamate dysfunction in a mammal.

In a further aspect, a use relates to potentiation of metabotropic glutamate receptor activity in a mammal. In a further aspect, a use relates to partial agonism of metabotropic glutamate receptor activity in a mammal. In a further aspect, a use relates to enhancing cognition in a mammal. In a further aspect, a use relates to modulating mGluR5 activity in a mammal. In a further aspect, a use relates to modulating mGluR5 activity in a cell.

In one aspect, a use is treatment of a neurological and/or psychiatric disorder associated with mGluR5 dysfunction. In a further aspect, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In one aspect, a use is associated with the treatment of a disorder associated with uncontrolled cellular proliferation. In a further aspect, the disorder is cancer. In a still further aspect, the cancer is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

In one aspect, the invention relates to the use of a disclosed compound or a disclosed product in the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation.

In one aspect, the invention relates to the use of a disclosed compound or a product of a disclosed method of making, or a pharmaceutically acceptable salt, solvate, or polymorph thereof, or a pharmaceutical composition for use in treating or preventing a central nervous system disorder selected from the group of psychotic disorders and conditions; anxiety disorders; movement disorders; drug abuse; mood disorders; neurodegenerative disorders; disorders or conditions comprising as a symptom a deficiency in attention and/or cognition; pain and diseases of uncontrolled cellular proliferation. In a further aspect, the invention relates to the use of a disclosed compound or a product of a disclosed method of making, or a pharmaceutically acceptable salt, solvate, or polymorph thereof, or a pharmaceutical composition for use wherein the psychotic disorders and conditions are selected from the group of schizophrenia; schizophreniform disorder; schizoaffective disorder; delusional disorder; substance-induced psychotic disorder; personality disorders of the paranoid type; and personality disorder of the schizoid type; the anxiety disorders are selected from the group of panic disorder; agoraphobia; specific phobia; social phobia; obsessive-compulsive disorder; post-traumatic stress disorder; acute stress disorder; and generalized anxiety disorder; the movement disorders are selected from the group of Huntington's disease; dyskinesia; Parkinson's disease; restless leg syndrome and essential tremor; Tourette's syndrome and other tic disorders; the substance-related disorders are selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal; the mood disorders are selected from depression, mania and bipolar disorder of types I and II; cyclothymic disorder; depression; dysthymic disorder; major depressive disorder and substance-induced mood disorder; the neurodegenerative disorders are selected from the group of Parkinson's disease; Huntington's disease; dementia such as for example Alzheimer's disease; multi-infarct dementia; AIDS-related dementia or frontotemporal dementia; the disorders or conditions comprising as a symptom a deficiency in attention and/or cognition are selected from the group of dementia, such as Alzheimer's disease; multi-infarct dementia; dementia due to Lewy body disease; alcoholic dementia or substance-induced persisting dementia; dementia associated with intracranial tumors or cerebral trauma; dementia associated with Huntington's disease; dementia associated with Parkinson's disease; AIDS-related dementia; dementia due to Pick's disease; dementia due to Creutzfeldt-Jakob disease; delirium; amnestic disorder; post-traumatic stress disorder; stroke; progressive supranuclear palsy; mental retardation; a learning disorder; attention-deficit/hyperactivity disorder (ADHD); mild cognitive disorder; Asperger's syndrome; and age-related cognitive impairment; pain includes acute and chronic states, severe pain, intractable pain, neuropathic pain and post-traumatic pain, cancer pain, non-cancer pain, pain disorder associated with psychological factors, pain disorder associated with a general medical condition or pain disorder associated with both psychological factors and a general medical condition; the diseases of uncontrolled cellular proliferation are selected from lymphoma, cancers of the brain, genitourinary tract cancer, lymphatic cancer, stomach cancer, larynx cancer, lung cancer, pancreatic cancer, breast cancer, and malignant melanoma.

In one aspect, the invention relates to the use of a disclosed compound or a product of a disclosed method of making, or a pharmaceutically acceptable salt, solvate, or polymorph thereof, or a pharmaceutical composition, in combination with an additional pharmaceutical agent for use in the treatment or prevention of a central nervous system disorder selected from the group of psychotic disorders and conditions; anxiety disorders; movement disorders; drug abuse; mood disorders; neurodegenerative disorders; disorders or conditions comprising as a symptom a deficiency in attention and/or cognition; pain and diseases of uncontrolled cellular proliferation.

In one aspect, the invention relates to a process for preparing a pharmaceutical composition comprising a therapeutically effective amount of a disclosed compound or a product of a disclosed method of making, or a pharmaceutically acceptable salt, solvate, or polymorph thereof, characterized in that a pharmaceutically acceptable carrier is intimately mixed with a therapeutically effective amount of the compound or the product of a disclosed method of making.

In a further aspect, the invention relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

5. Kits

In one aspect, the invention relates to a kit comprising a disclosed compound or a product of a disclosed method and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, the at least one compound or the at least one product and the at least one agent are co-formulated. In a further aspect, the at least one compound or the at least one product and the at least one agent are co-packaged.

In various aspects, the invention relates to products and kits containing as a first active ingredient a compound according to the invention, as defined herein, and as a second active ingredient one or more components, as combined preparations for simultaneous, separate, or sequential use in the treatment of a neurological and/or psychiatric disorder. In a further aspect, the invention relates to products and kits containing as a first active ingredient a compound according to the invention, as defined herein, and as a second active ingredient one or more components, as combined preparations for simultaneous, separate, or sequential use in the treatment of a disease of uncontrolled cellular proliferation. In a still further aspect, the invention relates to products and kits containing as a first active ingredient a compound according to the invention, as defined herein, and as a second active ingredient one or more components, as combined preparations for simultaneous, separate, or sequential use in the treatment of a disease related to a need to increase mGluR5 activity. In an even further aspect, the invention relates to products and kits containing as a first active ingredient a compound according to the invention, as defined herein, and as a second active ingredient one or more components, as combined preparations for simultaneous, separate, or sequential use in the treatment of a disease related to a metabotropic glutamate receptor dysfunction.

In one aspect, the invention relates to a kit comprising at least one compound having a structure represented by a formula:

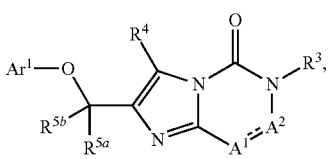

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2c}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof; and one or more of: (a) at least one agent known to increase mGluR5 activity; (b) at least one agent known to decrease mGluR5 activity; (c) at least one agent known to treat a neurological and/or psychiatric disorder; (d) at least one agent known to treat a disease of uncontrolled cellular proliferation; or (e) instructions for treating a disorder associated with glutamate dysfunction.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

6. Non-Medical Uses

Also provided are the uses of the disclosed compounds and products as pharmacological tools in the development and standardization of in vitro and in vivo test systems for the evaluation of the effects of potentiators of mGluR5 related activity in laboratory animals such as cats, dogs, rabbits, monkeys, rats and mice, as part of the search for new therapeutic agents of mGluR5. In a further aspect, the invention relates to the use of a disclosed compound or a disclosed product as pharmacological tools in the development and standardization of in vitro and in vivo test systems for the evaluation of the effects of potentiators of mGluR5 related activity in laboratory animals such as cats, dogs, rabbits, monkeys, rats and mice, as part of the search for new therapeutic agents of mGluR5.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard. Coupling constants (J-values) are expressed in Hz units.

Microwave assisted reactions were performed in a single-mode reactor: Emrys™ Optimizer microwave reactor (Personal Chemistry A.B., currently Biotage).

Hydrogenation reactions were performed in a continuous flow hydrogenator: H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from: (a) ISCO, on irregular silica gel, particle size 15-40 μm (normal layer disposable flash columns) on a Companion system from ISCO, Inc.; or, (b) Merck, on irregular silica gel, particle size 15-40 μm (normal layer disposable flash columns) on an SPOT or LAFLASH system from Armen Instrument.

Melting point values are peak values, and are obtained with experimental uncertainties that are commonly associated with this analytical method. For a number of compounds, melting points were determined in open capillary tubes either on a Mettler FP62 or on a Mettler FP81HT-FP90 apparatus. Melting points were measured with a temperature gradient of 10° C./minute. Maximum temperature was 300° C. The melting point was read from a digital display.

Analytical HPLC was performed on an HP1100 with UV detection at 214 and 254 nm along with ELSD detection and low resolution mass spectra using an Agilent 1200 series 6130 mass spectrometer.

Preparative RP-HPLC purification was performed on a custom HP1100 automated purification system with collection triggered by mass detection or using a Gilson Inc. preparative UV-based system using a Phenomenex Luna C18 column (50×30 mm I.D., 5 μm) with an acetonitrile (unmodified)-water (0.1% TFA) custom gradient.

2. LC-MS Methods a. General Procedure A

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software. [M+H], means the protonated mass of the free base of the compound and where indicated $R_t$ means retention time (in minutes).

b. General Procedure B

The HPLC measurement was performed using an HP 1100 (Agilent Technologies) system comprising a pump (quaternary or binary) with degasser, an autosampler, a column oven, a diode-array detector (DAD) and a column as specified in the respective methods below. Flow from the column was split to the MS spectrometer. The MS detector was configured with an electrospray ionization source. Nitrogen was used as the nebulizer gas. The source temperature was maintained at 140° C. Data acquisition was performed with MassLynx-Openlynx software.

c. LCMS Method 1

In addition to the general procedure A: Reversed phase UPLC was carried out on a BEH-C18 column (1.7 μm, 2.1× 50 mm) from Waters, with a flow rate of 1.0 mL/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume was 2.0 μl. Low-resolution mass spectra (single quadrupole, SQD detector) were acquired by scanning from 100 to 1000 in 0.1 seconds using an inter-channel delay of 0.08 seconds. The capillary needle voltage was 3 kV. The cone voltage was 25 V for positive ionization mode and 30 V for negative ionization mode.

d. LCMS Method 2

Same gradient as LCMS Method 1; column used: RRHD Eclipse Plus-C18 (1.8 μm 2.1×50 mm) from Agilent.

e. LCMS Method 3

In addition to the general procedure A: Reversed phase UPLC was carried out on a RRHD Eclipse Plus-C18 (1.8 μm 2.1×50 mm) from Agilent, with a flow rate of 1.0 ml/min, at 50° C. without split to the MS detector. The gradient conditions used are: 95% A (0.5 g/l ammonium acetate solution+ 5% acetonitrile), 5% B (acetonitrile), to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 seconds. The capillary needle voltage was 3 kV. The cone voltage was 25 V for positive ionization mode and 30 V for negative ionization mode.

f. LCMS Method 4

In addition to the general procedure B: Reversed phase HPLC was carried out on a Eclipse Plus-C18 column (3.5 μm 2.1×30 mm) from Agilent, with a flow rate of 1.0 ml/min, at 60° C. The gradient conditions used are: 95% A (0.5 g/l ammonium acetate solution+5% acetonitrile), 5% B (mixture of acetonitrile/methanol, 1/1) to 100% B in 5.0 minutes, kept till 5.15 minutes and equilibrated to initial conditions at 5.3 minutes until 7.0 minutes. Injection volume 2 High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

g. LCMS Method 5

In addition to the general procedure B: Reversed phase HPLC was carried out on an Eclipse Plus-C18 column (3.5 μm 2.1×30 mm) from Agilent, with a flow rate of 1.0 ml/min, at 60° C. without split to the MS detector. The gradient conditions used are: 95% A (0.5 g/l ammonium acetate solution+ 5% acetonitrile), 5% B (mixture of acetonitrile/methanol, 1/1), to 100% B in 5.0 minutes, kept till 5.15 minutes and equilibrated to initial conditions at 5.30 minutes until 7.0

3. Preparation of 7-chloro-2-chloromethyl-5-methyl-sulfanyl-imidazo[1,2-c]pyrimidine

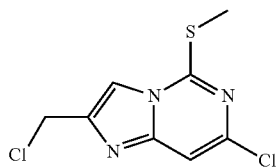

1,3-Dichloroacetone (2.89 g, 22.77 mmol) was added to a solution 6-chloro-2-methylsulfanyl-pyrimidin-4-ylamine (4 g, 22.77 mmol) in AcOH (15 mL) and the mixture was stirred at 110° C. for 16 hours. Then H$_2$O was added and the solid formed was filtered off and dried in vacuo to yield 7-chloro-2-chloromethyl-5-methylsulfanyl-imidazo[1,2-c]pyrimidine (2.5 g, 44% yield) as a pale brown solid that was used in the next step without further purification.

4. Preparation of 7-chloro-5-methylsulfanyl-2-phenoxymethyl-imidazo[1,2-c]pyrimidine

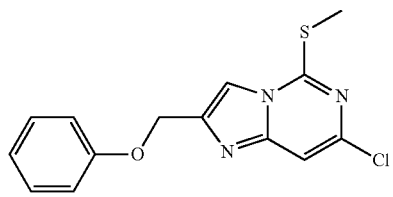 [SMILES: CSc1nc(Cl)cc2nc(COc3ccccc3)cn12]

Phenol (0.050 g, 0.53 mmol) was added to a suspension of 7-chloro-2-chloromethyl-5-methylsulfanyl-imidazo[1,2-c]pyrimidine (0.15 g, 0.53 mmol) and K$_2$CO$_3$ (0.21 g, 1.58 mmol) in ACN (2 mL). The mixture was stirred at 50° C. for 18 hours and then the solvents were evaporated in vacuo. The crude product was purified by flash column chromatography (silica; DCM). The desired fractions were collected and the solvents evaporated in vacuo. The product was triturated with diethyl ether and the solid thus obtained, filtered and dried in vacuo to yield 7-chloro-5-methylsulfanyl-2-phenoxymethyl-imidazo[1,2-c]pyrimidine (0.085 g, 53% yield) as a white solid.

5. Preparation of 7-chloro-2-phenoxymethyl-6H-imidazo[1,2-c]pyrimidin-5-one

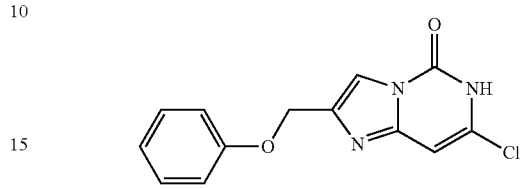

A solution of lithium hydroxide (66 mg, 2.75 mmol) in H$_2$O (10 mL) was added to a solution of 7-chloro-5-methylsulfanyl-2-phenoxymethyl-imidazo[1,2-c]pyrimidine (0.70 g, 2.29 mmol) in THF (10 mL). The mixture was stirred at 50° C. for 4 hours and then diluted with DCM. The organic layer was separated, dried (Na$_2$SO$_4$), filtered and the solvents evaporated in vacuo to yield 7-chloro-2-phenoxymethyl-6H-imidazo[1,2-c]pyrimidin-5-one (0.62 g, 98% yield) as a white solid that was used in the next step without further purification.

6. Preparation of 2-phenoxymethyl-6H-imidazo[1,2-c]pyrimidin-5-one

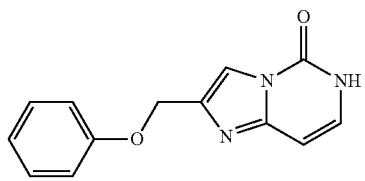 [SMILES: O=c1[nH]ccc2nc(COc3ccccc3)cn12]

10% Palladium hydroxide (0.43 g, 3 mmol) was added to a solution of 7-chloro-2-phenoxymethyl-6H-imidazo[1,2-c]pyrimidin-5-one (0.24 g, 0.85 mmol) and TEA (0.6 mL, 4.32 mmol) in a mixture of AcOEt and MeOH (60 mL). The mixture was hydrogenated in a Parr reactor (45 psi) at 50° C. for 16 hours. Then 10% palladium hydroxide (0.18 g, 0.43 mmol) was added and the mixture hydrogenated again in a Parr reactor (45 psi) at 50° C. for 16 hours. The mixture was hydrogenated over 5 cycles with addition of 10% palladium hydroxide (0.18 g, 0.43 mmol) every cycle. The mixture was filtered through a pad of diatomaceous earth and washed with MeOH. The solvents were evaporated in vacuo and the crude product purified by flash column chromatography (silica; 7 M solution of ammonia in MeOH in DCM with a gradient of 0/100 to 40/60). The desired fractions were collected and the

--- minutes. Injection volume 2 µl. Low-resolution mass spectra (single quadrupole, SQD detector) were acquired by scanning from 100 to 1000 in 0.1 second using an inter-channel delay of 0.08 seconds. The capillary needle voltage was 3 kV. The cone voltage was 20 V for positive ionization mode and 30 V for negative ionization mode.

solvents evaporated in vacuo to yield 2-phenoxymethyl-6H-imidazo[1,2-c]pyrimidin-5-one (0.19 g, 92% yield) as a white solid.

7. Preparation of 4-amino-1-(4-fluoro-phenyl)-1H-pyrimidin-2-one

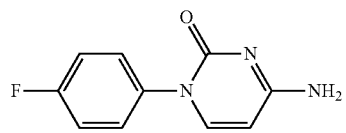 [SMILES: Nc1ccn(-c2ccc(F)cc2)c(=O)n1]

TMEDA (8 mL, 54 mmol) was added to a stirred suspension of cytosine (3 g, 27 mmol), 4-fluorophenylboronic acid (7.55 g, 5 mmol) and copper(II)acetate monohydrate (5.44 g, 27 mmol) in a mixture of MeOH (960 mL) and H$_2$O (240 mL). The mixture was stirred at RT for 16 hours. The solvents were evaporated in vacuo and the crude product purified by open column chromatography (silica; MeOH in DCM with a gradient of 0/100 to 100/0). The desired fractions were collected and the solvents evaporated in vacuo. The product was triturated with MeOH and DCM and the solid formed filtered and dried in vacuo to yield 4-amino-1-(4-fluoro-phenyl)-1H-pyrimidin-2-one (3.3 g, 60% yield) as a white solid.

8. Preparation of 4-amino-1-(4-fluoro-phenyl)-5-iodo-1H-pyrimidin-2-one

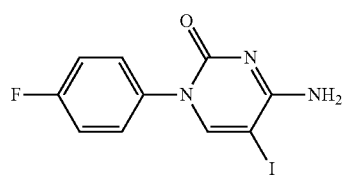 [SMILES: Nc1nc(=O)n(-c2ccc(F)cc2)cc1I]

Sodium metaperiodate (0.21 g, 0.97 mmol) and iodine (0.495 g, 1.95 mmol) were added to a stirred solution of 4-amino-1-(4-fluoro-phenyl)-1H-pyrimidin-2-one (1 g, 4.87 mmol) in a mixture of acetic acid (12 mL), water (3 mL) and H$_2$SO$_4$ (0.4 mL). The mixture was stirred at 80° C. for 4 hours. The mixture was poured onto an ice-cold 10% aqueous solution of Na$_2$SO$_3$ and then neutralized with a 2N aqueous solution of NaOH to pH 7. A solid was formed, filtered and washed with water and EtOH to yield 4-amino-1-(4-fluoro-phenyl)-5-iodo-1H-pyrimidin-2-one (1.35 g, 84% yield) as a white solid, that was used in the next step without further purification.

9. Preparation of 2-chloromethyl-6-(4-fluoro-phenyl)-6H-imidazo[1,2-c]pyrimidin-5-one

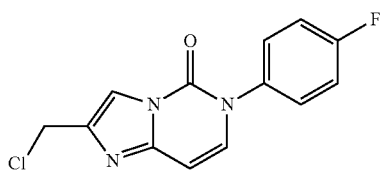 [SMILES: O=c1n(-c2ccc(F)cc2)ccc2nc(CCl)cn12]

1,3-Dichloroacetone (2.27 g, 11.92 mmol) was added to a solution of 4-amino-1-(4-fluoro-phenyl)-1H-pyrimidin-2-one (4.6 g, 12 mmol) in DMF (135 mL). The mixture was stirred at 150° C. for 30 minutes under microwave irradiation and then the solvent was evaporated in vacuo. The crude product was purified by flash column chromatography (silica; AcOEt in DCM with a gradient of 0/100 to 30/70). The desired fractions were collected and the solvents evaporated in vacuo to yield 2-chloromethyl-6-(4-fluoro-phenyl)-6H-imidazo[1,2-c]pyrimidin-5-one (2.5 g, 75% yield) as a solid.

10. Preparation of 2-chloromethyl-6-(3-fluoro-phenyl)-6H-imidazo[1,2-c]pyrimidin-5-one

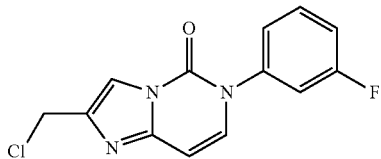 [SMILES: O=c1n(-c2cccc(F)c2)ccc2nc(CCl)cn12]

2-chloromethyl-6-(3-fluoro-phenyl)-6H-imidazo[1,2-c]pyrimidin-5-one was prepared from cytosine and 3-fluorophenylboronic acid using the methods as described above for the preparation of 4-amino-1-(4-fluoro-phenyl)-1H-pyrimidin-2-one and 2-chloromethyl-6-(4-fluoro-phenyl)-6H-imidazo[1,2-c]pyrimidin-5-one.

11. Preparation of 2-chloromethyl-6-(3,4-difluoro-phenyl)-6H-imidazo[1,2-c]pyrimidin-5-one

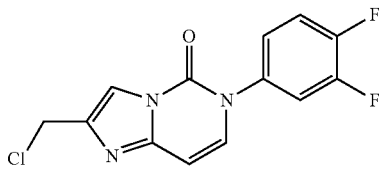 [SMILES: O=c1n(-c2ccc(F)c(F)c2)ccc2nc(CCl)cn12]

2-chloromethyl-6-(3,4-difluoro-phenyl)-6H-imidazo[1,2-c]pyrimidin-5-one was prepared from cytosine and 3,4-difluorophenylboronic acid using the methods as described above for the preparation of 4-amino-1-(4-fluoro-phenyl)-1H-pyrimidin-2-one and 2-chloromethyl-6-(4-fluoro-phenyl)-6H-imidazo[1,2-c]pyrimidin-5-one.

12. Preparation of 2-chloromethyl-6-(3-Trifluoromethyl-phenyl)-6H-imidazo[1,2-c]pyrimidin-5-one

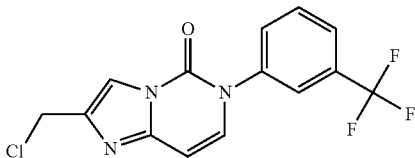 [SMILES: O=c1n(-c2cccc(C(F)(F)F)c2)ccc2nc(CCl)cn12]

2-chloromethyl-6-(3-trifluoromethyl-phenyl)-6H-imidazo[1,2-c]pyrimidin-5-one was prepared from cytosine and 3-(trifluoromethyl)phenylboronic acid using the methods as described above for the preparation of 4-amino-1-(4-fluorophenyl)-1H-pyrimidin-2-one and 2-chloromethyl-6-(4-fluoro-phenyl)-6H-imidazo[1,2-c]pyrimidin-5-one.

13. Preparation of 2-chloromethyl-6-(4-fluoro-phenyl)-7-methyl-6H-imidazo[1,2-c]pyrimidin-5-one

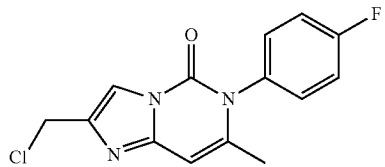 [SMILES: Cc1cc2nc(CCl)cn2c(=O)n1-c1ccc(F)cc1]

2-Chloromethyl-6-(4-fluoro-phenyl)-7-methyl-6H-imidazo[1,2-c]pyrimidin-5-one was prepared from 4-amino-6-methyl-1H-pyrimidin-2-one and 4-fluorophenylboronic acid using the methods as described above for the preparation of 4-amino-1-(4-fluoro-phenyl)-1H-pyrimidin-2-one and 2-chloromethyl-6-(4-fluoro-phenyl)-6H-imidazo[1,2-c]pyrimidin-5-one.

14. Preparation of 4-amino-1-benzyl-1H-pyrimidin-2-one

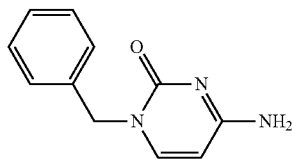 [SMILES: Nc1ccn(Cc2ccccc2)c(=O)n1]

A 0.1 M solution of tetra-N-butylammonium hydroxide in a mixture of MeOH and 2-propanol (90 mL, 9.0 mmol) was added dropwise to a stirred suspension of cytosine (1 g, 9.0 mmol) in DMF (70 mL). The solution became clear and benzyl bromide (2.14 mL, 18 mmol) was added dropwise. The reaction mixture was stirred at RT for 2 hours and then the solvents were evaporated in vacuo. The crude product was purified by flash column chromatography (silica; MeOH in DCM with a gradient of 0/100 to 50/50). The desired fractions were collected and the solvents evaporated in vacuo to yield 4-amino-1-benzyl-1H-pyrimidin-2-one (1 g, 57% yield) as a white solid.

15. Preparation of 4-amino-1-methyl-1H-pyrimidin-2-one

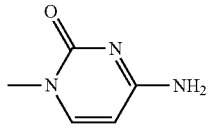

4-Amino-1-methyl-1H-pyrimidin-2-one was prepared from cytosine and methyliodide using the methods described above for the preparation of 4-amino-1-benzyl-1H-pyrimidin-2-one.

16. Preparation of 4-amino-1-cyclopropylmethyl-1H-pyrimidin-2-one

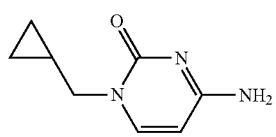 [SMILES: Nc1ccn(CC2CC2)c(=O)n1]

4-Amino-1-cyclopropylmethyl-1H-pyrimidin-2-one was prepared from cytosine and (bromomethyl)cyclopropane using the methods described above for the preparation of 4-amino-1-benzyl-1H-pyrimidin-2-one.

17. Preparation of 6-benzyl-2-chloromethyl-6H-imidazo[1,2-c]pyrimidin-5-one

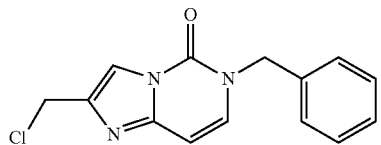 [SMILES: O=c1n(Cc2ccccc2)ccc2nc(CCl)cn12]

6-Benzyl-2-chloromethyl-6H-imidazo[1,2-c]pyrimidin-5-one was prepared from 4-amino-1-benzyl-1H-pyrimidin-2-one and 1,3-dichloroacetone using the methods described above for the preparation of 2-chloromethyl-6-(4-fluoro-phenyl)-6H-imidazo[1,2-c]pyrimidin-5-one.

18. Preparation of 2-chloromethyl-6-methyl-6H-imidazo[1,2-c]pyrimidin-5-one

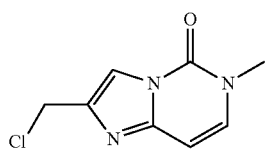

2-Chloromethyl-6-methyl-6H-imidazo[1,2-c]pyrimidin-5-one was prepared from 4-amino-1-methyl-1H-pyrimidin-2-one and 1,3-dichloroacetone using the methods described above for the preparation of 2-chloromethyl-6-(4-fluoro-phenyl)-6H-imidazo[1,2-c]pyrimidin-5-one.

19. Preparation of 2-chloromethyl-6-cyclopropylmethyl-6H-imidazo[1,2-c]pyrimidin-5-one

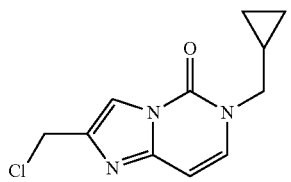 [SMILES: O=c1n(CC2CC2)ccc2nc(CCl)cn12]

2-Chloromethyl-6-cyclopropylmethyl-6H-imidazo[1,2-c]pyrimidin-5-one was prepared from 4-amino-1-cyclopropylmethyl-1H-pyrimidin-2-one and 1,3-dichloroacetone using the methods described above for the preparation of 2-chloromethyl-6-(4-fluoro-phenyl)-6H-imidazo[1,2-c]pyrimidin-5-one.

20. Preparation of 2-Chloromethyl-8-fluoro-6-(4-fluoro-phenyl)-6H-imidazo[1,2-C]pyrimidin-5-one

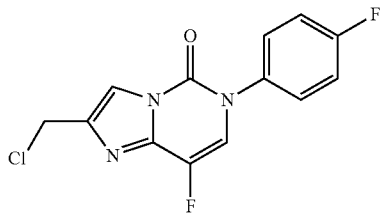 [SMILES: O=c1n(-c2ccc(F)cc2)cc(I)c2nc(CCl)cn12]

2-Chloromethyl-8-fluoro-6-(4-fluoro-phenyl)-6H-imidazo[1,2-c]pyrimidin-5-one was prepared from 5-fluorocytosine and 4-fluorophenylboronic acid using the methods as described above for the preparation of 4-amino-1-(4-fluoro-phenyl)-1H-pyrimidin-2-one and 2-chloromethyl-6-(4-fluoro-phenyl)-6H-imidazo[1,2-c]pyrimidin-5-one.

21. Preparation of 2-Chloromethyl-6-(4-fluoro-phenyl)-8-iodo-6H-imidazo[1,2-c]pyrimidin-5-one

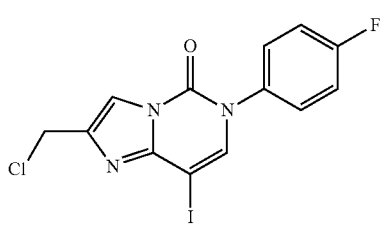

2-Chloromethyl-6-(4-fluoro-phenyl)-8-iodo-6H-imidazo[1,2-c]pyrimidin-5-one was prepared from 4-amino-1-(4-fluoro-phenyl)-5-iodo-1H-pyrimidin-2-one and 1,3-dichloroacetone using the methods as described above for the preparation of 2-chloromethyl-6-(4-fluoro-phenyl)-6H-imidazo[1,2-c]pyrimidin-5-one.

22. Preparation of 3-Bromo-2-chloromethyl-6-(4-fluoro-phenyl)-6H-imidazo[1,2-c]pyrimidin-5-one

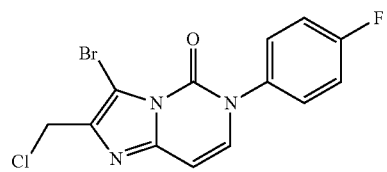 [SMILES: O=c1n(-c2ccc(F)cc2)ccc2nc(CCl)c(Br)n12]

N-bromosuccinimide (80.4 mg, 0.45 mmol) was added to a stirred solution of 2-chloromethyl-6-(4-fluoro-phenyl)-6H-imidazo[1,2-c]pyrimidin-5-one (0.114 g, 0.41 mmol) and benzoyl peroxide (9.94 mg, 0.041 mmol) in DCE (3 mL). The mixture was stirred at RT for 16 hours. The solvent was evaporated in vacuo and the crude product was purified by flash column chromatography (silica; AcOEt in DCM with a gradient of 0/100 to 20/80). The desired fractions were collected and the solvents evaporated in vacuo to yield 3-bromo-2-chloromethyl-6-(4-fluoro-phenyl)-6H-imidazo[1,2-c]pyrimidin-5-one (0.102 g, 70% yield) as a white solid.

23. Preparation of 6-(4-fluoro-phenyl)-2-phenoxymethyl-6H-imidazo[1,2-c]pyrimidin-5-one

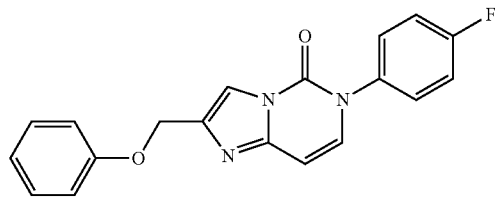 [SMILES: O=c1n(-c2ccc(F)cc2)ccc2nc(COc3ccccc3)cn12]

Phenol (40 mg, 0.24 mmol) was added to a stirred suspension of 2-chloromethyl-6-(4-fluoro-phenyl)-6H-imidazo[1,2-c]pyrimidin-5-one (0.107 g, 0.38 mmol) and $K_2CO_3$ (0.160 g, 1.15 mmol) in ACN (3 mL). The mixture was stirred at 90° C. for 16 hours and then the solvents were evaporated in vacuo. The crude product was purified by flash column chromatography (silica; AcOEt in DCM with a gradient of 0/100 to 20/80). The desired fractions were collected and the solvents evaporated in vacuo. The product was triturated with diethyl ether to yield 6-(4-fluoro-phenyl)-2-phenoxymethyl-6H-imidazo[1,2-c]pyrimidin-5-one (0.12 g, 90% yield) as a white solid. $^1$H NMR (500 MHz, $CDCl_3$) δ ppm 5.20 (s, 2H), 6.70 (d, J=7.8 Hz, 1H), 6.98 (t, J=7.2 Hz, 1H), 7.03 (d, J=8.1

Hz, 2H), 7.12 (d, J=7.8 Hz, 1H), 7.19-7.25 (m, 2H), 7.27-7.34 (m, 2H), 7.38-7.45 (m, 2H), 7.83 (s, 1H).

24. Preparation of 6-(4-fluoro-phenyl)-2-phenoxymethyl-6H-imidazo[1,2-c]pyrimidin-5-one

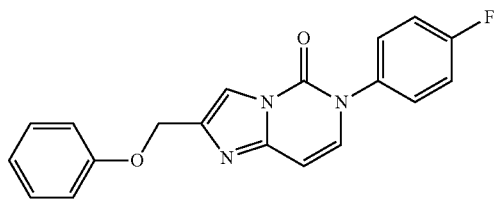 [SMILES: O=c1n(-c2ccc(F)cc2)ccc2nc(COc3ccccc3)cn12]

Copper(I)iodide (11.8 mg, 0.062 mmol) was added to a stirred suspension of 2-phenoxymethyl-6H-imidazo[1,2-c]pyrimidin-5-one (50 mg, 0.21 mmol), 4-fluoroiodobenzene (72.5 mg, 0.41 mmol), $K_2CO_3$ (57 mg, 0.41 mmol) and N,N'-dimethylethylenediamine (0.011 mL, 0.1 mmol) in toluene (1 mL) in a sealed tube. The mixture was stirred at 120° C. for 16 hours. The mixture was filtered through a pad of diatomaceous earth and then the solvent was evaporated in vacuo. The crude product was purified by flash column chromatography (silica; AcOEt in DCM with a gradient of 0/100 to 30/70). The desired fractions were collected and evaporated in vacuo to yield 6-(4-fluoro-phenyl)-2-phenoxymethyl-6H-imidazo[1,2-c]pyrimidin-5-one (45 mg, 65% yield) as a white solid. $^1$H NMR (500 MHz, $CDCl_3$) δ ppm 5.20 (s, 2H), 6.70 (d, J=7.8 Hz, 1H), 6.98 (t, J=7.2 Hz, 1H), 7.03 (d, J=8.1 Hz, 2H), 7.12 (d, J=7.8 Hz, 1H), 7.19-7.25 (m, 2H), 7.27-7.34 (m, 2H), 7.38-7.45 (m, 2H), 7.83 (s, 1H).

25. Preparation of 6-(2-Methoxy-pyrimidin-4-yl)-2-phenoxymethyl-6H-imidazo[1,2-c]pyrimidin-5-one

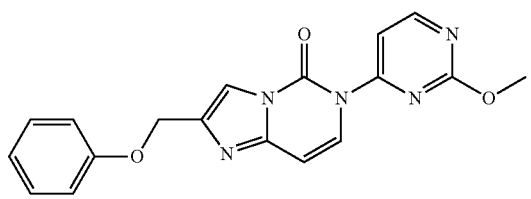 [SMILES: COc1nccc(-n2ccc3nc(COc4ccccc4)cn3c2=O)n1]

Palladium(II)acetate (4.2 mg, 0.019 mmol) was added to a stirred suspension of 2-phenoxymethyl-6H-imidazo[1,2-c]pyrimidin-5-one (150 mg, 0.62 mmol), 4-chloro-2-methoxypyrimidine (107.9 mg, 0.75 mmol), $Cs_2CO_3$ (283.6 mg, 0.87 mmol) and 2-dicyclohexylphosphino-2',4',6'-triiso-propyl-1,1'-biphenyl (26.7 mg, 0.056 mmol) in 1,4-dioxane (2 mL) under nitrogen and in a sealed tube. The mixture was stirred at 100° C. for 3 days and at 140° C. for 15 minutes under microwave irradiation. The solvent was evaporated in vacuo and the crude product was purified by flash column chromatography (silica; AcOEt in DCM with a gradient of 0/100 to 100/0). The desired fractions were collected and the solvents evaporated in vacuo. The product was triturated with diethyl ether to yield 6-(2-methoxy-pyrimidin-4-yl)-2-phenoxymethyl-6H-imidazo[1,2-c]pyrimidin-5-one (43 mg, 20% yield) as a white solid. $^1$H NMR (400 MHz, $CDCl_3$) δ ppm 4.09 (s, 3H), 5.18 (d, J=0.9 Hz, 2H), 6.77 (dd, J=8.2, 0.6 Hz, 1H), 6.95-7.06 (m, 3H), 7.27-7.36 (m, 2H), 7.85 (d, J=0.7 Hz, 1H), 7.91 (d, J=5.5 Hz, 1H), 8.24 (d, J=8.1 Hz, 1H), 8.65 (d, J=5.5 Hz, 1H).

26. Preparation of 6-(4-Fluoro-phenyl)-8-methyl-2-phenoxymethyl-6H-imidazo[1,2-c]pyrimidin-5-one

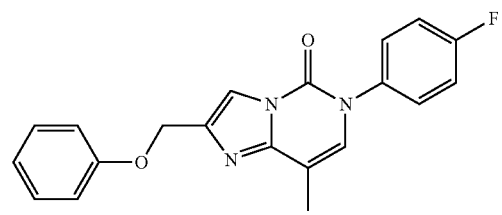 [SMILES: Cc1cn(-c2ccc(F)cc2)c(=O)n2cc(COc3ccccc3)nc12]

Tetrakis(triphenylphosphine)palladium(0) (2.63 mg, 0.0023 mmol) was added to a stirred suspension of 6-(4-fluoro-phenyl)-8-iodo-2-phenoxymethyl-6H-imidazo[1,2-c]pyrimidin-5-one (35 mg, 0.076 mmol), methylboronic acid (22.7 mg, 0.38 mmol) and $K_2CO_3$ (31.5 mg, 0.23 mmol) in a mixture of 1,4-dioxane (4 mL) and DMF (1 mL) under nitrogen and in a sealed tube. The mixture was stirred at 150° C. for 45 minutes under microwave irradiation. The solvents were evaporated in vacuo and the crude product was purified by flash column chromatography (silica; AcOEt in DCM with a gradient of 0/100 to 20/80). The desired fractions were collected and the solvents evaporated in vacuo to yield 6-(4-fluoro-phenyl)-8-methyl-2-phenoxymethyl-6H-imidazo[1,2-c]pyrimidin-5-one (19 mg, 72% yield) as a white solid. $^1$H NMR (500 MHz, $CDCl_3$) δ ppm 2.36 (d, J=1.2 Hz, 3H), 5.22 (s, 2H), 6.92 (d, J=1.2 Hz, 1H), 6.97 (br. t, J=7.4, 7.4 Hz, 1H), 7.02 (br. d, J=8.1 Hz, 2H), 7.16-7.24 (m, 2H), 7.27-7.34 (m, 2H), 7.36-7.44 (m, 2H), 7.84 (s, 1H).

27. Preparation of 3-Chloro-6-(4-fluoro-phenyl)-2-phenoxymethyl-6H-imidazo[1,2-c]pyrimidin-5-one

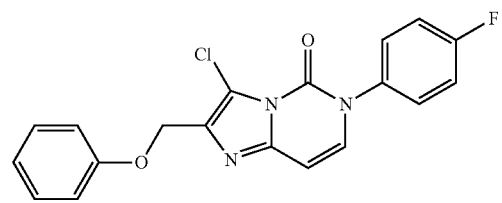 [SMILES: O=c1n(-c2ccc(F)cc2)ccc2nc(COc3ccccc3)c(Cl)n12]

N-chlorosuccinimide (32.9 mg, 0.25 mmol) was added to a stirred solution of 6-(4-fluoro-phenyl)-2-phenoxymethyl-6H-imidazo[1,2-c]pyrimidin-5-one (75 mg, 0.22 mmol) in DMF (3.5 mL). The mixture was stirred at 150° C. for 15 minutes under microwave irradiation. The solvent was evaporated in vacuo and the crude product was purified by flash column chromatography (silica; AcOEt in DCM with a gradient of 0/100 to 20/80). The desired fractions were collected and the solvents evaporated in vacuo. The product was triturated with DIPE to yield 3-chloro-6-(4-fluoro-phenyl)-2-phenoxymethyl-6H-imidazo[1,2-c]pyrimidin-5-one (46 mg, 56% yield) as a white solid. $^1$H NMR (400 MHz, $CDCl_3$) δ ppm 5.12 (s, 2H), 6.62 (d, J=7.9 Hz, 1H), 6.98 (tt, J=7.4, 0.9

Hz, 1H), 7.03-7.07 (m, 2H), 7.06 (d, J=7.6 Hz, 1H), 7.17-7.25 (m, 2H), 7.27-7.34 (m, 2H), 7.35-7.43 (m, 2H).

28. Preparation of 6-(4-fluoro-phenyl)-2-phenoxymethyl-7,8-dihydro-6H-imidazo[1,2-c]pyrimidin-5-one

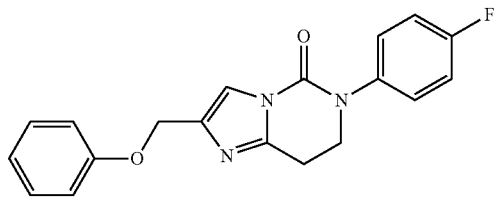 [SMILES: O=C1N(c2ccc(F)cc2)CCc2nc(COc3ccccc3)cn21]

10% Palladium hydroxide (10 mg, 0.07 mmol) was added to a stirred solution of 6-(4-fluoro-phenyl)-2-phenoxymethyl-6H-imidazo[1,2-c]pyrimidin-5-one (47 mg, 0.14 mmol) in MeOH (50 mL). The mixture was hydrogenated in a Parr reactor at room temperature under $H_2$ atmosphere for 6 hours. Then the mixture was hydrogenated other 7 cycles in a Parr reactor (50 psi) at 50° C. for 16 hours with addition of 10% palladium hydroxide (10 mg, 0.07 mmol) every cycle. The mixture was filtered through a pad of diatomaceous earth and the solvents were evaporated in vacuo. The crude product was purified by flash column chromatography (silica; AcOEt in DCM with a gradient of 0/100 to 50/50). The desired fractions were collected and the solvents evaporated in vacuo to yield 6-(4-fluoro-phenyl)-2-phenoxymethyl-7,8-dihydro-6H-imidazo[1,2-c]pyrimidin-5-one (27 mg, 57% yield) as a white solid. $^1$H NMR (400 MHz, CDCl$_3$) δ ppm 3.29 (t, J=6.7 Hz, 2H), 4.00 (t, J=6.7 Hz, 2H), 5.02 (d, J=0.7 Hz, 2H), 6.94-6.99 (m, 1H), 6.99-7.05 (m, 2H), 7.10-7.17 (m, 2H), 7.27-7.35 (m, 4H), 7.57 (s, 1H).

29. Preparation of 2-(3-fluoro-phenoxymethyl)-6-(4-fluoro-phenyl)-7,8-dihydro-6H-imidazo[1,2-c]pyrimidin-5-one

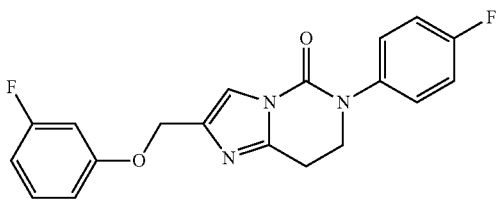 [SMILES: O=C1N(c2ccc(F)cc2)CCc2nc(COc3cccc(F)c3)cn21]

Drops of water were added to a stirred suspension of 2 M aqueous solution of HCl (0.78 mL, 1.57 mmol) and 6-(4-fluoro-phenyl)-2-phenoxymethyl-6H-imidazo[1,2-c]pyrimidin-5-one (554 mg, 1.57 mmol) in MeOH (110 mL) until a clear solution was obtained. The mixture was hydrogenated in a H-cube reactor (1 mL/min, 30 mm 20% palladium hydroxide on carbon cartridge, 60° C., full hydrogen mode) then (2 mL/min, 30 mm 20% palladium hydroxide on carbon cartridge, 80° C., full hydrogen mode) then (3 mL/min, 30 mm 20% palladium hydroxide on carbon cartridge, 80° C., full hydrogen mode) and then (3 mL/min, 30 mm 20% palladium hydroxide on carbon cartridge, 80° C., full hydrogen mode). The solvents were evaporated in vacuo. The residue was made basic with a saturated solution of NaHCO$_3$ and extracted with DCM. The organic layer was separated, dried (Na$_2$SO$_4$), filtered and the solvents evaporated in vacuo. The crude product was purified by flash column chromatography (silica; AcOEt in DCM with a gradient of 0/100 to 50/50). The desired fractions were collected and the solvents evaporated in vacuo to yield a white solid and an impure fraction which was purified by flash column chromatography (silica; AcOEt in DCM with a gradient of 0/100 to 20/80) to yield as a white solid. The two solids were combined to yield 2-(3-fluoro-phenoxymethyl)-6-(4-fluoro-phenyl)-7,8-dihydro-6H-imidazo[1,2-c]pyrimidin-5-one (327 mg, 58% yield) as a white solid. $^1$H NMR (500 MHz, CDCl$_3$) δ ppm 3.29 (t, J=6.6 Hz, 2H), 4.01 (t, J=6.8 Hz, 2H), 5.00 (s, 2H), 6.68 (td, J=8.3, 2.2 Hz, 1H), 6.73 (dt, J=11.0, 2.3 Hz, 1H), 6.79 (dd, J=8.2, 2.2 Hz, 1H), 7.10-7.18 (m, 2H), 7.20-7.26 (m, 1H), 7.29-7.35 (m, 2H), 7.57 (s, 1H).

30. Preparation of 2-(4-Fluoro-phenoxymethyl)-6-(4-fluoro-phenyl)-7,8-dihydro-6H-imidazo[1,2-c]pyrimidin-5-one

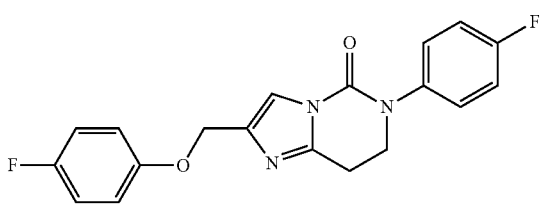 [SMILES: O=C1N(c2ccc(F)cc2)CCc2nc(COc3ccc(F)cc3)cn21]

A solution of 2-(4-fluoro-phenoxymethyl)-6-(4-fluoro-phenyl)-6H-imidazo[1,2-c]pyrimidin-5-one (0.1 g, 0.28 mmol) in EtOH (25 mL) was hydrogenated in a H-cube reactor (1 mL/min, 30 mm Raney nickel cartridge, 35° C., full hydrogen mode, 3 cycles) and then (1 mL/min, 30 mm Raney nickel cartridge, 40° C., full hydrogen mode, 3 cycles). The solvent was evaporated in vacuo and the crude product was purified by flash column chromatography (silica; AcOEt in DCM with a gradient of 50/50 to 75/25). The desired fractions were collected and the solvents evaporated in vacuo to yield 2-(4-fluoro-phenoxymethyl)-6-(4-fluoro-phenyl)-7,8-dihydro-6H-imidazo[1,2-c]pyrimidin-5-one (45 mg, 45% yield). $^1$H NMR (500 MHz, CDCl$_3$) δ ppm 3.29 (t, J=6.6 Hz, 2H), 4.00 (t, J=6.6 Hz, 2H), 4.98 (s, 2H), 6.92-7.01 (m, 4H), 7.10-7.18 (m, 2H), 7.29-7.36 (m, 2H), 7.56 (s, 1H).

31. Preparation of 6-(5-Methyl-pyridin-2-yl)-2-phenoxymethyl-7,8-dihydro-6H-imidazo[1,2-c]pyrimidin-5-one

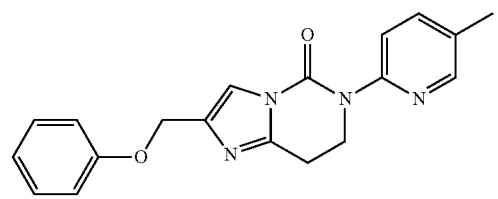 [SMILES: Cc1ccc(N2CCc3nc(COc4ccccc4)cn3C2=O)nc1]

A 1.25 M solution of HCl in MeOH (3 mL) was added to a stirred solution of 6-(5-methyl-pyridin-2-yl)-2-phenoxymethyl-6H-imidazo[1,2-c]pyrimidin-5-one (0.1 g, 0.3 mmol) in MeOH (10 mL) was hydrogenated in a H-cube reactor (1 mL/min, 30 mm Raney nickel cartridge, 30° C., full hydrogen mode, 4 cycles) and then (1 mL/min, 30 mm Raney nickel cartridge, RT, full hydrogen mode, 1 cycle). The solvents were evaporated in vacuo and the crude product was purified by flash column chromatography (silica; AcOEt in DCM with a gradient of 0/100 to 100/0 and then 7 M solution of ammonia in MeOH in DCM with a gradient of 0/100 to 2/98). The desired fractions were collected and the solvents evaporated in vacuo. The product was repurified by RP HPLC (C18 XBridge 19×100 5 um, gradient from 80% of 0.1% solution of ammonium formate/ammonium hydroxide buffer pH 9 solution in water and 20% CH₃CN to 0% of 0.1% solution of ammonium formate/ammonium hydroxide buffer pH 9 solution in water and 100% ACN) to yield 6-(5-methyl-pyridin-2-yl)-2-phenoxymethyl-7,8-dihydro-6H-imidazo[1,2-c]pyrimidin-5-one (5 mg, 5% yield). $^1$H NMR (500 MHz, CDCl$_3$) δ ppm 2.35 (s, 3H), 3.24 (t, J=6.6 Hz, 2H), 4.35 (t, J=6.6 Hz, 2H), 5.03 (s, 2H), 6.97 (br. t, J=7.4, 7.4 Hz, 1H), 6.99-7.05 (m, 2H), 7.27-7.33 (m, 2H), 7.57 (dd, J=8.5, 2.2 Hz, 1H), 7.59 (s, 1H), 7.71 (d, J=8.4 Hz, 1H), 8.25 (dd, J=1.6, 0.7 Hz, 1H).

32. Preparation of 6-(4-Fluoro-phenyl)-2-m-Tolyloxymethyl-7,8-dihydro-6H-imidazo[1,2-c]pyrimidin-5-one

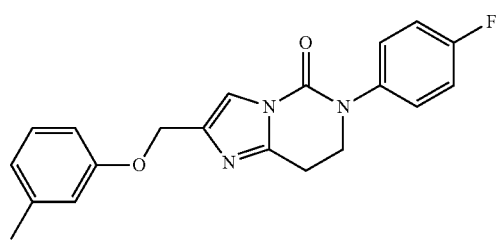 [SMILES: Cc1cccc(OCc2cn3c(n2)CCN(c2ccc(F)cc2)C3=O)c1]

Activated Raney nickel (a portion of spatula) was added to a suspension of 6-(4-fluoro-phenyl)-2-m-tolyloxymethyl-6H-imidazo[1,2-c]pyrimidin-5-one (70 mg, 0.2 mmol) in MeOH (20 mL). The mixture was hydrogenated at RT under H$_2$ atmosphere for 3 days. The mixture was filtered through a pad of diatomaceous earth and the solvents were evaporated in vacuo. The crude product was purified by flash column chromatography (silica; AcOEt in DCM with a gradient of 50/50 to 75/25). The desired fractions were collected and the solvents evaporated in vacuo to yield 6-(4-fluoro-phenyl)-2-m-tolyloxymethyl-7,8-dihydro-6H-imidazo[1,2-c]pyrimidin-5-one (34 mg, 48% yield). $^1$H NMR (500 MHz, CDCl$_3$) δ ppm 2.33 (s, 3H), 3.29 (t, J=6.6 Hz, 2H), 4.00 (t, J=6.6 Hz, 2H), 5.01 (s, 2H), 6.76-6.88 (m, 3H), 7.09-7.21 (m, 3H), 7.28-7.36 (m, 2H), 7.56 (s, 1H).

33. Preparation of 6-(5-Fluoro-6-methyl-pyridin-2-yl)-2-phenoxymethyl-7,8-dihydro-6H-imidazo[1,2-c]pyrimidin-5-one

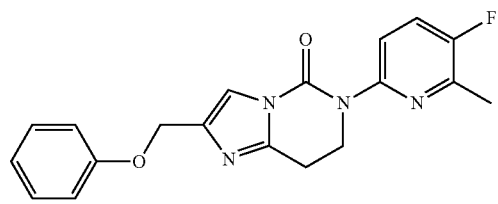 [SMILES: Cc1nc(N2CCc3nc(COc4ccccc4)cn3C2=O)ccc1F]

A solution of 6-(5-fluoro-6-methyl-pyridin-2-yl)-2-phenoxymethyl-6H-imidazo[1,2-c]pyrimidin-5-one (20 mg, 0.057 mmol) in a mixture of DMF (0.6 mL) and MeOH (0.6 mL) was hydrogenated in a H-cube reactor (1 mL/min, 30 mm Raney nickel cartridge, 80° C., full hydrogen mode, 1 cycle). The solvents were evaporated in vacuo and the crude product was purified by RP HPLC (C18 XBridge 19×100 5 um, gradient from 80% of 0.1% solution of ammonium formate/ammonium hydroxide buffer pH 9 solution in water and 20% CH₃CN to 0% of 0.1% solution of ammonium formate/ammonium hydroxide buffer pH 9 solution in water and 100% ACN) to yield 6-(5-fluoro-6-methyl-pyridin-2-yl)-2-phenoxymethyl-7,8-dihydro-6H-imidazo[1,2-c]pyrimidin-5-one (8.2 mg, 41% yield). $^1$H NMR (400 MHz, CDCl$_3$) δ ppm 2.49 (d, J=3.0 Hz, 3H), 3.24 (t, J=6.7 Hz, 2H), 4.35 (t, J=6.7 Hz, 2H), 5.02 (s, 2H), 6.97 (br. t, J=7.4, 7.4 Hz, 1H), 7.00-7.05 (m, 2H), 7.27-7.33 (m, 2H), 7.39 (t, J=8.6 Hz, 1H), 7.59 (s, 1H), 7.65 (dd, J=8.8, 3.2 Hz, 1H).

34. Preparation of 6-(4-Fluoro-phenyl)-3-iodo-2-phenoxymethyl-7,8-dihydro-6H-imidazo[1,2-c]pyrimidin-5-one

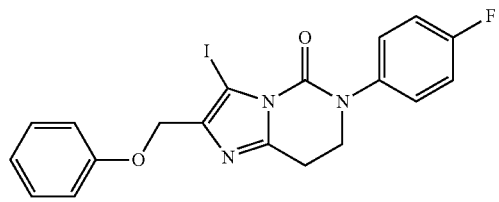

N-iodosuccinimide (73.4 mg, 0.33 mmol) was added to a stirred solution of 6-(4-fluoro-phenyl)-2-phenoxymethyl-7,8-dihydro-6H-imidazo[1,2-c]pyrimidin-5-one (0.1 g, 0.3 mmol) in a mixture of ACN (2 mL) and acetic acid (2 mL). The mixture was stirred at RT for 3 days. The mixture was diluted with DCM and washed with a saturated solution of Na$_2$CO$_3$. The organic layer was separated, dried (Na$_2$SO$_4$), filtered and the solvents evaporated in vacuo. The crude product was triturated with MeOH to yield 6-(4-fluoro-phenyl)-3-iodo-2-phenoxymethyl-7,8-dihydro-6H-imidazo[1,2-c]pyrimidin-5-one (46 mg, 56% yield) as a brown solid, that was used in the next step without further purification.

35. Preparation of 3-Chloro-6-(4-fluoro-phenyl)-2-phenoxymethyl-7,8-dihydro-6H-imidazo[1,2-c]pyrimidin-5-one

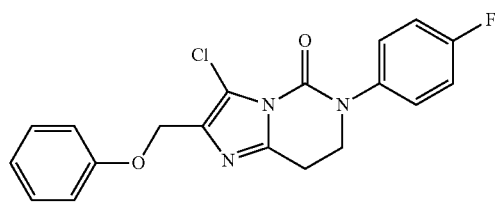 [SMILES: O=C1N(c2ccc(F)cc2)CCc2nc(COc3ccccc3)c(Cl)n21]

N-chlorosuccinimide (30.5 mg, 0.23 mmol) was added to a stirred solution of 6-(4-fluoro-phenyl)-2-phenoxymethyl-7,8-dihydro-6H-imidazo[1,2-c]pyrimidin-5-one (0.1 g, 0.3 mmol) in DMF (3.25 mL). The mixture was stirred at 150° C. for 20 minutes under microwave irradiation. The solvent was evaporated in vacuo and the crude product was purified by flash column chromatography (silica; AcOEt in DCM with a gradient of 0/100 to 15/85). The desired fractions were collected and the solvents evaporated in vacuo to yield 3-chloro-6-(4-fluoro-phenyl)-2-phenoxymethyl-7,8-dihydro-6H-imidazo[1,2-c]pyrimidin-5-one (21 mg, 27% yield) as a white solid. $^1$H NMR (400 MHz, CDCl$_3$) δ ppm 3.27 (t, J=6.6 Hz, 2H), 3.99 (t, J=6.6 Hz, 2H), 4.99 (s, 2H), 6.95-7.01 (m, 1H), 7.01-7.07 (m, 2H), 7.09-7.17 (m, 2H), 7.27-7.36 (m, 4H).

36. Preparation of 3-Bromo-6-(4-fluoro-phenyl)-2-phenoxymethyl-7,8-dihydro-6H-imidazo[1,2-c]pyrimidin-5-one

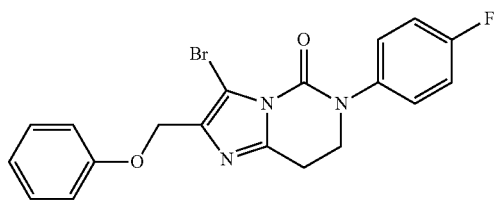 [SMILES: O=C1N(c2ccc(F)cc2)CCc2nc(COc3ccccc3)c(Br)n21]

Benzoyl peroxide (7.2 mg, 0.03 mmol) was added to a stirred solution of N-bromosuccinimide (30.58 mg, 0.33 mmol) and 6-(4-fluoro-phenyl)-2-phenoxymethyl-7,8-dihydro-6H-imidazo[1,2-c]pyrimidin-5-one (0.1 g, 0.3 mmol) in DCE (5 mL). The mixture was stirred at RT for 16 hours. The solvent was evaporated in vacuo and the crude product was purified by flash column chromatography (silica; AcOEt in DCM with a gradient of 0/100 to 10/90). The desired fractions were collected and the solvents evaporated in vacuo to yield 3-bromo-6-(4-fluoro-phenyl)-2-phenoxymethyl-7,8-dihydro-6H-imidazo[1,2-c]pyrimidin-5-one (57 mg, 35% yield) as a white solid.

37. Preparation of 6-(4-Fluoro-phenyl)-3-methyl-2-phenoxymethyl-7,8-dihydro-6H-imidazo[1,2-c]pyrimidin-5-one

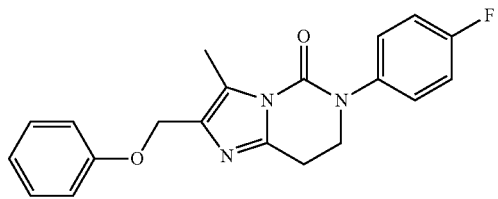 [SMILES: Cc1c(COc2ccccc2)nc2n1C(=O)N(c1ccc(F)cc1)CC2]

Tetrakis(triphenylphosphine)palladium(0) (6.4 mg, 0.0055 mmol) was added to a stirred suspension of 3-bromo-6-(4-fluoro-phenyl)-2-phenoxymethyl-7,8-dihydro-6H-imidazo[1,2-c]pyrimidin-5-one (116 mg, 0.18 mmol), methylboronic acid (55.05 mg, 0.92 mmol) and K$_2$CO$_3$ (76.3 mg, 0.23 mmol) in a mixture of 1,4-dioxane (7.07 mL) and DMF (1.77 mL) under nitrogen and in a sealed tube. The mixture was stirred at 150° C. for 45 minutes under microwave irradiation. The solvents were evaporated in vacuo and the crude product was purified by flash column chromatography (silica; 7 M solution of ammonia in MeOH in DCM with a gradient of 0/100 to 1.5/98.5 and then AcOEt in DCM with a gradient of 0/100 to 10/90). The desired fractions were collected and the solvents evaporated in vacuo. The product was purified by RP HPLC (C18 XBridge 19×100 5 um, gradient from 80% of 0.1% solution of ammonium formate/ammonium hydroxide buffer pH 9 solution in water and 20% CH$_3$CN to 0% of 0.1% solution of ammonium formate/ammonium hydroxide buffer pH 9 solution in water and 100% MeOH) to yield 6-(4-fluoro-phenyl)-3-methyl-2-phenoxymethyl-7,8-dihydro-6H-imidazo[1,2-c]pyrimidin-5-one (36.5 mg, 56% yield). $^1$H NMR (400 MHz, CDCl$_3$) δ ppm 2.52 (s, 3H), 3.26 (t, J=6.5 Hz, 2H), 3.98 (t, J=6.6 Hz, 2H), 4.96 (s, 2H), 6.97 (br. t, J=7.4, 7.4 Hz, 1H), 7.00-7.06 (m, 2H), 7.09-7.18 (m, 2H), 7.27-7.37 (m, 4H).

38. Compounds

Compounds were synthesized represented by the formula:

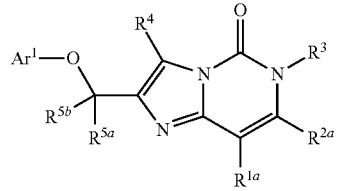

wherein Ar$^1$ and R$^3$ were as described in Table 111 below. R$^{2a}$, R$^4$, R$^{5a}$, and R$^{5b}$ were H, and R$^{1a}$ was as indicated in the table. The synthetic methods used to prepare the indicated were as described in the preceding examples with a reference example method as noted in the table.

Compounds were synthesized represented by the formula:

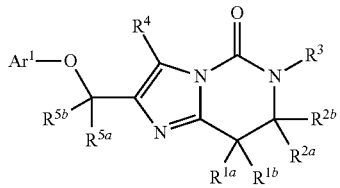

wherein Ar$^1$ and R$^3$ were as described in Table IV below. R$^{1a}$, R$^{1b}$, R$^{2a}$, R$^{2b}$, R$^4$, R$^{5a}$, and R$^{5b}$ were H. The synthetic methods used to prepare the indicated were as described in the preceding examples with a reference example method as noted in the table.

Analytical data for the numbered compound in Table V corresponds to the number given in the first column of either Table 111 or Table IV. LCMS: [M+H]+ means the protonated mass of the free base of the compound; Rt means retention time (in minutes); and Method refers to the LCMS method used.

TABLE III
| Compound Number | Ar¹ | R³ | R¹ᵃ | R²ᵃ | R⁴ | Reference Example* |
|---|---|---|---|---|---|---|
| 1 | 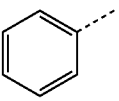 | H | H | H | H | 6 |
| 2 | 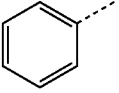 | —CH₃ | H | H | H | 23 |
| 3 | 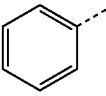 | 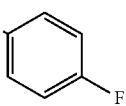 | H | H | H | 23 |
| 4 | 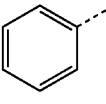 | 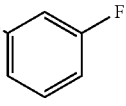 | H | H | H | 23 |
| 5 | 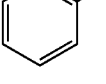 | 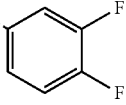 | H | H | H | 23 |
| 6 | 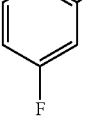 | 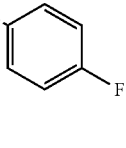 | H | H | H | 23 |
| 7 | 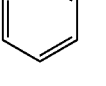 | 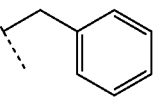 | H | H | H | 23 |
| 8 | 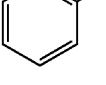 | 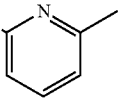 | H | H | H | 24 |
| 9 | 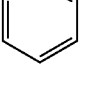 | 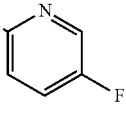 | H | H | H | 24 |
| 10 | 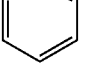 | 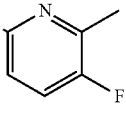 | H | H | H | 24 |
| 11 | 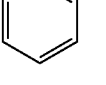 | 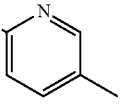 | H | H | H | 24 |
| 12 | 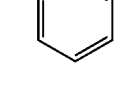 | 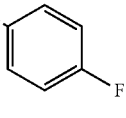 | H | H | H | 23 |
| 13 | 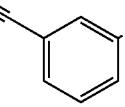 | 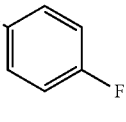 | H | H | H | 23 |

TABLE III-continued

| Compound Number | Ar¹ | R³ | R¹ᵃ | R²ᵃ | R⁴ | Reference Example* |
|---|---|---|---|---|---|---|
| 14 | 4-F-phenyl | 4-F-phenyl | H | H | H | 23 |
| 15 | phenyl | 4-methyl-pyridin-2-yl | H | H | H | 24 |
| 16 | 4-F-phenyl | 3-CF₃-phenyl | H | H | H | 23 |
| 17 | phenyl | cyclopropylmethyl | H | H | H | 23 |
| 18 | pyridin-2-yl | 4-F-phenyl | H | H | H | 23 |
| 19 | pyridin-3-yl | 4-F-phenyl | H | H | H | 23 |
| 20 | phenyl | 4-F-phenyl | F | H | H | 23 |
| 21 | 4-Cl-phenyl | 3-CF₃-phenyl | H | H | H | 23 |
| 22 | 4-CN-phenyl | 3-CF₃-phenyl | H | H | H | 23 |
| 23 | phenyl | 5-F-4-methyl-pyridin-2-yl | H | H | H | 24 |
| 24 | phenyl | 6-(dimethylamino)-pyridin-2-yl | H | H | H | 24 |

TABLE III-continued

| Compound Number | Ar¹ | R³ | R¹ᵃ | R²ᵃ | R⁴ | Reference Example* |
|---|---|---|---|---|---|---|
| 25 |  | 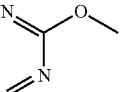 | H | H | H | 25 |
| 26 |  |  | I | H | H | 23 |
| 27 |  |  | CH₃ | H | H | 26 |
| 28 |  |  | H | CH₃ | H | 23 |
| 29 |  |  | H | H | Cl | 27 |
| 30 |  |  | H | H | Br | 23 |

*Reference Example 6 is 2-phenoxymethyl-6H-imidazo[1,2-C]pyrimidin-5-one; Reference Example 23 is 6-(4-fluoro-phenyl)-2-phenoxymethyl-6H-imidazo[1,2-c]pyrimidin-5-one; Reference Example 24 is 6-(4-fluoro-phenyl)-2-phenoxymethyl-6H-imidazo[1,2-c]pyrimidin-5-one; Reference Example 25 is 6-(2-methoxy-pyrimidin-4-yl)-2-phenoxymethyl-6H-imidazo[1,2-c]pyrimidin-5-one; Reference Example 26 is 6-(4-fluoro-phenyl)-8-methyl-2-phenoxymethyl-6H-imidazo[1,2-c]pyrimidin-5-one; and, Reference Example 27 is 3-chloro-6-(4-fluoro-phenyl)-2-phenoxymethyl-6H-imidazo[1,2-c]pyrimidin-5-one. The reference example corresponds to the numbering of synthetic examples above, and is not the same as the number for compound number as given in Tables I-V.

TABLE IV

| Compound Number | Ar¹ | R³ | R⁴ | Reference Example* |
|---|---|---|---|---|
| 31 |  |  | H | 28 |
| 32 |  |  | H | 28 |
| 33 |  |  | H | 29 |
| 34 | 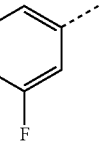 |  | H | 29 |
| 35 |  |  | H | 30 |

TABLE IV-continued

| Compound Number | Ar¹ | R³ | R⁴ | Reference Example* |
|---|---|---|---|---|
| 36 |  |  | H | 31 |
| 37 | 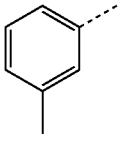 |  | H | 32 |
| 38 |  |  | H | 33 |
| 39 |  |  | H | 33 |

TABLE IV-continued

| Compound Number | Ar¹ | R³ | R⁴ | Reference Example* |
|---|---|---|---|---|
| 40 | phenyl | 4-fluoro-5-methylpyridin-2-yl | H | 33 |
| 41 | phenyl | 4-fluorophenyl | I | 34 |
| 42 | phenyl | 4-fluorophenyl | Cl | 35 |
| 43 | phenyl | 4-fluorophenyl | Br | 36 |
| 44 | phenyl | 4-fluorophenyl | CH₃ | 37 |

*Reference Example 28 is 6-(4-fluoro-phenyl)-2-phenoxymethyl-7,8-dihydro-6H-imidazo[1,2-c]pyrimidin-5-one; Reference Example 29 is 2-(3-fluoro-phenoxymethyl)-6-(4-fluoro-phenyl)-7,8-dihydro-6H-imidazo[1,2-c]pyrimidin-5-one; Reference Example 30 is 2-(4-fluoro-phenoxymethyl)-6-(4-fluoro-phenyl)-7,8-dihydro-6H-imidazo[1,2-c]pyrimidin-5-one; Reference Example 31 is 6-(5-methyl-pyridin-2-yl)-2-phenoxymethyl-7,8-dihydro-6H-imidazo[1,2-c]pyrimidin-5-one; Reference Example 32 is 6-(4-fluoro-phenyl)-2-m-tolyloxymethyl-7,8-dihydro-6H-imidazo[1,2-c]pyrimidin-5-one; Reference Example 33 is 6-(5-fluoro-6-methyl-pyridin-2-yl)-2-phenoxymethyl-7,8-dihydro-6H-imidazo[1,2-c]pyrimidin-5-one; Reference Example 34 is 6-(4-fluoro-phenyl)-3-iodo-2-phenoxymethyl-7,8-dihydro-6H-imidazo[1,2-c]pyrimidin-5-one; Reference Example 35 is 3-chloro-6-(4-fluoro-phenyl)-2-phenoxymethyl-7,8-dihydro-6H-imidazo[1,2-c]pyrimidin-5-one; Reference Example 36 is 3-bromo-6-(4-fluoro-phenyl)-2-phenoxymethyl-7,8-dihydro-6H-imidazo[1,2-c]pyrimidin-5-one; and, Reference Example 37 is 6-(4-fluoro-phenyl)-3-methyl-2-phenoxymethyl-7,8-dihydro-6H-imidazo[1,2-c]pyrimidin-5-one.

TABLE V

| Compound Number | M.p (° C.) | [M + H]⁺ | $R_t$ | LCMS Method |
|---|---|---|---|---|
| 1 | n.d. | 242 | 1.19 | 1 |
| 2 | 130.9 | 256 | 1.47 | 1 |
| 3 | 142.3 | 336 | 2.41 | 1 |
| 4 | 123.4 | 336 | 2.45 | 1 |
| 5 | 296.6 | 354 | 2.62 | 1 |
| 6 | 141.1 | 354 | 2.55 | 1 |
| 7 | 122.3 | 3.32 | 2.59 | 1 |
| 8 | >300 | 333 | 2.49 | 2 |
| 9 | n.d. | 337 | 2.42 | 2 |
| 10 | 199.5 | 351 | 2.74 | 2 |
| 11 | 209.4 | 333 | 2.50 | 2 |
| 12 | >300 | 293 | 3.50 | 2 |
| 13 | 165.0 | 361 | 2.49 | 2 |
| 14 | 163.4 | 354 | 2.69 | 2 |
| 15 | 239.4 | 333 | 2.42 | 2 |
| 16 | >300 | 404 | 3.19 | 2 |
| 17 | 102.1 | 296 | 2.45 | 2 |
| 18 | 282.3 | 337 | 2.15 | 2 |
| 19 | >300 | 337 | 1.70 | 2 |
| 20 | 110.7 | 354 | 2.88 | 2 |
| 21 | 141.8 | 420 | 3.49 | 2 |
| 22 | 189.4 | 411 | 2.91 | 2 |
| 23 | 203.1 | 351 | 2.64 | 2 |
| 24 | 136.0 | 362 | 2.97 | 2 |
| 25 | 171.2 | 350 | 1.90 | 3 |
| 26 | n.d. | 462 | 3.84 | 5 |
| 27 | 146.9 | 350 | 2.88 | 2 |
| 28 | 143.6 | 350 | 2.63 | 2 |
| 29 | 170.3 | 370 | 3.01 | 2 |
| 30 | n.d. | 414 | 3.21 | 2 |
| 31 | 195.2 | 338 | 2.33 | 1 |
| 32 | >300 | 338 | 2.43 | 1 |
| 33 | 165.4 | 356 | 2.55 | 1 |
| 34 | 141.1 | 355 | 2.50 | 1 |
| 35 | 182.3 | 356 | 3.37 | 4 |
| 36 | n.d. | 335 | 2.45 | 2 |
| 37 | 169.3 | 352 | 2.84 | 2 |
| 38 | n.d. | 353 | 2.68 | 2 |
| 39 | 135.0 | 339 | 2.32 | 2 |
| 40 | 196.5 | 353 | 2.59 | 2 |
| 41 | n.d. | 464 | 3.68 | 5 |
| 42 | 200.1 | 372 | 2.88 | 2 |
| 43 | n.d. | 416 | 3.65 | 5 |
| 44 | 160.4 | 352 | 2.75 | 2 |

39. Generation of Human mGluR5 Stable Cell Line

Human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK)293A cells were then transfected with human mGluR5a pcDNA3.1(−) using LipofectAmine-2000 (Invitrogen) and monoclones were selected and tested for functional response using a $Ca^{2+}$ mobilization assay. Monoclones were named for the species ("H" for human) plus the location on the plate (e.g. "10H").

40. Cell-Based Functional Assay

HEK cells transfected with the human mGluR5a receptor (H10H or H12H cell line) were plated at 15,000 cells/well in clear-bottomed poly-D-lysine-coated assay plates (BD Falcon) in glutamate-glutamine-free growth medium and incubated overnight at 37° C. and 5% $CO_2$. Cell-lines used were either the H10H or H12H cell-lines expressing the human mGluR5 receptor. The following day, the growth medium was removed and the cells were washed with assay buffer containing 1× Hank's balanced salt solution (Invitrogen, Carlsbad, Calif.), 20 mM HEPES, 2.5 mM probenecid, pH 7.4 and left with 20 µL of this reagent. Following this step, the cells were loaded with calcium indicator dye, fluo-4 AM, to a final concentration of 2 µM and incubated for 40-45 min at 37° C. The dye solution was removed and replaced with assay buffer. Cell plates were held for 10-15 min at room temperature and were then loaded into the Functional Drug Screening System 6000 (FDSS 6000, Hamamatsu, Japan).

After establishment of a fluorescence baseline for about 3 seconds, the compounds of the present invention were added to the cells, and the response in cells was measured. 2.3 minutes later an $EC_{20}$ concentration of the mGluR5 receptor agonist glutamate was added to the cells, and the response of the cells was measured for about 1.7 minutes. All test compounds were dissolved and diluted to a concentration of 10 mM in 100% DMSO and then serially diluted into assay buffer for a 2× stock solution in 0.6% DMSO; stock compounds were then added to the assay for a final DMSO concentration of 0.3% after the first addition to the assay well. Calcium fluorescence measures were recorded as fold over basal fluorescence; raw data was then normalized to the maximal response to glutamate. Potentiation of the agonist response of the mGluR5 receptor in the present invention was observed as an increase in response to submaximal concentrations of glutamate in the presence of compound compared to the response to glutamate in the absence of compound.

41. Data Analysis

The concentration-response curves of compounds of the present invention, obtained in the presence of $EC_{20}$ of mGluR5 receptor agonist glutamate to determine positive allosteric modulation, were generated using Microsoft Excel with IDBS XLfit add-ins. The raw data file containing all time points was used as the data source in the analysis template. This was saved by the FDSS as a tab-delimitted text file. Data were normalized using a static ratio function ($F/F_0$) for each measurement of the total 350 values per well divided by each well's initial value. Data was then reduced as to peak amplitudes (Max—Initial Min) using a time range that starts approximately 1 second after the glutamate $EC_{20}$ addition and continues for approximately 40 seconds. This is sufficient time to capture the peak amplitude of the cellular Calcium response. Individual amplitudes were expressed as $\% E_{Max}$ by multiplying each amplitude by 100 and then dividing the product by the mean of the amplitudes derived from the glutamate $EC_{Max}$-treated wells. $pEC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly. Individual values falling outside the 95% prediction limits of the curve fit were automatically excluded from the fit. A compound was designated as a positive allosteric modulator if the compound showed a concentration-dependent increase in the glutamate $EC_{20}$ addition. $\% E_{Max}$ for compounds may be estimated using the resulting corresponding parameter value determined using the curve fit or by taking an average of the overall maximum response at a single concentration. These two methods are in good agreement for curves with a clear plateau at the high concentration range. For data that show an increase in the $EC_{20}$ response, but, do not hit a plateau, the average of the maximum response at a single concentration is preferred. For consistency purposes across the range of potencies observed, all $E_{Max}$ values reported in this application are calculated using the maximum average response at a single concentration. The $E_{max}$ (%) value for each compound reported in this application is defined as the maximum % effect obtained in a concentration-response curve of that compound expressed as a percent of the response of a maximally effect concentration of glutamate. Tables I and II above shows the pharmacological data obtained for a selected set of compounds.

For compounds showing a lower potency (e.g. as indicated by a lack of a plateau in the concentration response curve), but with a greater than a 20% increase in glutamate response, a potency of >10 µM ($pEC_{50}$<5) was estimated.

42. Prospective in Vivo Effects

Generally clinically relevant antipsychotic agents (both typical and atypical) display efficacy in preclinical behavior challenge models. In vivo effects of the compounds described in the preceding examples are expected to be shown in various animal behavioural challenge models known to the skilled person, such as amphetamine-induced or phencyclidine (PCP)-induced hyperlocomotion, and other models, such as NMDA receptor antagonist MK-801-induced locomotor activity. These models are typically conducted in rodent, such as rat or mouse, but may be conducted in other animal species as is convenient to the study goals. Compounds, products, and compositions disclosed herein are expected to show in vivo effects in various animal behavioural challenge models known to the skilled person, such as amphetamine-induced or phencyclidine (PCP)-induced hyperlocomotion in rodent, and other models, such as NMDA receptor antagonist MK-801-induced locomotor activity. These models are typically conducted in rodent, such as rat or mouse, but may be conducted in other animal species as is convenient to the study goals.

For example, compounds having a structure represented by a formula:

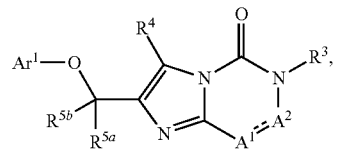

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2c}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —$NH_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof, are expected to show such in vivo effects.

Moreover, compounds prepared using the disclosed synthetic methods are also expected to show such in vivo effects.

43. 6-(4-fluorophenyl)-2-(phenoxymethyl)-7,8-dihydroimidazo[1,2-c]pyrimidin-5(6H)-one Activity in Induced Hyperlocomotion Animal Model

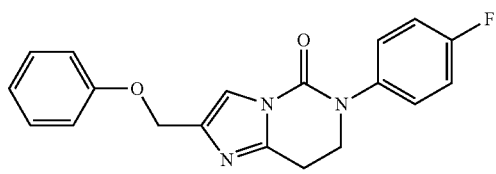 [SMILES: O=C1N(c2ccc(F)cc2)CCc2nc(COc3ccccc3)cn21]

Locomotor activity was assessed as mean distance traveled (cm) in standard 16×16 photocell testing chambers measuring 43.2 cm (Length)×43.2 cm (Width)×30.5 cm (Height) (Med Associates, St. Albans, Vt.). Animals were habituated to individual activity chambers for at least 30 min prior to drug administration. Following administration of drug or vehicle, activity was recorded for a 90 minute time period. Data was expressed as the mean (±SEM) distance traveled recorded in 5 min intervals over the test period. The data was analyzed using repeated measures analysis of variance (ANOVA) followed by post-hoc testing using Dunnett's test, when appropriate. A difference was considered significant when $p \leq 0.05$.

Figure 4:
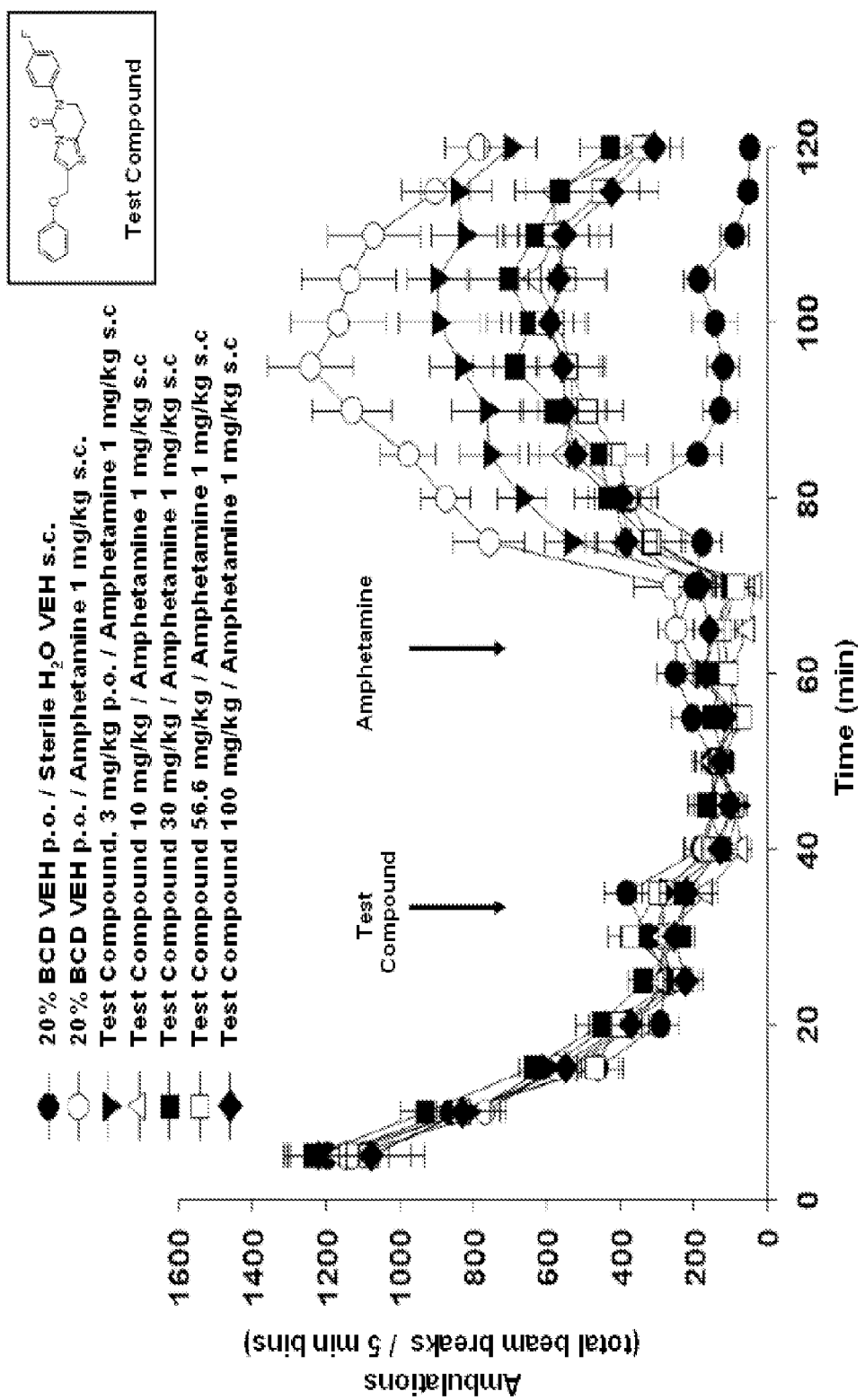
FIG. 4 shows a representative study demonstrating the dose-dependent reversal of amphetamine-induced hyperlocomotion by a representative disclosed compound.

Amphetamine sulfate was obtained from Sigma (Cat#A5880-1G; St. Louis, Mo.) and 10 mg was dissolved in 10 ml of water. The test compound, 6-(4-fluorophenyl)-2-(phenoxymethyl)-7,8-dihydroimidazo[1,2-c]pyrimidin-5 (6H)-one (labeled as "Test Compound" in FIG. 4), was formulated in a volume of 10 ml with an amount of drug appropriate to the dosage indicated. The appropriate amount of compound was mixed into a 20% 2-hydroxypropyl-β-cyclodextrin (2-HP-β-CD; indicated as "BCD" in FIG. 4) solution. The solution was formulated so that animals were injected with a volume equal to about 10× body weight. The mixture was then ultrahomogenized on ice for 2-3 minutes using the Dismembrator (Fisher Scientific Model 150T). Then the pH was checked using 0-14 EMD strips and adjusted to a pH of 6-7 if necessary. The mixture was then vortexed and stored in a warm sonication bath until time to be injected. Animals were administered samples of the following: (a) Amphetamine sulfate, 1 mg/kg, administered subcutaneously; and, (b) 6-(4-fluorophenyl)-2-(phenoxymethyl)-7,8-dihydroimidazo[1,2-c]pyrimidin-5(6H)-one, at the doses as indicated in FIG. 4 (indicated as "Test Compound" therein), and was administered by oral gavage.

The study was carried out using male Sprague-Dawley rats weighing 225 g-275 g, between 2-3 months old (Harlan, Inc., Indianapolis, Ind.), were used. The number of animals used is as indicated in FIG. 4. They were kept in the animal care facility certified by the American Association for the Accreditation of Laboratory Animal Care (AALAC) under a 12-hour light/dark cycle (lights on: 6 a.m.; lights off: 6 p.m.) and had free access to food and water. The experimental protocols performed during the light cycle were approved by the Institutional Animals Care and Use Committee of Vanderbilt University and conformed to the guidelines established by the National Research Council Guide for the Care and Use of Laboratory Animals.

The animals were habituated in Smart Open Field locomotor activity test chambers (Hamilton-Kinder, San Diego, Calif.) with 16×16 photobeams to automatically record locomotor activity for 30 min and then dosed with vehicle or test compound. The rats were then placed into cages. At 60 min, all rats were injected subcutaneously with 1 mg/kg amphetamine or vehicle and then monitored for an additional 60 min. Animals are monitored for a total of 120 minutes. Data are expressed as changes in ambulation defined as total number of beam breaks per 5 min periods.

The data for the dose-response studies were analyzed by a between-group analysis of variance. If there was a main effect of dose, then each dose group was compared with the vehicle amphetamine group. The calculations were performed using JMP IN 8 (SAS Institute, Cary, N.C.) statistical software and graphed using SigmaPlot9 (Saugua, Mass.). Dose-dependent results for reversal of amphetamine-induced hyperlocomotion by 6-(4-fluorophenyl)-2-(phenoxymethyl)-7,8-dihydroimidazo[1,2-c]pyrimidin-5(6H)-one are shown in FIG. 4. The following abbreviations are used: (a) "Test compound" refers to 6-(4-fluorophenyl)-2-(phenoxymethyl)-7,8-dihydroimidazo[1,2-c]pyrimidin-5(6H)-one; (b) subcutaneous administration of compound is indicated by "sc"; (c) oral gavage administration is indicated by "po"; and (d) amphetamine sulfate is indicated as "Amphetamine." The time of administration of amphetamine sulfate is indicated in FIG. 4 by "AMP" and the corresponding arrow. The vehicle for test compound is 20% wt/v HP-β-CD (indiocated as "BCD" in FIG. 4), and the vehicle for amphetamine is sterile water.

44. Prophetic Pharmaceutical Composition Examples

"Active ingredient" as used throughout these examples relates to one or more compounds having a structure represented by a formula:

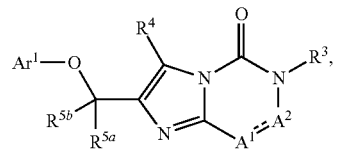

wherein ----- is an optional covalent bond, wherein valence is satisfied; wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halo, cyano, C1-C4 alkyl, C1-C4 alkyloxy, C1-C4 monohaloalkyl, and C1-C4 polyhaloalkyl; wherein when ----- is present and $A^1$ and $A^2$ are joined by a covalent double bond, $A^1$ is $CR^{1a}$, and $A^2$ is $CR^{2a}$; wherein $R^{1a}$ is selected from hydrogen, halogen, C1-C4 alkyl, C1-C4 monohaloalkyl, and C1-C4 polyhaloalkyl; wherein $R^{2a}$ is selected from hydrogen, C1-C4 alkyl, C1-C4 monohaloalkyl, and C1-C4 polyhaloalkyl; wherein when ----- is not present and $A^1$ and $A^2$ are joined by a covalent single bond, $A^1$ is $CR^{1b}R^{1c}$, and $A^2$ is $CR^{2b}R^{2c}$; wherein each of $R^{1b}$ and $R^{1c}$ are independently selected from hydrogen, fluoro, C1-C4 alkyl, C1-C4 monohaloalkyl, and C1-C4 polyhaloalkyl, or $R^{1b}$ and $R^{1c}$ are covalently bonded and, together with the intermediate atoms, comprise an optionally substituted 3- to 7-membered spirocycloalkyl; wherein each of $R^{2b}$ and $R^{2c}$ are independently selected from hydrogen, C1-C4 alkyl, C1-C4 monohaloalkyl, and C1-C4 polyhaloalkyl, or $R^{2b}$ and $R^{2c}$ are covalently bonded and, together with the intermediate atoms, comprise an optionally substituted 3- to 7-membered spirocycloalkyl; wherein $R^{1a}$ and $R^{2a}$, when present, are optionally covalently bonded and, together with the intermediate atoms, comprise an optionally substituted 3- to 7-membered fused cycloalkenyl; wherein $R^{1b}$ and $R^{2b}$, when present, are optionally covalently bonded and, together with the intermediate atoms, comprise an optionally substituted 3- to 7-membered fused cycloalkyl; wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$; wherein $Ar^2$ is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl), or $Ar^2$ is monocyclic heteroaryl substituted with 0-3 substituents independently selected from halo, cyano, C1-C4 alkyl, C1-C4 alkyloxy, C1-C4 monohaloalkyl, C1-C4 polyhaloalkyl, —NH$_2$, —NH(C1-C4 alkyl), and —N(C1-C4 alkyl)(C1-C4 alkyl); and, wherein $R^3$, when ----- is not present, is $Ar^2$; wherein $R^4$ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy; wherein each of $R^{5a}$ and $R^{5b}$ is independently selected from hydrogen, C1-C4 alkyl, C1-C4 monohaloalkyl, and C1-C4 polyhaloalkyl; or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

a. Tablets

A tablet can be prepared as follows:

| Component | Amount |
|---|---|
| Active ingredient | 5 to 50 mg |
| Di-calcium phosphate | 20 mg |
| Lactose | 30 mg |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

c. Injectable

A parenteral composition is prepared by stirring 1.5% by weight of active ingredient of the invention in 10% by volume propylene glycol in water.

d. Ointment

An ointment can be prepared as follows:

| Component | Amount |
|---|---|
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

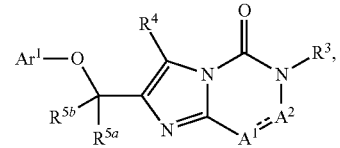

wherein ----- is an optional covalent bond, wherein valence is satisfied;

wherein $Ar^1$ is phenyl substituted with 0-3 substituents independently selected from halogen, cyano, C1-C4 alkyl, C1-C4 alkyloxy, C1-C4 monohaloalkyl, and C1-C4 polyhaloalkyl, or $Ar^1$ is monocyclic heteroaryl substituted with 0-3 substituents independently selected from halogen, cyano, C1-C4 alkyl, C1-C4 alkyloxy, C1-C4 monohaloalkyl, and C1-C4 polyhaloalkyl;

wherein when ----- is present and $A^1$ and $A^2$ are joined by a covalent double bond, $A^1$ is $CR^{1a}$, and $A^2$ is $CR^{2a}$;

wherein $R^{1a}$ is selected from hydrogen, halogen, C1-C4 alkyl, C1-C4 monohaloalkyl, and C1-C4 polyhaloalkyl;

wherein $R^{2a}$ is selected from hydrogen, C1-C4 alkyl, C1-C4 monohaloalkyl, and C1-C4 polyhaloalkyl;

wherein when ----- is not present and $A^1$ and $A^2$ are joined by a covalent single bond, $A^1$ is $CR^{1b}R^{1c}$, and $A^2$ is $CR^{2b}R^{2c}$;

wherein each of $R^{1b}$ and $R^{1c}$ are independently selected from hydrogen, fluoro, C1-C4 alkyl, C1-C4 monohaloalkyl, and C1-C4 polyhaloalkyl;

wherein each of $R^{2b}$ and $R^{2c}$ are independently selected from hydrogen, C1-C4 alkyl, C1-C4 monohaloalkyl, and C1-C4 polyhaloalkyl;

wherein $R^3$, when ----- is present, is selected from hydrogen, C1-C6 alkyl; C1-C6 alkyloxy; C1-C6 monohaloalkyl; C1-C6 polyhaloalkyl; C3-C8 cycloalkyl; C3-C8 heterocycloalkyl; (C3-C8 cycloalkyl)-C1-C6 alkyl-; (C3-C8 heterocycloalkyl)-C1-C6 alkyl-, and aromatic moiety $Ar^2$;

wherein Ar² is phenyl or benzyl or —(C2-C6)-phenyl, and substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl), or Ar² is monocyclic heteroaryl substituted with 0-3 substituents independently selected from halogen, cyano, C1-C4 alkyl, C1-C4 alkyloxy, C1-C4 monohaloalkyl, C1-C4 polyhaloalkyl, —NH₂, —NH(C1-C4 alkyl), and —N(C1-C4 alkyl)(C1-C4 alkyl); and, wherein R³, when ----- is not present, is Ar²;

wherein R⁴ is selected from hydrogen, halogen, cyano, C1-C4 alkyl, C1-C4 monohaloalkyl, C1-C4 polyhaloalkyl, C1-C4 alkylamino, C1-C4 dialkylamino, and C1-C4 alkoxy;

wherein each of $R^{5a}$ and $R^{5b}$ is independently selected from hydrogen, C1-C4 alkyl, C1-C4 monohaloalkyl, and C1-C4 polyhaloalkyl;

or a pharmaceutically acceptable salt or solvate thereof.

2. The compound of claim 1, having a structure represented by a formula:

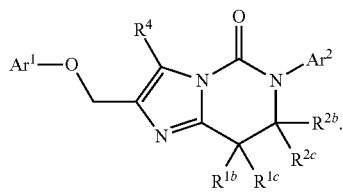

3. The compound of claim 1, having a structure represented by a formula:

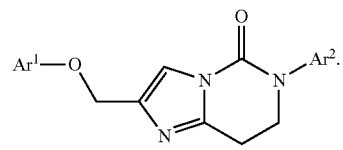

4. The compound of claim 1, having a structure represented by a formula:

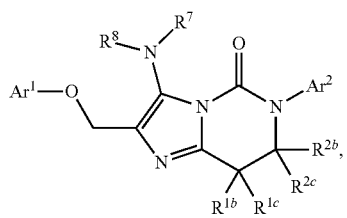

wherein R⁷ and R⁸ are independently selected from hydrogen and C1-C4 alkyl.

5. The compound of claim 1, having a structure represented by a formula:

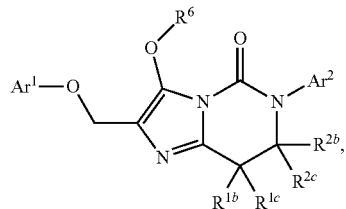

wherein R⁶ is C1-C4 alkyl.

6. The compound of claim 1, having a structure represented by a formula:

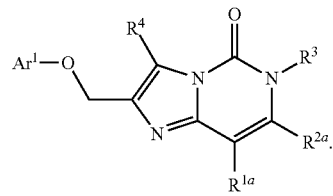

7. The compound of claim 1, having a structure represented by a formula:

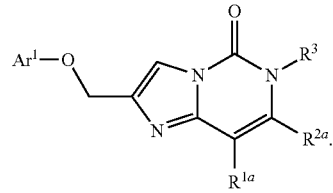

8. The compound of claim 1, having a structure represented by a formula:

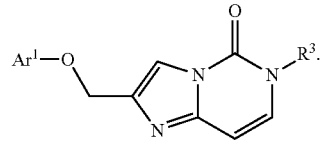

9. The compound of claim 1, having a structure represented by a formula:

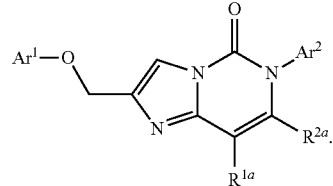

10. The compound of claim 1, having a structure represented by a formula:

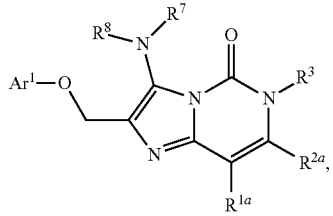

wherein $R^7$ and $R^8$ are independently selected from hydrogen and C1-C4 alkyl.

11. The compound of claim 1, having a structure represented by a formula:

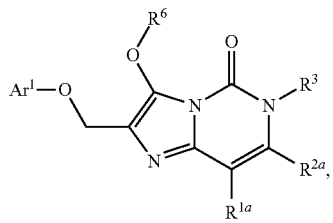

wherein $R^6$ is C1-C4 alkyl.

12. A pharmaceutical composition comprising a therapeutically effective amount of a compound of claim 1 and a pharmaceutically acceptable carrier.

* * * * *